US011110081B2

(12) United States Patent
Gordon et al.

(10) Patent No.: US 11,110,081 B2
(45) Date of Patent: *Sep. 7, 2021

(54) TACROLIMUS FOR IMPROVED TREATMENT OF TRANSPLANT PATIENTS

(71) Applicant: Veloxis Pharmaceuticals A/S, Cary, NC (US)

(72) Inventors: Robert D. Gordon, Sandy Springs, GA (US); Per Holm, Vanlose (DK); Anne-Marie Lademann, Klampenborg (DK); Tomas Norling, Lyngby (DK)

(73) Assignee: VELOXIS PHARMACEUTICALS, INC., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/085,291

(22) Filed: Oct. 30, 2020

(65) Prior Publication Data

US 2021/0046054 A1    Feb. 18, 2021

Related U.S. Application Data

(63) Continuation of application No. 15/041,986, filed on Feb. 11, 2016, now Pat. No. 10,864,199, which is a continuation of application No. 14/140,791, filed on Dec. 26, 2013, now abandoned, which is a continuation of application No. 13/167,420, filed on Jun. 23, 2011, now Pat. No. 8,664,239, which is a continuation of application No. 12/499,034, filed on Jul. 7, 2009, now Pat. No. 8,685,998, and a continuation-in-part of application No. PCT/DK2008/050130, filed on May 30, 2008.

(60) Provisional application No. 61/079,015, filed on Jul. 8, 2008.

(30) Foreign Application Priority Data

May 30, 2007    (DK) .............................. PA200700783
Nov. 7, 2007    (DK) .............................. PA200701573

(51) Int. Cl.
| | |
|---|---|
| *A61K 31/436* | (2006.01) |
| *A61K 9/20* | (2006.01) |
| *A61K 9/28* | (2006.01) |
| *A61K 9/16* | (2006.01) |
| *A61K 9/48* | (2006.01) |
| *A61K 9/00* | (2006.01) |
| *A61K 47/10* | (2017.01) |

(52) U.S. Cl.
CPC .......... *A61K 31/436* (2013.01); *A61K 9/0053* (2013.01); *A61K 9/1617* (2013.01); *A61K 9/1641* (2013.01); *A61K 9/1652* (2013.01); *A61K 9/2013* (2013.01); *A61K 9/2027* (2013.01); *A61K 9/2031* (2013.01); *A61K 9/2054* (2013.01); *A61K 9/2077* (2013.01); *A61K 9/284* (2013.01); *A61K 9/2846* (2013.01); *A61K 9/4891* (2013.01); *A61K 47/10* (2013.01); *Y10S 514/885* (2013.01)

(58) Field of Classification Search
CPC ........ A61K 31/436; A61K 9/053; A61K 9/10; A61K 9/1617; A61K 9/1623; A61K 31/4353; A61K 31/4375
See application file for complete search history.

(56) References Cited

U.S. PATENT DOCUMENTS

| | | |
|---|---|---|
| 5,601,844 A | 2/1997 | Kagayama et al. |
| 6,168,806 B1 | 1/2001 | Lee et al. |
| 6,204,243 B1 | 3/2001 | Posanski |
| 6,346,537 B1 | 2/2002 | Hata et al. |
| 6,387,918 B1 | 5/2002 | Yamanaka et al. |
| 6,440,458 B1 | 8/2002 | Yamashita et al. |
| 6,503,883 B1 | 1/2003 | Posanski |
| 6,576,259 B2 | 6/2003 | Yamashita et al. |
| 6,761,895 B2 | 7/2004 | Sawada et al. |
| 6,884,433 B2 | 4/2005 | Yamashita et al. |
| 6,884,436 B2 | 4/2005 | Kipp et al. |
| 7,994,214 B2 | 8/2011 | Holm |

(Continued)

FOREIGN PATENT DOCUMENTS

| | | |
|---|---|---|
| EP | 0184162 A2 | 6/1986 |
| EP | 0444659 A2 | 9/1991 |

(Continued)

OTHER PUBLICATIONS

Honbo et al., 1987, The orla dosage form of Fk-506, Transplantation Proceedings, vol. 19, No. 5, supplement 6, pp. 17-22.
Nishi et al., 2004, The Expression of Intestinal CYP3A4 in the Piglet Model, Transplantation Proceedings, vol. 36, No. 2, pp. 361-363.
Nishi, et al., 2004, The Colon Displays an Absorptive Capacity of Tacrolimus, Transplantation Proceedings, vol. 36, No. 2, pp. 364-366.
Sano et al., 2002, Oral FK 506 blood levels are elevated in pig short bowl model: Further investigations with co-administration of an intestinal CYP3A4 inhibitor, Transplantation Proceedings vol. 34, No. 3, pp. 1050-1051.

(Continued)

*Primary Examiner* — Micah Paul Young
(74) *Attorney, Agent, or Firm* — Blank Rome LLP

(57) ABSTRACT

An extended release oral dosage form comprising as active substance tacrolimus or a pharmaceutically active analogue thereof for a once daily immunosuppressive treatment of a patient in need thereof, preferable a kidney or liver transplant patient. The dosage form releases the active substance over an extended period of time. It also provides improved pharmacokinetic parameters due to an extended and constant in vivo release including substantial decreased peak concentrations, despite increased bioavailability, substantial extended times for maximal concentration, and higher minimal concentrations when compared with conventional immediate release dosage forms and a recent modified release tacrolimus dosage form.

28 Claims, 10 Drawing Sheets

(56) References Cited

U.S. PATENT DOCUMENTS

| | | | |
|---|---|---|---|
| 8,586,084 B2 * | 11/2013 | Holm | A61K 9/1623 424/468 |
| 8,591,946 B2 | 11/2013 | Holm | |
| 8,617,599 B2 | 12/2013 | Holm et al. | |
| 8,623,410 B2 | 1/2014 | Holm et al. | |
| 8,623,411 B2 * | 1/2014 | Holm | A61K 9/2054 424/468 |
| 8,664,239 B2 * | 3/2014 | Gordon | A61K 9/1641 514/291 |
| 8,685,998 B2 | 4/2014 | Gordon et al. | |
| 8,889,185 B2 * | 11/2014 | Holm | A61K 9/1641 424/468 |
| 8,889,186 B2 * | 11/2014 | Holm | A61K 9/2018 424/468 |
| 9,161,907 B2 * | 10/2015 | Holm | A61P 37/06 |
| 10,548,880 B2 * | 2/2020 | Holm | A61K 9/2031 |
| 2002/0028240 A1 | 3/2002 | Sawada et al. | |
| 2003/0180352 A1 | 9/2003 | Patel et al. | |
| 2005/0169993 A1 | 8/2005 | Yamashita et al. | |
| 2005/0249799 A1 | 11/2005 | Jacob et al. | |
| 2006/0045865 A1 | 3/2006 | Jacob et al. | |
| 2006/0159766 A1 | 7/2006 | Jenkins et al. | |
| 2006/0177500 A1 | 8/2006 | Shin et al. | |
| 2006/0210638 A1 | 9/2006 | Liversidge et al. | |
| 2006/0287352 A1 * | 12/2006 | Holm | A61K 9/0053 514/291 |
| 2007/0122482 A1 | 5/2007 | Holm et al. | |
| 2008/0181947 A1 | 7/2008 | Kojima et al. | |
| 2010/0008984 A1 * | 1/2010 | Holm | A61K 9/1652 424/464 |
| 2010/0105717 A1 | 4/2010 | Gordon et al. | |

FOREIGN PATENT DOCUMENTS

| | | |
|---|---|---|
| EP | 1064942 A1 | 1/2001 |
| EP | 1275373 A1 | 1/2003 |
| EP | 1275381 A1 | 1/2003 |
| EP | 1974722 A2 | 10/2008 |
| JP | 62277321 A | 12/1987 |
| JP | 200837808 | 12/2006 |
| KR | 20070014872 A | 10/2008 |
| WO | WO-9323022 A1 | 11/1993 |
| WO | WO-9824418 A1 | 6/1998 |
| WO | WO-9949863 A1 | 10/1999 |
| WO | WO-01/37808 | 5/2001 |
| WO | WO-01074359 A1 | 10/2001 |
| WO | WO-0195939 A1 | 12/2001 |
| WO | WO-03/004001 A1 | 1/2003 |
| WO | WO-2005004848 A1 | 1/2005 |
| WO | WO-2005020993 A1 | 3/2005 |
| WO | WO-2005020994 A1 | 3/2005 |
| WO | WO-2005050007 | 6/2005 |
| WO | WO-2006083130 A1 | 9/2005 |
| WO | WO-2006136175 A2 | 8/2006 |
| WO | WO-2005087195 A2 | 2/2007 |

OTHER PUBLICATIONS

Tacrolimus (Systemic) Drugs.com, Drug Information Online; http://www.drugs.com/mmx/tacrolimus.hmtl; pp. 1-43; Printed on Oct. 5, 2009.
U.S. Appl. No. 13/167,095, filed Jun. 23, 2011.
U.S. Appl. No. 13/167,160, filed Jun. 23, 2011.
U.S. Appl. No. 13/167,281, filed Jun. 23, 2011.
U.S. Appl. No. 13/167,334, filed Jun. 23, 2011.
U.S. Appl. No. 13/167,381, filed Jun. 23, 2011.
U.S. Appl. No. 13/029,304, filed Mar. 25, 2011.
U.S. Appl. No. 13/178,280, filed Jul. 7, 2011.
Kjaergaard, et al., Priling—Multiple Core Encapsulation, http://www.niroinic.com/food_Chemical/prilling_encapsulation.asp.
First M Roy et al., Modified Release Tacrolimus, Yonsei Medical Journal, vol. 45, No. 6, Dec. 31, 2004, pp. 1127-1131.
Heffron T G etl., Once-daily Tacrolimus extended-release formulations: 1-year post-conversion in stable pediatric live transplant recipients, American Journal of Transplantation Official Joural of The American Society of Transplantation and the American Society of Transplant Surgeons Jun. 2007, vol. 7, No. 6, Jun. 2007, pp. 1609-1615.
International Search Report issued in PCT/DK2008/050130 dated Nov. 3, 2008.
Barraclough, et al., Once-Versus Twice-Daily Tacrolimus Are the Formulations Truly Equivalent?, Drugs 2011; 71 (12): 1561-1577.
Budde, et al., A Phase III Randomized Trial of Conversion to Once-daily Extended Release MeltDose® Tacrolimus Tablets (LCP-Tacro™) from Twice-daily Tacrolimus Capsules (Prograf®): Efficacy and Safety Results from an Analysis of Sub-populations, TTs Poster , 2012.
Bunnapradist, et al., Conversion From Twice-Daily Tacrolimus to Once-Daily Extended Release Tacrolimus (LCPT): The Phase III Randomized MELT Trial, *American Journal of Transplantation*, doi: 10.1111/ajt.12035, 2012.
Gohel, et al., (Pharmaceutical Technology, 62-74. Sep. 2001).
Nigro, et al., Flexible dosing of once-daily LCP-Tacro tablets: morning vs. evening randomized crossover chronopharmacokinetic study, AST/ESOT Joint Meeting, Oct. 12-14, 2012, Nice, France.
Nigro, et al., Improved bioavailability and pharmacokinetics of tacrolimus with novel once-daily LCP-Tacro™ Meltdose formulation versus once-daily Advagraf® capsules, AST/ESOT Joint Meeting, Oct. 12-14, 2012, Nice, France.
Tada, et al., (J Clinicla Pharmacology, 43(8): 859-865 (2003).
Dew et al., "An Oral Preparation to Release Drugs in the Human Colon", Br. J. Clin. Pharmac. (1982), vol. 14, pp. 405-408.
Cross et al., "Tacrolimus Once-Daily Formulation in the Prophylaxis of Transplant Rejection in Renal or Liver Allograft Recipients", Drugs, 2007, vol. 67, No. 13, p. 1931-1943.

\* cited by examiner

TACROLIMUS FOR IMPROVED TREATMENT OF TRANSPLANT PATIENTS

RELATED U.S. APPLICATION

This application is a continuation of U.S. patent application Ser. No. 15/041,986, filed Feb. 11, 2016 which is a continuation of U.S. patent application Ser. No. 14/140,791, filed Dec. 26, 2013, now abandoned, which is a continuation of U.S. patent application Ser. No. 13/167,420, filed Jun. 23, 2011, now U.S. Pat. No. 8,664,239, which is a continuation of U.S. patent application Ser. No. 12/499,034, filed Jul. 7, 2009, now U.S. Pat. No. 8,685,998, which claims the benefit of U.S. Provisional Application No. 61/079,015, filed Jul. 8, 2008, and is a continuation-in-part of International Application No. PCT/DK2008/050130, filed May 30, 2008, which claims the benefit of Danish Patent Application Nos. PA 2007-00783, filed May 30, 2007, and PA 2007-01573, filed Nov. 7, 2007, each of which is hereby incorporated by reference in its entirety.

FIELD OF THE INVENTION

The present invention relates to an extended release oral dosage form comprising as active substance tacrolimus or a pharmaceutically active analogue thereof for use in a once daily immunosuppressive treatment of a patient in need thereof which dosage form releases the active substance over an very extended period of time and which in vivo provides a high bioavailability and an improved pharmacokinetic profile compared to conventional dosage forms.

BACKGROUND OF THE INVENTION

Tacrolimus, also known as FK-506 or FR-900506, is the active ingredient of Prograf®, Protopic®, and Advagraf® approved by the European Agency for the Evaluation of Medicinal Products (EMEA) at 23 Apr. 2007. During development of Advagraf® the product has been known as MR4. Details of Advagraf is described in the EPARs (European Public Assessment Reports) for authorised medicinal products for human use including the Scientific Discussion paper made public by EMEA on approval and the Product Information (label, Jan. 25, 2008 Advagraf-H-C-712-T-03) which is hereby incorporated by reference. Tacrolimus (Prograf®) was approved by the FDA in April of 1994 under NDA No. 050708 for the prophylaxis of organ rejection in patients receiving allogeneic liver transplants. It is also approved in the European Union, Japan, Canada and Switzerland and a variety of other countries under the same brand name. It is approved for the prophylaxis of organ rejection in patients receiving allogeneic liver, kidney or heart transplants. It has been estimated that 72% of all kidney and 89% of all liver transplant recipients are receiving tacrolimus.

Tacrolimus, administered as Prograf® capsules, exhibits a large inter- and intra-individual variability of its absorption and metabolism. Because of this variability, standard dosing is not an accurate predictor of concentration. In clinical use, tacrolimus dose-adjustments are frequently required based on monitoring of tacrolimus trough blood concentrations. Tacrolimus appears in the form of white crystals or crystalline powder. It is practically insoluble in water, freely soluble in ethanol and very soluble in methanol and chloroform.

The preparation of tacrolimus is described in EP-A-0 184 162 and analogues of tacrolimus are disclosed e.g. in EP-A-0 444 659 and U.S. Pat. No. 6,387,918, which are both hereby incorporated by reference.

Tacrolimus is a macrolide compound with useful immunosuppressive activity, antimicrobial activity and other pharmacological activities and is of value for the treatment or prevention of rejection reactions by transplantation of organs or tissues, graft versus host diseases, autoimmune diseases and infectious diseases.

Tacrolimus inhibits T-lymphocyte activation, although the exact mechanism of action is unknown. Experimental evidence suggest that tacrolimus binds to an intracellular protein, FKBP-12. A complex of tacrolimus-FKBP-12, calcium, calmodulin, and calcineurin is then formed and the phosphatase activity of calcineurin inhibited. This effect may prevent the dephosphorylation and translocation of nuclear factor of activated T-cells, a nuclear component thought to initiate gene transcription for the formation of lymphokines. The net result is the inhibition of T-lymphocyte activation, i.e. immunosupression.

Tacrolimus is extensively metabolized by the CYP3A4 isoenzyme in the gut wall and liver. CYP3A4 isoenzyme is present or expressed in all segments of the gastrointestinal tract including the colon. It has been observed that the absorption is negatively influenced by the simultaneous ingestion of food. Thus, the rate and extent of tacrolimus absorption were greatest under fasted conditions.

Tacrolimus is known to induce significant side effects, of nephro- or neuro-toxic origin, as well as GI side-effects and others.

Absorption of tacrolimus from the gastrointestinal tract after oral administration is rapid with a mean time-to-peak concentration ($t_{max}$) of approximately 1-2 hours after administration to healthy subjects or kidney or liver transplanted patients, but incomplete and variable. The bioavailability is generally as low as at the most about 20% after oral administration.

Frequently observed side effects are vomiting and nausea but side effects like tremor, headache, hypertension, renal dysfunction, hyperkalemia, hypomagnesaemia, hyperglycemia, insomnia, diarrhea, constipation, abdominal pain, nephrotoxicity and neurotoxicity are also observed.

For oral administration, tacrolimus is originally formulated and marketed as soft gelatine capsules comprising the equivalent of 0.5, 1 or 5 mg anhydrous tacrolimus and marketed under the trade name Prograf®. The recommended initial oral dose is from about 0.1 to 0.2 mg/kg/day in patients. The dose aims at a certain trough plasma level from about 5 to about 20 ng/ml. Prograf® is indicated for the prophylaxis of organ rejection in patients receiving allogeneic liver or kidney transplants. Details of the clinical pharmacology, pharmacokinetics, and clinical studies are described in the label approved by FDA on Apr. 27, 2006 for Prograf®, NDA no 50708 which is hereby incorporated by reference.

There remains a need for novel pharmaceutical compositions and/or dosage forms comprising tacrolimus exhibiting enhanced bioavailability and improved pharmacokinetic properties. An increased bioavailability in combination with an extended release formulation may allow a reduction in the dosage units taken by a patient, e.g. down to a single dose daily without risk of lack of clinical effect due to low doses in the last past of the dosing interval. Furthermore, fluctuations in the plasma concentration versus time profile may be significantly reduced. Further, enhanced bioavailability may also result in a more reproducible (i.e., less variable compared to that of Prograf®) release profile.

Sustained release tacrolimus formulations are described in WO99/49863 (Fujisawa Pharmaceutical Co.) inter alia granted as U.S. Pat. Nos. 6,440,458, 6,576,259 and 6,884,433 relating to a formulation where the time for dissolving 63.2% (T63.2% value) of the tacrolimus is between 0.7 and 15 hours. However, a formulation where 63.2% is released in 42 minutes seems to be only marginally different from the conventional immediate release formulation of tacrolimus having 68.4% released in 30 minutes. It is clearly stated that when the formulation has a T63.6 value of more than 15 hours, the release of the active ingredient will be so retarded that the active ingredient will be eliminated from the body before the effective blood concentration is reached. The most preferred embodiment is a sustained-release formulation with a T63.6 value of 2-5 hours. The formulations prepared according to the examples of the application all have a T63.6% value of from 1.9 (the formulation with the fastest release) to 8.2 hours for the formulation with the slowest release. It is further stated that the tacrolimus is excellently absorbed and variation of its absorbability is suppressed with the sustained release formulations. From the examples therein an improved bioavailability is obtained with all the tested formulations. The T63.6% values disclosed for these formulations are 3.0, 3.3, 2.0, and 2.5, respectively.

Inventors of the present application have in the patent application WO 2005/020993 also tested different formulations of tacrolimus in Beagle dogs and minipigs, however demonstrating that both a fast release tablet (Example 18) and a slow release tablet (Example 19) can result in improved bioavailability compared with Prograf®. This indicates that an improved bioavailability could be linked to having tacrolimus in a dissolved state in the dosage form which also appears from WO 2005/020994 by the same inventors relating to solid dispersions comprising tacrolimus. The fast release conventional product Prograf® comprises tacrolimus in a physical mixture of HPMC, lactose, cross carmellose sodium as described in Example 31 in WO99/49863 referred to above and owned by Fujisawa Pharmaceutical Co. (now Astellas) who developed Prograf®.

One major problem with modified or extended release dosage forms relies in the difficulty in obtaining a sufficient absorption in the lower part of the gastrointestinal tract as oral dosage forms entering the colon may easily be excreted before a substantial release has taken place. The release is generally decreased due to the lack of fluids and physical interaction of the dosage forms with the increasingly more solid content of the colon. In addition, the surface of absorption is several times smaller than the absorbing surface of the small intestines and this factor increases the time where the released active substance is subjected to possible degradation and entrapment in the solids present in the colon.

BRIEF SUMMARY OF THE INVENTION

It is generally accepted that extending the release too much may seriously affect the bioavailability even with substances expected to have a good permeation in the colon. For substances being substrates for CYP3A4, an advantage of the smaller concentration of the metabolizing enzymes in the lower GI can be expected from a bioavailability point of view. On the other hand, the relative higher concentration of the transporter system, P-glycoprotein, in the lower GI tract including the colon normally counteract the effect of the low concentration of CYP3A4 enzymes because the molecules that have entered the enterocyte are transported back into the intestinal lumen by the transporter. Tacrolimus is a known substrate for these mechanisms, both the CYP3A4 metabolism and the P-glycoprotein transporter system. Accordingly, an increased bioavailability cannot be correlated to an extension of a release in a simple linear way. The release may be carefully tailored to level out several counteracting factors of. These factors includes in the colon a lower area for absorption, a lower content of fluids, higher content of solids, bacterial degradation, higher impact from the P-glycoprotein transporter system, lower motility, differences in mucosal barrier and/or mucous composition and differences in pH along the colon compared with the small intestines. Accordingly, the control and timing of the in vivo release of the extended release dosage form in order to obtain a predictable release under the various physical conditions present along the GI tract is a challenge, especially bearing in mind that immune suppressive treatment in transplant patients requires blood concentrations within very narrow limits to balance efficacy (lack of rejection) and side effects (infections, nephrotoxicity, metabolic and cardiovascular disease, etc). Providing an improved formulation for a once daily treatment where the release is extended to the exact level where the resulting pharmacokinetic parameters are fully optimized without jeopardizing safety, i.e if intra- and inter-patient variance is high on important pharmacokinetic parameters, if correlation between minimal concentration and bioavailability is not present, a crucial factor in the treatment with a narrow therapeutic index drug such as tacrolimus where treatment failure is closely related to organ rejection and dose adjustments needs to take place on a safe basis. Further factors decreasing the risk of clinical success with a once daily formulation in organ transplant includes high prevalence of gastrointestinal complications having impact on the gastrointestinal parameters including transit times, pH, bacterial composition and other functions of the GI system. These complications include nausea, vomiting, and very frequently diarrhea.

Accordingly, the present inventors has surprisingly found that a dosage form which releases tacrolimus over an very extended and controlled period of time is capable of delivering tacrolimus in vivo in such a way that the tacrolimus at the same time is sufficiently absorbed to be understood in the way that tacrolimus is not lost in the lower gastrointestinal tract, the release is sufficiently slow to enable a very low absorption rate whereby the maximum concentration is controlled at a lower value and the minimum concentration is increased securing efficacy of the treatment for the full dosing interval of 24 hour. Very importantly, the minimum concentration obtained 24 hour after administration with an extended release formulation of the present invention is very predictable and can therefore be used as a marker for the overall bioavailability because a high correlation is achieved between the minimal concentration and the actual bioavailability observed in the previous 24 hour before the measurement of the minimal concentration. The minimal concentration can therefore be used safely as a tool for dosing and adjustments during the treatment.

It is believed that conventional in vitro dissolution methods correlate to or at least reflect the actual in vivo modified release profile in man. Accordingly, a difference in vitro in release rate between two formulations tested under the same conditions is expected to reflect a difference in the in vivo release rate. However, exceptions may apply if for instance one formulation has a pH dependent release and the other not, and the actual pH values for testing are not chosen to detect such difference. A clear example is when testing an enteric coated formulation at high pH it provides an immediate release in vitro, and a delayed release in vivo. Additionally, when comparing two extended formulations with different release mechanisms, for instance an osmotic driven release mechanism compared with an erodible dependent release mechanism, the same in vitro release profiles for the two products may in theory result in different in vitro profiles, however decreasing or increasing the dissolution rate will be reflected in vivo for each product. Accordingly, unless evidence to the contrary, and provided the methods are performed according to the prescriptions of the pharmacopeias, the conventional dissolution methods are useful tools for differentiating between formulations and the corresponding in vivo properties. In accordance herewith, the present invention provides, in its first aspect, an extended release oral dosage form comprising as active substance tacrolimus or an pharmaceutical active analogue thereof for a once daily immunosuppressive treatment of a patient in need thereof which dosage form releases the active substance over an very extended period of time. In a further aspect, the release is characterized by a substantial zero order release for a majority of the release.

Conventional in vitro dissolution methods includes the methods described in The United States Pharmacopeia (USP) the official public standards-setting authority for all prescription and over-the-counter medicines in USA and similar pharmacopeias for Europe and Japan. The preferred methods include the USP dissolution method I (basket) and method II (paddle) at 50 rpm, use of HPC to prevent adherence of drug to the equipment, and a pH of 4.5 for stability reasons. As tacrolimus is not protonized, pH does not affect solubility of the drug, however, a pH modification may be relevant in case pH sensitive inactive excipients are used in the formulation as a pH of 4.5 is not a pH generally present in the GI tract. Accordingly, it can be relevant to describe the degree of extension of the release with alternative dissolution methods. In addition, the extended formulation accordingly may be further characterized by additional dissolution methods, inter alia methods with different rotation speeds, different pH values, use of dissolution media simulating GI conditions (e.g simulation of the fasted and fed state, FaSSIP and FeSSIP medias), use of additives to the dissolution medium such as SLS to increase the wettability or the solubility of tacrolimus whereby the overall dissolution time measured is decreased (dissolution rate is increased).

The inventors have found that the bioavailability of tacrolimus is significantly increased and pharmacokinetic parameters substantially improved when tacrolimus is administered to a mammal in a extended release composition where the release and a timing of release of the active ingredient, i.e., an in vitro and vivo release profile, is extended for more than 15 hours measured by conventional dissolution methods used for tacrolimus dosage forms and measured in vivo via pharmacokinetic parameters of clinical relevance and relevant for proving extension of the release in vivo. These pharmacokinetic parameters includes: substantial extended time to reaching the maximal concentration; low maximal concentrations; high minimal concentrations, extended mean residence times and at the same time securing a surprisingly high bioavailability and excellent correlation between minimal concentrations and bioavailability.

The extended release is defined by a release of at the most 63.5% of the content of the active substance at the 12 hours time point defined by in vitro dissolution and when tested according to the USP II dissolution test (paddle) or USP I dissolution test (basket) form in a medium at pH 4.5 and comprising 0.005% hydroxypropylcellulose, and a rotation of 50 rpm. In a yet other aspect, the at the most 63.5% release of the active substance at the 12 hours time point is combined with a release of at least 8% at 4 hours and/or at least 15% at hour 8 to secure a continuous release throughout the dosing interval. If no release takes place for several hours after administration, the patient is in the risks that the tacrolimus blood concentration continues to fall to a value below the desired therapeutic lower limit for several hours of the 24 hours dosing interval.

In yet further aspects, the invention relates to use of the extended release composition for a more safe immunosuppressive treatment due to the improved pharmacokinetic profile obtained in healthy subjects and patients and demonstrated by several single dose and steady state pharmacokinetic trials in comparison with conventional commercially available dosage forms. The safe immunosuppressive treatment according to the invention also relates to a specific dosing regimen for conversion from a treatment on a twice daily Prograf® where the conversion is to be performed with a dosage in a ratio of 1:0.66-0.80 (according to the closest available tablet strength). Such dosage regimen resulting in comparable average blood concentrations during the dosing interval measured before and after the conversion as well similar bioequivalent exposure to Prograf® on other parameters such as AUC and minimum concentration.

DETAILED DESCRIPTION OF THE INVENTION

Definitions

Figure 1:
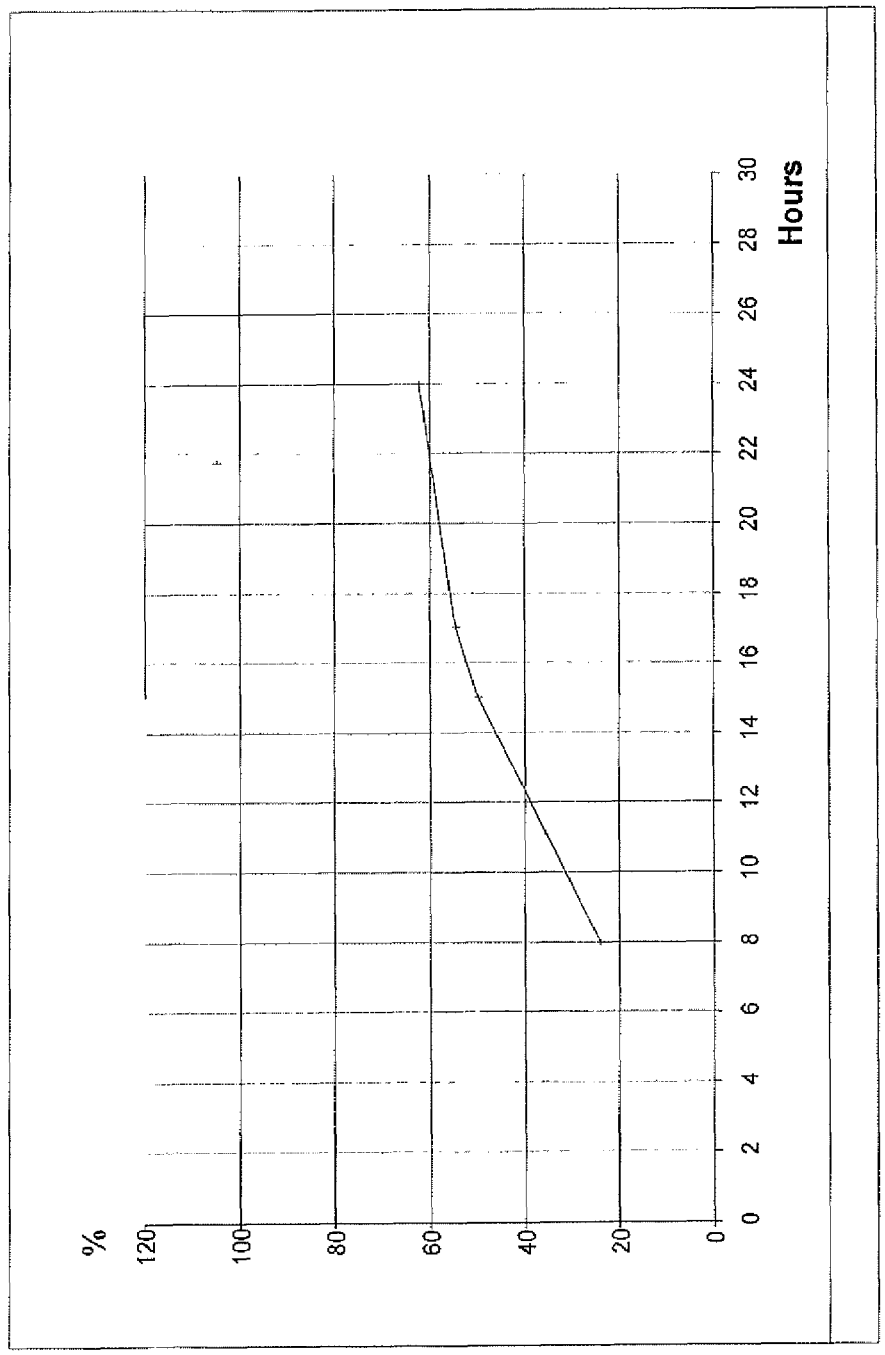
FIG. 1 shows the dissolution of an extended release formulation according to the invention and tested according to the USP II dissolution test (paddle) method in a medium at pH 4.5, comprising 0.005% hydroxypropylcellulose, and a rotation of 50 rpm.

As used herein, the term "active ingredient" or "active pharmaceutical ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and are present in the drug product in a modified form intended to furnish the specified activity or effect.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

In the present context, the term "amphiphilic" describes a molecule (as a surfactant) having a polar water-soluble group attached to a water-insoluble hydrocarbon chain. Thus, one end of the molecule is hydrophilic (polar) and the other is hydrophobic (non-polar).

In the present context, the term "hydrophobic" denotes a compound tending to be electrically neutral and non-polar, and thus preferring other neutral and nonpolar solvents or molecular environments.

As used herein, the term "vehicle" means any solvent or carrier fluid in a pharmaceutical product that has no pharmacological role. For example, water is the vehicle for xilocaine and propylene glycol is the vehicle for many antibiotics.

In the present context, the term "solid dispersion" denotes a drug or active ingredient or substance dispersed on a particulate level in an inert vehicle, carrier, diluent or matrix in the solid state, i.e. usually a fine particulate dispersion.

In the present context, the term "solid solution" denotes a drug or active ingredient or substance dissolved on a molecular level in an inert vehicle, carrier, diluent or matrix in the solid state.

As used herein, the term "analogue" means a chemical compound that is structurally similar to another.

The term "drug" means a compound intended for use in diagnosis, cure, mitigation, treatment, or prevention of disease in man or other animals.

In this context, the term "dosage form" means the form in which the drug is delivered to the patient. This could be parenteral, topical, tablet, oral (liquid or dissolved powder), suppository, inhalation, transdermal, etc.

As used herein, the term "bioavailability" denotes the degree means to which a drug or other substance becomes available to the target tissue after administration.

As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $c_{max}$, $AUC_{0-infinity}$, $AUC_{0-t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if the value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0-infinity}$ denotes the area under the plasma concentration versus time curve from time 0 to infinity; $AUC_{0-t}$ denotes the area under the plasma concentration versus time curve from time 0 to time t; $W_{50}$ denotes the time where the plasma concentration is 50% or more of $C_{max}$, $W_{75}$ denotes the time where the plasma concentration is 75% or more of $C_{max}$; and MRT denotes mean residence time for tacrolimus (and/or an analogue thereof). Swing denotes $(C_{max}-C_{min})/C_{min}$ and fluctuation $(C_{max}-C_{min})/C_{average}$. The fluctuation is suitable for the comparison of dosage forms providing different bioavailability.

In this context, the term "medicine" means a compound used to treat disease, injury or pain. Medicine is justly distributed into "prophylactic," i.e. the art of preserving health, and "therapeutic", i.e. the art of restoring health.

In the present context, the terms "controlled release" and "modified release" are intended to be equivalent terms covering any type of release of tacrolimus from a composition of the invention that is appropriate to obtain a specific therapeutic or prophylactic response after administration to a subject. A person skilled in the art knows how controlled release/modified release differs from the release of plain tablets or capsules. The terms "release in a controlled manner" or "release in a modified manner" have the same meaning as stated above. The terms include slow release (that results in a lower $C_{max}$ and later $t_{max}$, but t % is unchanged), extended release (that results in a lower $C_{max}$, later $t_{max}$, but apparent t % is longer); delayed release (that result in an unchanged $C_{max}$, but lag time and, accordingly, $t_{max}$ is delayed, and $t_{1/2}$ is unchanged) as well as pulsatile release, burst release, sustained release, prolonged release, chrono-optimized release, fast release (to obtain an enhanced onset of action) etc. Included in the terms is also e.g. utilization of specific conditions within the body, e.g. different enzymes or pH changes in order to control the release of the drug substance. The term extended release is chosen as this term is believed to most correctly cover the in vivo release of the product.

In this context, the term "erosion" or "eroding" means a gradual breakdown of the surface of a material or structure, for example of a tablet or the coating of a tablet. The term as used herein generally denotes the dissolution of a polymer responsible for extending the release being is faster than the dissolution of the active substance whereby the polymer erodes faster than the active substance is dissolved. In other words the release is primarily controlled by the erosion and not by the dissolution of the active substance in the polymer matrix system.

The present invention provides pharmaceutical products for improved treatment of conditions that respond to tacrolimus treatment, especially treatments where an immunosuppressive effect is desired.

The active ingredient in the inventive compositions is preferably tacrolimus or any analogue or derivative of tacrolimus, which exhibits either a pharmacological or a therapeutical activity, which is at least equivalent to that of tacrolimus (FK-506 or FR-900506). However, within the scope of the present invention is tacrolimus in any physical form (crystals, amorphous powder, any possible polymorphs, any possible solvates including the hydrate, anhydrate, complexes thereof etc.). Included is also any analogue, derivative or active metabolite of tacrolimus, pharmaceutically acceptable salts, solvates, complexes and prodrugs thereof. However, it is contemplated that a smaller particle size in micro and nano scale and preferable a molecular solution will contribute to a predictable and constant in vivo release of tacrolimus.

Thus, in a preferred embodiment, the present invention provides an extended release oral dosage form comprising as active substance tacrolimus or an pharmaceutical active analogue thereof for a once daily immunosuppressive treatment of a patient in need thereof which dosage form releases the active substance over an extended period of time defined by a release of at the most 63.5% of the content of the active substance at the 12 hours time point defined by in vitro dissolution and when tested according to the USP II dissolution test (paddle) or USP I dissolution test (basket) form in a medium at pH 4.5 and comprising 0.005% hydroxypropylcellulose, and a rotation of 50 rpm. It is generally accepted that the basket dissolution apparatus may be more suitable for capsules and the paddle dissolution apparatus is more suitable for disintegration tablets. However, the most suitable dissolution apparatus may be easily recognized via testing whether highest conformity is obtained by the one or other apparatus.

In a further embodiment, at the most 63.5% of the active substance is released at the 13 hours time point, more preferred at the 14 hours time point, such as at the 15 hours time point. In a preferred embodiment the in vitro release is taking place at a constant rated whereby a substantial zero order release profile may be obtained over an extended period of time. As a sufficient release is required at a time where the dosage form may have reached the colon such corresponding period where zero order release is desired may be defined by the release from 8 hours to 15 hours when tested according to the USP II dissolution test (paddle) or USP I dissolution test (basket) form in a medium at pH 4.5 and comprising 0.005% hydroxypropylcellulose, and a rotation of 50 rpm. As a solid dosage form may leave the stomach soon after ingestion or may be retained there for several hours before reaching the GI tract, it is also desired that the more initial release is well controlled as measured by a in vitro release which is an substantial zero order release profile over an extended period of time defined by the release from 2 hours to 10 hours when tested according to the USP II dissolution test (paddle) or USP I dissolution test (basket) form in a medium at pH 4.5 and comprising 0.005% hydroxypropylcellulose, and a rotation of 50 rpm.

In another embodiment of the invention, the addition of a surfactant to the release medium provides a release rate of the substance whereby the release of at the most 80% of the active substances is extended for a period of at least 7 hours, such as at least 8 hours, such as at least 9 hours, such as at least 10 hours, such as at least 11 hours, such as at least 12 hours such as at least 13 hours when tested in vitro according to the USP II dissolution test (paddle) or USP I dissolution test (basket) in a medium at pH 4.5 and comprising 0.005% hydroxypropylcellulose and further comprising 0.5% sodium lauryl sulfate (SLS), and a rotation of 50 rpm.

As mentioned previously, if the release is too extended the dosage form may be excreted before it has released completely or the release takes place too distally for a sufficient distribution. Accordingly, the content of the dosage form should be released with the rates indicated herein, however not be extended beyond a period of at the most 24 hours, such as at the most 23 hours, such as at the most 22 hours, such as at the most 21 hours such as at the most 21 hours, such as at the most 21 hours such as at the most 18 hours such as at the most 17 hours such as at the most 16 hours calculated for 80% of the content and with the addition of 0.5% sodium lauryl sulfate (SLS) to the dissolution medium.

Alternatively, or additionally, the dosage form is fulfilling the following condition wherein 63.5% of the release of the active substance is extended for a period of at the most 20 hours such as at the most 18 hours. Shorter dissolution periods may also be preferred as the upper limit such as at the most 16 hours such as at the most 15.5 hours also when tested in vitro according to the USP II dissolution test (paddle) or USP I dissolution test (basket) form in a medium at pH 4.5 and comprising 0.005% hydroxypropylcellulose, and a rotation of 50 rpm.

An extended release oral dosage wherein the release begins within 120 min such as within 90 minutes, such as within 60 minutes after deposition of the dosage form in the dissolution apparatus when tested in vitro according to the USP II dissolution test (paddle) or USP I dissolution test (basket) form in a medium at pH 4.5 and comprising 0.005% hydroxypropylcellulose, and a rotation of 50 rpm is indicative for a composition which will provide a predictable release profile as long as the release in the initial period, such as within the first 2 hours is not to fast. If no release takes place shortly after administration, the patient is in risk of to low concentrations. The patient is generally titrated according to the blood concentrations observed immediately before ingesting a daily dosage being the minimum concentration observed during the day. A delay in release will provide a later unknown minimal concentration.

The following release characteristics is regarded as within the scope of the invention:

a) An extended release oral dosage form which releases at the most about 20% w/w of the active substance within 1 hours, or within 2 hour, or within 3 hours, or within 4 hours or within 5 hours, when tested in vitro according to the USP II dissolution test (paddle) or USP I dissolution test (basket) form in a medium at pH 4.5 and comprising 0.005% hydroxypropylcellulose, and a rotation of 50 rpm.

b) An extended release oral dosage form which releases 40% w/w of the active substance within 10 to 14 hours such as, e.g., within about 11 to 13 hours, when tested in vitro according to the USP II dissolution test (paddle) or USP I dissolution test (basket) form in a medium at pH 4.5 and comprising 0.005% hydroxypropylcellulose, and a rotation of 50 rpm.

c) An extended release oral dosage form which releases 20% w/w of the total amount of the active substance released within 6 to 10 hours such as, e.g., within about 7 to 9 hours, when tested in vitro according to the USP II dissolution test (paddle) or USP I dissolution test (basket) form in a medium at pH 4.5 and comprising 0.005% hydroxypropylcellulose, and a rotation of 50 rpm.

d) An extended release oral dosage form which releases 50% w/w of the active substance within 13 to 17 hours such as, e.g., within about 14 to 16 hours, when tested in vitro according to the USP II dissolution test (paddle) or USP I dissolution test (basket) form in a medium at pH 4.5 and comprising 0.005% hydroxypropylcellulose, and a rotation of 50 rpm.

e) An extended release oral dosage form wherein the release profile is substantially linear in the period from 4 to 8 hours defined as a gradient or slope being within 25% of the gradient or slope measured at hour 6, such as within 15%, preferable within 10%.

f) An extended release oral dosage form wherein the release profile is substantially linear in the period from 6 to 10 hours defined as a gradient or slope being within 25% of the gradient or slope measured at hour 8, such as within 15%, preferable within 10%.

g) An extended release oral dosage form wherein the release profile is substantially linear in the period from 8 to 12 hours defined as a gradient or slope being within 25% of the gradient or slope measured at hour 10, such as within 15%, preferable within 10%.

h) An extended release oral dosage form wherein the release profile is substantially linear in the release period from the time point where 20% is released to the time point where 50% is released defined as a gradient or slope at the 80% time point being within 25% of the gradient or slope measured at the 20% time point.

i) An extended release dosage form according to any of the preceding claims wherein the release extending mechanism is not by a permeation controlling coat.

It is believed that release profile characteristics defined above significantly enhances the bioavailability of tacrolimus in mammals, since all or a major part of the active ingredient is in fact released in the gastrointestinal tract in such a manner that CYP3A4 metabolism is substantially avoided or at least significantly reduced. Further, it is contemplated that this effect is correlated to or at least reflected to the in vitro dissolution profile of the pharmaceutical composition and/or dosage forms of the invention, which profile is easily found when subjecting the composition and/or dosage form to a conventional in vitro dissolution method specified.

The desired release profile of the pharmaceutical composition may be provided by combining one or more of the following possibilities.

i) coating the composition with an enteric coating; and/or
ii) using a pharmaceutical composition comprising a solid dispersion or solid solution of active ingredient, i.e. tacrolimus or an analogue thereof, in a hydrophilic or water-miscible vehicle and one or more modifying release agents; and/or
iii) using a pharmaceutical composition comprising a solid dispersion or solid solution of active ingredient, i.e. tacrolimus or an analogue thereof, in a hydrophobic vehicle and optionally one or more modifying release agents.

An entero-coated formulation may however have the disadvantage of delaying the release without extending the release and should therefore be used in combination with an extending technology.

In another embodiment of the invention, and more preferred there is provided a extended release tacrolimus-containing pharmaceutical composition having the active ingredient dissolved or dispersed in a hydrophobic vehicle as described herein, preferably in an oil, an oily material, a wax or a fatty acid derivative, more preferably a wax having a low melting point such as for example glyceryl monostearate.

In yet another embodiment of the invention, there is provided a extended release tacrolimus-containing pharmaceutical composition having the active ingredient dissolved or dispersed in a hydrophilic or water-miscible vehicle as described herein, preferably a vehicle selected among polyethylene glycols, polyoxyethylene oxides, poloxamers, polyoxyethylene stearates, poly-epsilon caprolactone, polyglycolized glycerides such as Gelucire®, and mixtures thereof, more preferably polyethylene glycol optionally in mixture with a poloxamer. A specific example of a useful mixture is a mixture of 70 w/w % polyethylene glycol 6000 (PEG6000) and 30 w/w % poloxamer 188.

In a further aspect, the present invention relates to a pharmaceutical composition in particulate form comprising tacrolimus and/or an analogue thereof together with one or more pharmaceutically acceptable excipients, wherein the composition upon oral administration to a mammal in need thereof exhibits an $AUC/AUC_{Prograf®}$ value of at least about 1.3, the AUC values being determined under similar conditions.

As it appears from the examples herein that the bioavailability obtained after administration of a composition according to the invention is markedly improved. Thus, in specific embodiments, the $AUC/AUC_{Prograf®}$ value is at least about 1.25 such as about 1.5 or more, about 1.8 or more, about 1.9 or more, about 2.0 or more, the AUC values being determined under similar conditions.

After oral administration of a pharmaceutical composition according to the present invention it is contemplated that the plasma concentration versus time profile show an extended period of time in which the plasma concentration is maintained within the therapeutic window (i.e., the plasma concentration leads to a therapeutic effect) without leading to serious unwanted side effects. Thus, a reduction in peak concentration is also observed. Accordingly, the invention relates to a pharmaceutical composition in particulate form comprising tacrolimus together with one or more pharmaceutically acceptable excipient, wherein the composition upon oral administration to a mammal in need thereof releases tacrolimus in a controlled manner and exhibits a $C_{max}$ that is at the most about 80% of that of $C_{max}$ for Prograf® tablets such as, e.g., at the most about 75%, at the most about 70%, at the most about 65%, at the most about 60%, at the most about 55%, at the most about 50%, at the most about 45% or at the most about 40%.

In the present context the terms controlled release and extended release are intended to be equivalent terms covering any type of release of tacrolimus from a composition of the invention that is appropriate to obtain a specific therapeutic or prophylactic response after administration to a subject. A person skilled in the art knows how controlled release/extended release differs from the release of plain tablets or capsules. The terms "release in a controlled manner" or "release in a extended manner" have the same meaning as stated above.

The terms controlled release/extended release include slow release (that results in a lower $C_{max}$ and later $t_{max}$, but t % is unchanged), extended release (that results in a lower $C_{max}$, later $t_{max}$, but apparent t % is longer); delayed release (that result in an unchanged $C_{max}$, but lag time and, accordingly, $t_{max}$ is delayed, and t % is unchanged) as well as pulsatile release, burst release, sustained release, prolonged release, chrono-optimized release, fast release (to obtain an enhanced onset of action) etc. Included in the terms is also e.g. utilization of specific conditions within the body e.g. different enzymes or pH changes in order to control the release of the drug substance.

To be more specific, after oral administration to a mammal, including a human, of a pharmaceutical composition according to the present invention containing a dose of 5 mg tacrolimus, tacrolimus is released in a controlled manner and will exhibit a $C_{max}$ that is at the most about 30 ng/ml such as, e.g. at the most about 25 ng/ml or at the most about 20 ng/ml.

However, a reduction in peak concentration may not lead to a decrease in therapeutic effect as long as the plasma concentration of tacrolimus is maintained within the therapeutic window. Accordingly, the present invention also relates to a pharmaceutical composition, wherein $W_{50}$ is at least about 2 hours, such as, e.g., at least about 3 hours, at least about 4 hours, at least about 5 hours, at least about 6 hours, at least about 7 hours, at least about 8 hours, at least about 9 hours, about 10 hours or more, about 11 hours or more, about 12 hours or more, about 13 hours or about 14 hours or more.

Furthermore or moreover, a composition according to the invention has a $C_{diff}=[C_{max}-C_t (t=12 hours)]$ that is less than that of Prograf® under the same conditions. If $C_{diff}$ for Prograf® is set to 100 then $C_{diff}$ of a composition according to the invention is normally 90 or less such as, e.g., about 85 or less, about 80 or less, about 75 or less, about 70 or less, about 65 or less, about 60 or less, about 55 or less, about 50 or less, about 45 or less or about 40 or less.

More specifically, after oral administration to a mammal, including a human, of a pharmaceutical composition of the invention containing 5 mg of tacrolimus, tacrolimus is released in a controlled manner and exhibits a $C_{diff}$ of about 20 ng/mL or less such as, e.g., about 15 ng/mL or less, about 13 ng/mL or less or about 10 ng/mL or less.

A pharmaceutical composition according to the invention releases tacrolimus in a controlled manner in order to extend the therapeutic action of tacrolimus. In one aspect the release may be pH dependant, i.e. the release predominantly takes place after passage of the stomach. Such a pH dependent release is mainly provided by means of enteric coating material as described herein. The release may also be pH independent, e.g., by providing the composition with a controlled release coating such as, e.g. a cellulose based coating like e.g. ethylcellulose or by providing the composition in the form of a matrix composition such as, e.g., a hydrophilic cellulose polymer matrix type e.g. based on HPMC. A combination may of course also be employed.

In general, the change in bioavailability and/or the changes in other bioavailability related parameters are normally determined by in vivo studies in a suitable animal model testing the compositions in question together with e.g. Prograf® or a similar commercially available tacrolimus-containing product. The use of a dog model for establishing evidence of the bioavailability of certain formulations is general practice in the pharmaceutical industry.

The studies relevant for tacrolimus are non-radomized, cross-over studies, where each dog is its own control. Four dogs, and four treatments are normally applied. As no iv injections are given, the bioavailabilities obtained are relative.

Further it has surprisingly been found that the need for simultaneous food intake in order to secure a sufficient uptake of tacrolimus is significantly reduced or even completely abolished.

Thus, the pharmaceutical compositions according to the invention provide significant higher bioavailability of tacrolimus, which may reduce the number of daily administered dosage units, and reduce or abolish the need for administration in connection with food intake, which provide for a higher degree of freedom for the recipient of the pharmaceutical compositions, and consequently the patients acceptance and/or compliance may be significantly improved. Furthermore, the compositions provide a significant reduction in side effects, especially side effect related to a high peak concentration (such as, e.g., nephro- and neuro-toxicity, diarrhea, constipation, abdominal pain, nausea etc) and provide for an extended release of tacrolimus leading to a better therapy.

A further advantage of an extended-release-dosage-form invention is the possibility of obtaining an effective therapeutic response with a decreased dosage compared to traditional oral treatment. A similar bioavailability and an improved profile after administration in a dose is that is at the about most about 85% w/w such as, e.g., at the most about 80% w/w, at the most about 75%, at the most about 70% w/w, at the most about 65% w/w, at the most about 60% w/w, at the most about 55% w/w or at the most about 50% w/w of the dose of tacrolimus administered in the form of Prograf® or a similar commercially available tacrolimus-containing product or as a commercial available extended release product including Advagraf®.

Parameters often used in bioequivalence studies are $t_{max}$, $C_{max}$, $AUC_{0-infinity}$, $AUC_{0-t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0-infinity}$ denotes the area under the plasma concentration versus time curve from time 0 to infinity; $AUC_{0-t}$ denotes the area under the plasma concentration versus time curve from time 0 to time t; $W_{50}$ denotes the time where the plasma concentration is 50% or more of $C_{max}$; $W_{75}$ denotes the time where the plasma concentration is 75% or more of $C_{max}$; and MRT denotes mean residence time for tacrolimus (and/or an analogue thereof).

Two other main disadvantages associated with treatment or prophylaxis with tacrolimus is the relative high incidence of side effects and a relatively high inter-individual variation. It is envisaged that a composition according to the invention will lead to a reduction in side effects. The reduction may be in terms of reduced frequency or in terms of severity. The side effects in question include e.g., nephro- and neuro-toxicity, diarrhea, constipation, abdominal pain, nausea etc. In one aspect the invention concerns a pharmaceutical composition in particulate form comprising tacrolimus or an analogue thereof together with one or more pharmaceutically acceptable excipient, wherein the composition upon oral administration to a mammal in need thereof releases tacrolimus or an analogue thereof in a controlled manner and reduces side effects compared to those of Prograf® administered under the same conditions and in a dose that provides an equivalent therapeutic effect.

Increasing the bioavailability, the Area Under the Curve (AUC), will normally reduce the intra- and inter-variability related to absorption of a drug substance. This is particularly true; whenever the low and impaired bioavailability is a consequence of poor water solubility. It is contemplated that compositions according to the invention will provide a CV (Coefficient of Variation) on Area under Curve data that are significantly smaller than with Prograf® and like products.

As mentioned herein, one of the basic features of the present invention is that it is possible to obtain an improvement in the bioavailability by oral administration of an extended release dosage form according to the invention. Normally, a low bioavailability of a drug substance after oral administration is a barrier for design of a controlled or extended release composition of the drug substance due to the fact that it is almost impossible to obtain effective drug levels over a prolonged period of time. However, with the present technology it is possible to obtain a significantly improved bioavailability and thereby possible to design controlled, extended or delayed release compositions.

Tacrolimus is extensively metabolized by the CYP3A4 isoenzyme in the gut wall and liver. Accordingly, a suitable controlled release composition may be a composition that is designed to release tacrolimus in a delayed manner so as to avoid or reduce the CYP3A4 metabolism in the gastrointestinal tract.

Delayed release is mainly brought about by some kind of enteric coating. Whereas semi-permeable coating will show some kind of delayed release, it does not preciously enough "delay" release. Additionally it requires a certain amount of time to release the content. The coating sought for this invention, is a pH dependant coating. This type of coating is very resistant to release of drug until a certain pH is reached. Within very few ⅒th of pH, the film alters properties and becomes permeable. Examples of pH-sensitive polymers, which are relatively insoluble and impermeable at the pH of the stomach, but which are more soluble and permeable at the pH of the small intestine and colon include, but not limited to polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

pH-sensitive polymers of specific interest include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The release of the active substance from a composition having a delayed release coating could also be an enzymatic reaction, if for example Zein or mono/di-glyceride mixtures are employed as coating material.

Upon oral administration to a mammal, including a human, in need thereof, a controlled release pharmaceutical composition according to the present invention releases tacrolimus in such a manner that a plasma concentration of at least about 5 ng/ml such as, e.g., at least about 7.5 ng/mL or at least about 10 ng/mL for a time period of at least about 24 hours is obtained. In a specific aspect of the invention the difference between the peak plasma concentration and plasma concentration measured 24 hours after administration is at the most about 20 ng/mL such as, e.g., at the most about 10 ng/ml, at the most about 7.5 ng/mL or at the most about 5 ng/mL.

In a specific aspect, the invention provides a pharmaceutical composition or a solid dosage form that releases tacrolimus and/or an analogue thereof relatively fast so as to enable a relatively fast onset of therapeutic effect. In one aspect, the invention relates to a pharmaceutical composition in particulate form comprising tacrolimus and/or an analogue thereof together with one or more pharmaceutically acceptable excipient, wherein the composition upon oral administration to a mammal in need thereof in a controlled manner releases at least about 50% w/w of the total amount of tacrolimus or an analogue thereof within about 24 hours, such as, e.g., within about 22 hours, within about 20 hours, within about 18 hours, within about 15 hours or within about 12 hours.

Furthermore or alternatively, at least about 50% w/w of the total amount of tacrolimus and/or an analogue thereof is released within about 24 hours, within about 22 hours, within about 20 hours, within about 18 hours, within 15 hours, within about 12 hours, when tested in an in vitro dissolution test and employing a dissolution medium comprising a buffer having pH 7.5. Guidance for a suitable dissolution test is described in the Examples herein, but variations with respect to the specific method employed and the ingredients contained in the dissolution medium etc. are within the scope of the present invention. A person skilled in the art will know how to carry out a suitable dissolution test e.g. with guidance from USP, Ph.Eur. and the like including the FDA database of Dissolution Method for Drug Products. Suitable conditions for the in vitro dissolution test are employing USP dissolution test (paddle method) and a buffer pH 7.5 containing 2.5% SDS and 1 g/mL of pancreatin as dissolution medium.

In other embodiments, the following conditions are fulfilled with respect to in vitro dissolution test:

In other embodiments, the following conditions are fulfilled with respect to in vitro dissolution test performed under acidic conditions:

i) at the most about 30% w/w such as, e.g., at the most about 25% w/w, at the most about 20% w/w, at the most about 15% w/w or at the most about 10% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

ii) at the most about 10% w/w such as, e.g., at the most about 7.5% w/w, at the most about 5% w/w or at the most about 2.5% w/w of tacrolimus or an analogue thereof is released within 2 hours in an in vitro dissolution test employing a dissolution medium having a pH of at the most about 5 such as, e.g. at the most about 4.5, at the most about 4, at the most about 3.5, at the most about 3, at the most about 2 or at the most about 1.5;

iii) at the most about 60% w/w such as, e.g., at the most about 50% w/w, at the most about 40% w/w or at the most about 30% w/w of tacrolimus or an analogue thereof is released within 15 hours such as, e.g., within about 12 hours, when tested in an in vitro dissolution test employing a dissolution medium having a pH of at the most about 4.5 such as, e.g. at the most about 4.0, at the most about 3.5, at the most about 3, at the most about 2 or at the most about 1.5;

iv) at the most about 40% w/w such as, e.g., at the most about 30% w/w, at the most about 25% w/w or at the most about 20% w/w of tacrolimus or an analogue thereof is released within 6 hours when tested in an in vitro dissolution test employing a dissolution medium having a pH of at the most about 4.5 such as, e.g. at the most about 4.0, at the most about 3.5, at the most about 3, at the most about 2 or at the most about 1.5, and/or v) at the most about 30% w/w such as, e.g., at the most about 25% w/w, at the most about 20% w/w or at the most about 15% w/w of tacrolimus or an analogue thereof is released within 4 hours when tested in an in vitro dissolution test employing a dissolution medium having a pH of at the most about 4.5 such as, e.g. at the most about 4.0, at the most about 3.5, at the most about 3, at the most about 2 or at the most about 1.5.

Apart from tacrolimus, a composition of the invention may also comprise a further therapeutically, prophylactically and/or diagnostically active substance. Notably combinations of tacrolimus with at least one of the following active substances are of interest: Substances that are indicated for use in connection with organ transplantation such as, e.g., steroids, calcineurin inhibitors and/or anti-proliferative agents. Specific examples include prednisone, prednisolone, methylprednisone, cyclosporin, mycophenolate mofetil, azathioprine, sirolimus, everolimus, mycophenolate sodium, and FTY720 (Novartis).

The pharmaceutical compositions may be prepared by any convenient method such as, e.g., granulation, mixing, spray drying etc. A particularly useful method is the method described in WO 03/004001. Herein is described a process for the preparation of particulate material by a controlled agglomeration method, i.e. a method, which enables a controlled growth in particle size. The method involves spraying a first composition comprising e.g. tacrolimus and a carrier, which has been melted, onto a second solid carrier medium. Normally, the meltable carrier has a melting point of at least 5° C. but lower than the melting point of tacrolimus. The melting point of the carrier may be in the range of 10° C. to 150° C., such as, e.g., in the range of 30° C. to 100° C. or in the range of 40° C. to 50° C. is most preferred.

It is within the skills of the average practioner to select a suitable carrier being pharmaceutical acceptable, capable of dissolving or at least partly dissolve tacrolimus and having a melting point in the desired range using general knowledge and routine experimentation. Suitable candidate for carriers are described in WO 03/004001, which is herein incorporated by reference.

In the present context, suitable carriers are e.g. those mentioned as an oil or an oily-like material (as discussed later herein) as well as those disclosed in WO 03/004001.

An advantage of using the controlled agglomeration method described in WO 03/004001 is that it is possible to apply a relatively large amount of a melt to a particulate material without having an undesirable growth in particle size. Accordingly, in one embodiment of the invention, the particulate material of a pharmaceutical composition has a geometric weight mean diameter $d_{gw}$ of ≥10 μm such as, e.g. ≥20 μm, from about 20 to about 2000, from about 30 to about 2000, from about 50 to about 2000, from about 60 to about 2000, from about 75 to about 2000 such as, e.g. from about 100 to about 1500 μm, from about 100 to about 1000 μm or from about 100 to about 700 μm, or at the most about 400 μm or at the most about 300 μm such as, e.g., from about 50 to about 400 μm such as, e.g., from about 50 to about 350 μm, from about 50 to about 300 μm, from about 50 to about 250 μm or from about 100 to about 300 μm.

The particulate material obtained by the above-mentioned method has suitable properties with respect to flowability and/or compressibility and is therefore suitable for further processing into pharmaceutical dosage forms.

Solid Dispersion and/or Solid Solution of Tacrolimus

The solid dispersion or solid dispersion used in a preferred embodiment of the invention comprises an active ingredient selected among tacrolimus and analogues thereof, which ingredient is dispersed or dissolved in a hydrophilic or water-miscible vehicle having a melting point (freezing point or pour point) of at least 20° C. in a concentration of between about 0.01 w/w % and about 15 w/w %, and which dispersion is forming a solid dispersion or solid solution at ambient temperature (room temperature).

The concentration of the active ingredient in the hydrophilic or water-miscible vehicle is at the most 15 w/w %, preferably at the most 10 w/w %, preferably at the most 8 w/w %, more preferably at the most 6 w/w %, even more preferably at the most 5 w/w %, at the most 4% w/w, especially at the most 3 w/w %, in particular at the most 2% w/w; and/or is at least about 0.05 w/w %, preferably at least about 0.1 w/w %, more preferably at least about 0.5 w/w %, especially at least about 0.7 w/w %, in particular at least about 1 w/w %.

Physically, the combination of active ingredient and vehicle may either form a solid dispersion, i.e. the active ingredient is dispersed in the vehicle in particulate form, or may form a solid solution, i.e. the active ingredient is dissolved in the vehicle at a molecular level. The active ingredient and the vehicle may also form a solid dispersion having therein a part of the active ingredient dissolved at a molecular level. The physical state of the dispersion and/or solution may be determined by using various techniques such as Hot Stage Microscopy (HSM), Differential Scanning calorimetry (DSC), Scanning Electron Microscopy (SEM) optionally in combination with Energy Dispersive X-ray (EDX), and X-ray powder diffraction. In a preferred embodiment, the active ingredient is fully dissolved in the vehicle to form a solid solution at ambient temperature.

The solid dispersion of the invention exhibits a very fast immediate release of tacrolimus, when a composition comprising the dispersion or solution is tested in a dissolution test according to USP using an aqueous dissolution medium, and at least 50 w/w % of the active pharmaceutical ingredient is released within about 30 minutes, preferably within 20 minutes, more preferably within 15 minutes; such as at least 75 w/w % of the active pharmaceutical ingredient is released within about 40 minutes, or even better at least 90 w/w % of the active pharmaceutical ingredient is released within about 60 minutes, preferably within 45 minutes. For example, the test may be carried out according to the any method and any specifications cited in USP. Thus, the dissolution test may be carried out in an aqueous dissolution medium at a neutral or near-neutral pH, for example at pH 6.8, or at any acidic pH simulating the pH conditions in the gastrointestinal tract. However, variations with respect to the specific method employed and the ingredients contained in the dissolution medium etc. are within the scope of the present invention. A person skilled in the art will know how to carry out a suitable dissolution test e.g. with guidance from USP, Ph.Eur. and the like. Suitable conditions for the in vitro dissolution test are employing USP dissolution test (paddle method) and a buffer pH 7.5 containing 2.5% SDS and 1 g/mL of pancreatin as dissolution medium.

The hydrophilic or water-miscible vehicle to be used according to the invention is preferably one having a melting point (freezing point or pour point) of at least 20° C., more preferably at least 30° C., more preferably at least 40° C., more preferably at least 50° C., even more preferably at least 52° C., even more preferably at least 55° C., even more preferably at least 59° C., especially at least 61° C., in particular at least 65° C.

Examples of useful hydrophilic or water-miscible vehicles to be used according to this invention are selected from the group consisting of polyethylene glycols, polyoxyethylene oxides, poloxamers, polyoxyethylene stearates, poly-epsilon caprolactone, polyglycolized glycerides such as Gelucire®, and mixtures thereof.

In a preferred embodiment of the invention, the vehicle is a polyethylene glycol (PEG), in particular a PEG having an average molecular weight of at least 1500, preferably at least 3000, more preferably at least 4000, especially at least 6000. The polyethylene glycol may advantageously be mixed with one or more other hydrophilic or water-miscible vehicles, for example a poloxamer, preferably in a proportion (on a weight/weight basis) of between 1:3 and 10:1, preferably between 1:1 and 5:1, more preferably between and 3:2 4:1, especially between 2:1 and 3:1, in particular about 7:3. A specific example of a useful mixture is a mixture of PEG6000 and poloxamer 188 in the ratio 7:3.

For polyethylene glycols (PEG), the melting point (freezing point or pour point) increases as the average molecular weight increases. For example, PEG 400 is in the range of 4-8° C., PEG 600 is in the range of 20-25° C., PEG1500 is in the range of 44-48° C., PEG2000 is about 52° C., PEG 4000 is about 59° C., PEG 6000 is about 65° C. and PEG 8000 is about 61° C.

Useful poloxamers (also denoted polyoxypropylene-polyoxyethylene block copolymers) are for example poloxamer 188, poloxamer 237, poloxamer 338 or poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 Etc. Suitable Block Copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

In a preferred embodiment of the present invention, the poloxamer is poloxamer 188, which has an average molecular weight of about 8400 and a melting point of about 50-54° C.

Other useful hydrophilic or water-miscible vehicles may be polyvinylpyrrolidones, polyvinyl-polyvinylacetate copolymers (PVP-PVA), polyvinyl alcohol (PVA), polymethacrylic polymers (Eudragit RS; Eudragit RL, Eudragit NE, Eudragit E), cellulose derivatives including hydroxypropyl methylcellulose (HPMC), hydroxypropyl cellulose (HPC), methylcellulose, sodium carboxymethylcellulose, hydroxyethyl cellulose, pectins, cyclodextrins, galactomannans, alginates, carragenates, xanthan gums and mixtures thereof.

"Polyglycolized glycerides" denotes a mixture of mono-, di- and triglycerides and polyethylene glycol (PEG) mono- and diesters, preferably of molecular weight between 200 and 600, where appropriate of free glycerol and free PEG, whose HLB value is adjusted by the length of the PEG chain, and whose melting point is adjusted by the length of the chains of the fatty acids, of the PEG and by the degree of saturation of the fatty chains, and hence of the starting oil; examples of such mixtures are Gelucire®. Gelucire® compositions are inert semi-solid waxy materials which are amphiphilic in character and are available with varying physical characteristics. They are surface active in nature and disperse or solubilize in aqueous media forming micelles, microscopic globules or vesicles. They are identified by their melting point/HLB value. The melting point is expressed in degrees Celsius and the HLB (Hydrophile-Lipophile Balance) is a numerical scale extending from 0 to approximately 20. Lower HLB values denote more lipophilic and hydrophobic substances, and higher values denote more hydrophilic and lipophobic substances. The affinity of a compound for water or for oily substances is determined and its HLB value is assigned experimentally. One or a mixture of different grades of Gelucire® excipient may be chosen to achieve the desired characteristics of melting point and/or HLB value. They are mixtures of monoesters, diesters and/or triesters of glycerides of long chain ($C_{12}$ to $C_{18}$) fatty acids, and PEG (mono- and/or di) esters of long chain ($C_{12}$ to $C_{18}$) fatty acids and can include free PEG. Gelucire® compositions are generally described as fatty acid esters of glycerol and PEG esters or as polyglycolized glycerides. Gelucire® compositions are characterized by a wide range of melting points of from about 33° C. to about 64° C. and most commonly from about 35° C. to about 55° C., and by a variety of HLB values of from about 1 to about 14, most commonly from about 7 to about 14. For example, Gelucire® 50/13 designates a melting point of approximately 50° C. and an HLB value of about 13 to this grade of Gelucire®.

Pharmaceutically Acceptable Excipients

Examples of suitable excipients for use in a composition or solid dosage form according to the present invention include fillers, diluents, disintegrants, binders, lubricants and the like and mixtures thereof. As the composition or solid dosage form according to the invention may be used for different purposes, the choice of excipients is normally made taken such different uses into considerations. Other pharmaceutically acceptable excipients for suitable use are e.g. acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents and the like.

Examples of suitable fillers, diluents and/or binders include lactose (e.g. spray-dried lactose, α-lactose, β-lactose, Tabletose®, various grades of Pharmatose®, Microtose® or Fast-Floe), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for extended release etc.

Other additives in a composition or a solid dosage form according to the invention may be antioxidants like e.g. ascorbic acid, ascorbyl palmitate, butylated hydroxyanisole, butylated hydroxytoluene, hypophosphorous acid, monothioglycerol, potassium metabisulfite, propyl gallate, sodium formaldehylde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g. stabilizing agents. The concentration of an antioxidant and/or a stabilizing agent in the carrier composition is normally from about 0.1% w/w to about 5% w/w.

A composition or solid dosage form according to the invention may also include one or more surfactants or substances having surface-active properties. It is contemplated that such substances are involved in the wetting of the slightly soluble active substance and thus, contributes to improved solubility characteristics of the active substance.

Suitable excipients for use in a composition or a solid dosage form according to the invention are surfactants such as, e.g., amphiphillic surfactants as those disclosed in WO 00/50007 in the name of Lipocine, Inc. Examples of suitable surfactants are i) polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, ii) polyethylene glycol glycerol fatty acid esters, i.e. esters like the above-mentioned but in the form of glyceryl esters of the individual fatty acids; iii) glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like, iv) polyglycerized fatty acids like e.g. polyglycerol stearate, polyglycerol oleate, polyglycerol ricinoleate, polyglycerol linoleate, v) propylene glycol fatty acid esters such as, e.g. propylene glycol monolaurate, propylene glycol ricinoleate and the like, vi) mono- and diglycerides like e.g. glyceryl monooleate, glyceryl dioleae, glyceryl mono- and/or dioleate, glyceryl caprylate, glyceryl caprate etc.; vii) sterol and sterol derivatives;

viii) polyethylene glycol sorbitan fatty acid esters (PEG-sorbitan fatty acid esters) such as esters of PEG with the various molecular weights indicated above, and the various Tween® series;

ix) polyethylene glycol alkyl ethers such as, e.g. PEG oleyl ether and PEG lauryl ether;

x) sugar esters like e.g. sucrose monopalmitate and sucrose monolaurate;

xi) polyethylene glycol alkyl phenols like e.g. the Triton® X or N series; xii) polyoxyethylene-polyoxypropylene block copolymers such as, e.g., the Pluronic® series, the Synperonic® series, Emkalyx®, Lutrol®, Supronic® etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407;

xiii) sorbitan fatty acid esters like the Span® series or Ariacel® series such as, e.g. sorbinan monolaurate, sorbitan monopalmitate, sorbitan monooleate, sorbitan monostearate etc.;

xiv) lower alcohol fatty acid esters like e.g. oleate, isopropyl myristate, isopropyl palmitate etc.;

xv) ionic surfactants including cationic, anionic and zwitterionic surfactants such as, e.g. fatty acid salts, bile salts, phospholipids, phosphoric acid esters, carboxylates, sulfates and sulfonates etc.

When a surfactant or a mixture of surfactants is present in a composition or a solid dosage form of the invention, the concentration of the surfactant(s) is normally in a range of from about 0.1-80% w/w such as, e.g., from about 0.1 to about 20% w/w, from about 0.1 to about 15% w/w, from about 0.5 to about 10% w/w, or alternatively, from about 0.10 to about 80% w/w such as, e.g. from about 10 to about 70% w/w, from about 20 to about 60% w/w or from about 30 to about 50% w/w.

In a specific aspect of the invention, the at least one of the one or more pharmaceutically acceptable excipient is selected from the group consisting of silica acid or a derivative or salt thereof including silicates, silicon dioxide and polymers thereof; magnesium aluminosilicate and/or magnesium aluminometasilicate, bentonite, kaolin, magnesium trisilicate, montmorillonite and/or saponite.

Such materials are is especially useful as a sorption material for oils or oily-like materials in pharmaceuticals, cosmetics and/or foodstuff. In a specific embodiment, the material is used as a sorption material for oils or oily-like materials in pharmaceuticals. The material that has the ability to function as a sorption material for oils or oily-like materials is also denoted "oil sorption material". Furthermore, in the present context the term "sorption" is used to denote "absorption" as well as "adsorption". It should be understood that whenever one of the terms is used it is intended to cover the phenomenon absorption as well as adsorption.

Notably, the pharmaceutically acceptable excipient may comprise a silica acid or a derivative or salt thereof such as, e.g., silicon dioxide or a polymer thereof as a pharmaceutically acceptable excipient. Dependent on the quality employed a silicon dioxide may be a lubricant or it may be an oil sorption material. Qualities fulfilling the latter function seem to be most important.

In a specific embodiment, a composition or solid dosage form according to invention comprises a pharmaceutically acceptable excipient that is a silicon dioxide product that has properties corresponding to Aeroperl® 300 (available from Degussa, Frankfurt, Germany).

As it appears from the examples herein, a very suitable material is Aeroperl® 300 (including materials with properties like or corresponding to those of Aeroperl® 300).

Use of an oil sorption material in compositions or dosage forms according to the invention is very advantageous for the preparation of pharmaceutical, cosmetic, nutritional and/or food compositions, wherein the composition comprises oil or an oily-like material. One of the advantages is that is it possible to incorporate a relatively large amount of oil and oily-like material and still have a material that is solid. Thus, it is possible to prepare solid compositions with a relatively high load of oil or oily-like materials by use of an oil sorption material according to the invention. Within the pharmaceutical field it is an advantage to be able to incorporate a relatively large amount of an oil or an oily-like material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance. Thus, in a specific embodiment it is used in the preparation of pharmaceutical compositions.

In an important embodiment of the invention, at least a part of tacrolimus and/or an analogue thereof is present in the composition in the form of a solid solution including a molecular dispersion and a solid dispersion. Normally, 10% or more such as, e.g., 20% or more, 30% or more, 40% or more, 50% or more, 60% or more, 70% or more, 80% or more, 90% or more such as, e.g., 95% or more or about 100% w/w of tacrolimus and/or an analogue thereof is present in the composition in the form of a solid dispersion.

A solid dispersion may be obtained in different ways e.g. by employing organic solvents or by dispersing or dissolving the active substance in another suitable medium (e.g. an oil or an oily-like material that is in liquid form at room temperature or at elevated temperatures).

Solid dispersions (solvent method) may for example be prepared by dissolving a physical mixture of the active substance (e.g. a drug substance) and the carrier in a common organic solvent, followed by evaporation of the solvent. The carrier is often a hydrophilic polymer. Suitable organic solvents include pharmaceutical acceptable solvent in which the active substance is soluble such as methanol, ethanol, methylene chloride, chloroform, ethylacetate, acetone or mixtures thereof.

Suitable water soluble carriers include polymers such as polyethylene glycol, poloxamers, polyoxyethylene stearates, poly-ε-caprolactone, polyvinylpyrrolidone (PVP), polyvinylpyrrolidone-polyvinylacetate copolymer PVP-PVA (Kollidon VA64), poly-methacrylic polymers (Eudragit® RS, Eudragit® RL, Eudragit® NE, Eudragit® E) and polyvinyl alcohol (PVA), hydroxypropyl cellulose (HPC), hydroxypropyl methyl cellulose (HPMC), methyl cellulose, and poly(ethylene oxide) (PEO).

Polymers containing acidic functional groups may be suitable for solid dispersions, which release the active substance in a preferred pH range providing acceptable absorption in the intestines. Such polymers may be one ore more selected from the group comprising hydroxypropyl methylcellulose phtalate (HMPCP), polyvinyl acetate phtalate (PVAP), hydroxypropylmethylcellulose acetate succinate (HPMCAS), alginate, carbomer, carboxymethylcellulose, methacrylic acid copolymer (Eudragit L, Eudragit S), shellac, cellulose acetate phthalate (CAP), starch glycolate, polacrylin, methyl cellulose acetate phtalate, hydroxypropyulcellulose acetate phthalate, cellulose acetate terephtahalate, cellulose acetate isophthalate and cellulose acetate trimellitate.

Relative to the amount of the active substance and the polymer in the solid dispersion, the weight ratio of active substance to polymer may be in a range of from about 3:1 to about 1:20. However, narrower ranger of from about 3:1 to about 1:5, such as, e.g., from about 1:1 to about 1:3 or about may also be used.

The solid dispersion is preferably formed by spray drying techniques, controlled agglomeration, freeze-drying or coating on carrier particles or any other solvent removal process. The dried product contains the active substance present in the form of a solid dispersion including a molecular dispersion and a solid solution.

As an alternative to the use of organic solvents the drug and polymer may be co-grinded or extruded at elevated temperatures (melt extrusion).

The pharmaceutical compositions comprising tacrolimus at least partly in form of a solid dispersion or solution may in principle be prepared using any suitable procedure for preparing pharmaceutical compositions known within the art.

Apart from using the organic solvent based method, solid dispersion or solid solutions of tacrolimus and/or an analogue thereof may be obtained by dispersing and/or dissolving tacrolimus in the carrier composition used in the controlled agglomeration method. Stabilizing agents etc. may be added in order to ensure the stability of the solid dispersion/solution.

In another aspect, the invention relates to a method for the preparation of a pharmaceutical composition according to the invention. In general, any suitable method within the pharmaceutical field may be employed. However, in order to enable incorporation of a relatively high amount of an oil or an oily-like material especially the method described in WO 03/004001 has proved useful. WO 03/004001 is hereby incorporated by reference. The method comprises spraying a first composition in liquid form, said composition comprising a first vehicle or carrier and having a melting point above 5° C. onto a second composition comprising a second support or carrier material, said second composition e.g. being in the fluidized state and having a temperature below the melting point of the first vehicle or carrier. The active substance may be present in the first vehicle or carrier composition and/or in the second support or carrier composition. However, in those cases where tacrolimus and/or an analogue thereof are present, at least partly, in the form of as a solid dispersion, it is advantageous to incorporate or dissolve tacrolimus and/or an analogue thereof in the first vehicle or carrier composition. WO05020993A1 and WO05020994A1 of the present inventors additionally describe tacrolimus compositions by use of the technology and with extended release formulations thereof and are hereby incorporated by reference.

Solid Dosage Forms

The pharmaceutical composition according to the invention is in particulate form and may be employed as such. However, in many cases it is more convenient to present the composition in the form of granules, pellets, microspheres, nanoparticles and the like or in the form of solid dosage forms including tablets, capsules and sachets and the like.

A solid dosage form according to the invention may be a single unit dosage form or it may in the form of a poly-depot dosage form contain a multiplicity of individual units such as, e.g., pellets, beads and/or granules.

A solid dosage form according to the present invention comprises a pharmaceutical composition in particulate form as described above. The details and particulars disclosed under this main aspect of the invention apply mutatis mutandis to the other aspects of the invention. Accordingly, the properties with respect to increase in bioavailability, changes in bioavailability parameters, lack of diurnal effect as well as release of tacrolimus and/or an analogue thereof, etc., described and/or claimed herein for pharmaceutical compositions in particulate form, are analogous for a solid dosage form according to the present invention.

The recommended dosage range for Prograf® is 0.1 to 0.2 mg/kg/day given every 12 hours in two divided doses. Importantly, the blood levels have to be monitored.

The typical level for 1-3 months is 7-20 ng/mL and 4-12 months the levels should be 5-15 ng/mL. This is only guiding values and may vary from types of transplant and ethnicity.

The following was found for kidney transplant patients.

| | Caucasian n = 114 | | Black n = 56 | |
|---|---|---|---|---|
| Time After Transplant | Dose (mg/kg) | Trough Concentrations (ng/mL) | Dose (mg/kg) | Trough Concentrations (ng/mL) |
| Day 7 | 0.18 | 12.0 | 0.23 | 10.9 |
| Month 1 | 0.17 | 12.8 | 0.26 | 12.9 |
| Month 6 | 0.14 | 11.8 | 0.24 | 11.5 |
| Month 12 | 0.13 | 10.1 | 0.19 | 11.0 |

The expected dosage recommendation for products of the present invention will be from 0.02 mg/kg/day to 0.15 mg/kg/day, dosed once a day. Suitable dosage forms (strength) range from 0.1 mg to 15 mg of tacrolimus, preferably a strength selected from 0.5 mg, 1 mg, 2 mg and 5 mg.

Figure 2:
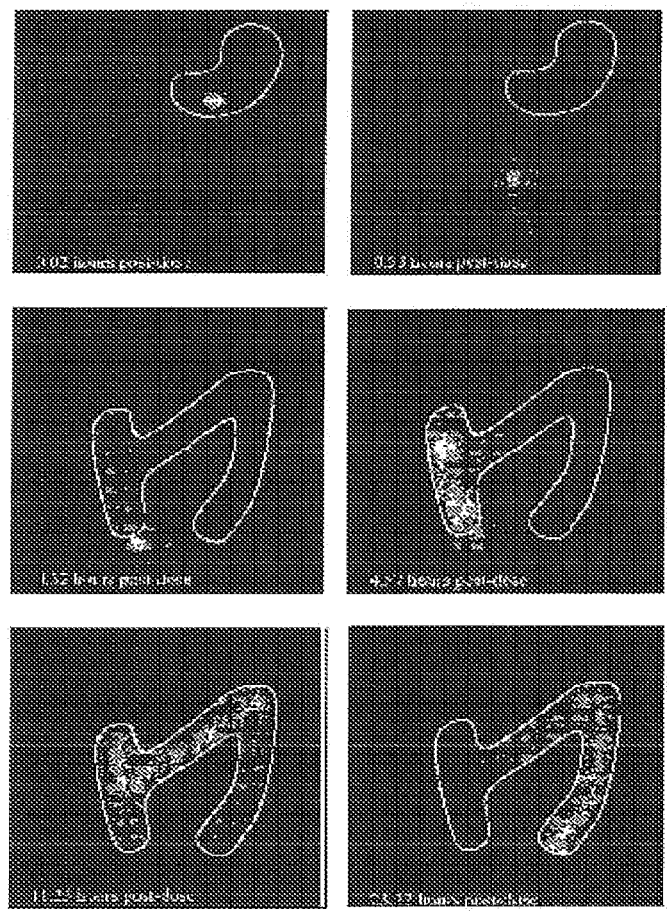
FIG. 2 is a scintigraphic evaluation of the location of release by use of an extended release formulation according to the parameter's of study 003. The figure demonstrates that the in vivo release with a formulation according to the present invention is extended to a degree where absorption takes place in the colon of the individual.

As demonstrated herein by scintigraphy and shown in FIG. 2, the release according to the present invention can take place even in the distal part of the colon and still being distributed to the mucosa and absorbed. The absorption of the extended release dosage form according to the invention is one where the in vivo release after oral administration to a subject takes place substantially in the colon such as release in one or more of the locations of colon *ascendens*, colon *transversum* and colon *decendens*.

Different embodiments of the invention relating to preferred pharmacokinetic parameters obtained with the extended release dosage form according to present invention are listed below.

In one embodiment, the invention relates to an extended release dosage form which when administered to a subject or a number of subjects provides an intra subject and/or an inter subject variability of the mean blood $T_{max}$ of tacrolimus which relative to that obtained from administration of the commercial product Advagraf® (MR4) dosage form or a bioequivalent extended release dosage form is decreased with at least 10%, such as at least 15%, such as at least 17.5%, such as at least 20%, such as at least 22.5%, such as at least 25%, such as at least 27.5% such as at least 30% when being determined under similar conditions and administered in similar molecular dosages of the tacrolimus.

In one embodiment, the invention relates to an extended release dosage form which when administered to a subject or a number of subjects provides an intra subject and/or an inter subject variability of the mean blood $C_{max}$ and/or $AUC_{(0-\infty)}$ of tacrolimus which relative to that obtained from administration of the commercial product Advagraf® (MR4) or a bioequivalent extended release dosage form is decreased with at least 10%, such as at least 15%, such as at least 17.5%, such as at least 20%, such as at least 22.5%, such as at least 25%, such as at least 27.5% such as at least 30% when being determined under similar conditions and administered in similar molecular dosages of the tacrolimus.

In one embodiment, the invention relates to an extended release dosage form, which when administered to a subject or a number of subjects provides a decreased $C_{max}$ value relative to that obtained by administration of the commercial product Advagraf® (MR4) or a bioequivalent extended release dosage form of at least about 10%, or at least about 15%, or at least about 20%, or at least about 30%, or at least about 35%, or at least about 40 or more, or at least about 45%, or at least about 50%, or at least about 55%, the $C_{max}$ values being determined under similar conditions and administered in similar molecular dosages of the tacrolimus.

In one embodiment, the invention relates to an extended release dosage form form which when administered to a subject or a number of subjects provides an increased bioavailability relative to that obtained by administration of the commercially product Advagraf® (MR4) or a bioequivalent extended release dosage form of at least about 20%, or at least about 25%, or at least about 30%, or at least about 35%, or at least about 40%, or at least about 45%, or at least about 50%, or at least about 55%, or at least about 60%, such as at least 65%, the bioavailability being determined as AUC(0-∞) and under similar conditions and administered in similar molecular dosages of the tacrolimus.

In one embodiment, the invention relates to an extended release dosage form which when administered to a subject or a number of subjects provides an intra subject and/or an inter subject variability of the mean blood $T_{max}$ of tacrolimus which relative to that obtained by administration of the commercially available Prograf® dosage form or a bioequivalent immediate release tacrolimus dosage form is decreased with at least 10%, such as at least 15%, such as at least 17.5%, such as at least 20%, such as at least 22.5%, such as at least 25%, such as at least 27.5% such as at least 30% when being determined under similar conditions and administered in similar molecular dosages of the tacrolimus.

In one embodiment, the invention relates to an extended release dosage form which when administered to a subject or a number of subjects provides an intra subject and/or an inter subject variability of the mean blood $C_{max}$ and/or $AUC_{(0-\infty)}$ of tacrolimus which relative to that obtained by administration of the commercially available Prograf® dosage form or a bioequivalent immediate release dosage form is decreased with at least 10%, such as at least 15%, such as at least 17.5%, such as at least 20%, such as at least 22.5%, such as at least 25%, such as at least 27.5% such as at least 30% when being determined under similar conditions and administered in similar molecular dosages of the tacrolimus.

In one embodiment, the invention relates to an extended release dosage form which when administered to a subject or a number of subjects provides a decreased $C_{max}$ value relative to that obtained by administration of the commercially available Prograf® dosage form or a bioequivalent immediate release dosage form of at least about 20%, or at least about 30%, or at least about 35%, or at least about 40%, or at least about 45%, or at least about 50% or more, or at least about 55%, or at least about 60%, or at least about 65%, when being determined under similar conditions and administered in similar molecular dosages of the tacrolimus.

In one embodiment, the invention relates to an extended release dosage form which when administered to a subject or a number of subjects provides an increased bioavailability relative to that obtained by administration of commercially available Prograf® dosage form or a bioequivalent immediate release dosage form of at least about 10%, or at least about 15%, or at least about 20%, or at least about 30%, or at least about 35%, or at least about 40 or more, or at least about 45%, or at least about 50%, or at least about 55%, the bioavailability being determined as AUC(0-∞) and under similar conditions and administered in similar molecular dosages of the tacrolimus.

In one embodiment, the invention relates to an extended release dosage form which when administered to a subject or a number of subjects after at least 4 hours fasted state in the evening provides an bioavailability which relative to that obtained after administration of the dosage form in the morning after at least 4 hours fasted state is at least 70%, such as at least 80%, preferable at least 85% more preferable at least 90% and preferable at least 95% of the value measured after administration in the morning.

In one embodiment, the invention relates to an extended release dosage form which when administered to a subject or a number of subjects after at least 4 hours fasted state in the evening provides a $C_{max}$ which relative to that obtained after administration of the dosage form in the morning after at least 4 hours fasted state is at least 70%, such as at least 80%, preferable at least 85% more preferable at least 90% and preferable at least 95% value measured after administration in the morning.

In one embodiment, the invention relates to an extended release dosage form wherein the bioavailability is independent of the dosing time of the day and thereby is suitable for a bedtime dosing regimen.

In one embodiment, the invention relates to an extended release dosage form which when comprising 5 mg of tacrolimus and when administered as a single dose to at least 6 healthy subjects in fasted state provides a mean maximal concentration ($C_{max}$) of tacrolimus of at the most 15 ng/mL, such as at the most 13 ng/mL and a mean AUC(0-96 h) of at least 45 mg·h/L, such as at least 55 mg·h/L, such as at least 60 mg·h/L.

In one embodiment, the invention relates to an extended release dosage form according to wherein the blood concentration 24 after administration of tacrolimus is at least 2 ng/mL such as at least 3 ng/mL such as at least 4 ng/mL.

In one embodiment, the invention relates to an extended release dosage form which when administered once daily in steady state to a healthy subject or a patient, the swing of the blood concentrations of tacrolimus measured as $(C_{max}-C_{min})/C_{min}$ is less than the swing observed when administering the Advagraf® dosage form or a bioequivalent extended release dosage form of tacrolimus in a once daily regimen and being determined under similar conditions and administered in similar molecular daily dosages of the tacrolimus. The decrease is preferable at least 10%, such as at least 20%, preferable at least 30%, such as at least 40%, more preferred at least 50%.

In one embodiment, the invention relates to an extended release dosage form which when administered once daily in steady state to a healthy subject or a patient, the swing of the blood concentrations for total and/or free tacrolimus measured as $(C_{max}-C_{min})/C_{min}$ is less than the swing observed when administering the Prograf® dosage form or a bioequivalent immediate release composition of tacrolimus in a twice daily regimen and being determined under similar conditions and administered in similar molecular daily dosages of the tacrolimus. The decrease is preferable at least 10%, such as at least 20%, preferable at least 30%, such as at least 40%, more preferred at least 50%.

In one embodiment, the invention relates to an extended release dosage form which when administered once daily in steady state to a healthy subject or a patient, the fluctuation of the blood concentrations for total and/or free tacrolimus measured as $(C_{max}-C_{min})/C_{average}$ is less than the fluctuation observed when administering the Advagraf® dosage form or a bioequivalent extended release dosage form of tacrolimus in a once daily regimen and being determined under similar conditions and administered in similar molecular daily dosages of the tacrolimus. The decrease is preferable at least 10%, such as at least 20%, preferable at least 30%, such as at least 40%, more preferred at least 50%.

In one embodiment, the invention relates to an extended release dosage form which when administered once daily in steady state to a healthy subject or a patient, the fluctuation of the blood concentrations for total tacrolimus measured as $(C_{max}-C_{min})/C_{average}$ is less than the fluctuation observed when administering the Prograf® dosage form or a bioequivalent immediate release composition of tacrolimus in a twice daily regimen and being determined under similar conditions and administered in similar molecular daily dosages of the tacrolimus. The decrease is preferable at least 10%, such as at least 20%, preferable at least 30%, such as at least 40%, more preferred at least 50%.

In one embodiment, the invention relates to an extended release dosage form which when administered to at least 6 healthy subjects in fasted state, the mean residence time, MRT, of tacrolimus measured in blood is at least 10% longer than the mean residence time measured under bioequivalent conditions with the Advagraf® dosage form or a similar extended release dosage form of tacrolimus. Preferable the MRT is increased by at least 20% such as by 25%.

In one embodiment, the invention relates to an extended release dosage form which when administered to at least 6 healthy subjects in fasted state, the mean residence time tacrolimus measured in blood is at least 35% longer than the mean residence time measured under similar conditions with the Prograf® dosage form or a bioequivalent immediate release dosage form of tacrolimus.

In a yet further aspect the present invention provides for a method for providing immunosuppressive treatment of a patient in need thereof in a once daily regimen by administration of an extended release formulation as described herein an providing one or more of decreased $C_{max}$, decreased swing, decreased fluctuation, increased AUC, increased MRT, longer time to $T_{max}$, and a higher $C_{min}$. Additionally, the methods provides for a $C_{min}$ which correlates to the bioavailability with a correlation factor of at least 0.75 to 1, such as at least 0.80, preferably 0.85, more preferred 0.90, still more preferred at least 0.95, and even more preferred of at least 0.97.

In a preferred embedment the difference in bioavailability is substantially independent of the time of the day the dosage is administered. This provides the possibility of a once daily dosage regimen at bedtime or in the evening in addition to the normal morning dosing. However more importantly, the risk of decreased exposure if the patient actually ingest the dosage form on a different time than prescribed and expected (non compliance by the patient), the risk for the patient is decreased for reduced exposure and thereby increased risk of e.g., a transplant rejection.

In a further aspect the invention provides for a conversion form a bid regimen with a higher dosage. One method for such conversion from inter alia Prograf® to once daily regimen is decreasing the daily dosage of the tacrolimus immediate release regimen with between 25% to 50%, such as with between 30% to 40%, preferable with approximately 33%. The reduction is to the extend possible by use of extended release once daily dosage forms selected from 0.5 mg1 mg, 2 mg and 5 mg once daily dosage forms. Accordingly, a conversion ratio of 1:0.66 to 0.80 dependent on the available dosage strengths as mentioned. Furthermore, the present invention relates to a conversion from Advagraf® with a ratio of 1:0.30 to 0.75, such as 1:0.33 to 0.7 according to the available dosage strengths selected from 0.5 mg, 1 mg, 2 mg and 5 mg of the extended release formulations according to the present invention.

An especially important aspect of the invention is the substantial reduced peak concentrations which provide for a decrease in peak concentration related side effects. Such effect can however be difficult to measure due to the inter- and intra-subject variation of the present tacrolimus treatments and the nature of the side effects which are often of a subjective character or may require tissue biopsies to determine. Careful questionnaires and high number of patients will be needed for comparison studies to demonstrate such effect with significance. However, it is contemplated that treatment with a extended release formulation according to the present invention may reduce some possible peak concentration related side effects including side effects of a neurological origin such as tremor and headache.

In a preferred embodiment the decrease in side effect is related to the risk of prolonged QTc interval due to an affect on ventricular repolarization. Other toxicities included which is contemplated to be decreased is development of kidney damage, the development of diabetes as well as development of hypertension.

Especially, the accumulation occurring in some organs may be associated with organ damage, especially as the accumulation or the individual tacrolimus concentration may not decrease during the period with the low blood concentration during the later times of the dosing interval. This lack of clearance from an organ may be related to the high affinity of tacrolimus to that organ overcoming the otherwise expected clearance of such highly vascularized organs. Accordingly, the high peaks of the present available commercial dosage forms may contribute to tacrolimus being accumulated in these organs which organs may comprise as high as nearly 30 times the concentration of the blood in steady state with conventional dosage forms.

De novo transplanted patient may be extremely sensitive to high concentrations due to general bad state of the body, low levels of plasma proteins further increasing the fraction of tacrolimus free to enter the organs. Especially in these patients the high blood concentrations during titration are avoided by use of the dosage form according to the invention which has the potential to decrease the magnitude of accumulation or extending the time before high concentrations are reached in organs where tacrolimus is toxic. Accordingly, the invention also relates to a method of treating patients in risk of organ toxicity form tacrolimus. The organs known to accumulate tacrolimus include the adrenal gland, lung, heart, liver, gastrointestinal tract and kidney. However, according to the present invention it is further believed that the pancreas and especially the islet of Langerhans may be sensitive for high concentrations, especially during the initiation of tacrolimus, whereby the risk of developing diabetes on a later time may be substantially increased. Other organs correlated with toxicity are the central nervous system. Many patients withdraw from treatment due to headache and tremor, side effects which is likely to be decreased with the treatment according to the present invention. Especially tremor is a side effect related to toxic effect on the central nervous system as caused by tacrolimus crossing the blood brain barrier. It is according to the present invention comtemplated that high concentrations may facilitate trapping of tacrolimus in the central nervous system as a higher concentration difference is present over the blood brain barrier when the concentrations is high in the systemic circulation which may result in increased transport into the brain compared with a situation where a steady and lower concentration is provided as with the extended release formulation according to the present invention.

According to a further aspect of the invention, the extended release formulation according to the present invention provides for a treatment safety profile allowing treatment from the time of transplantation as soon as the patient is sufficient well to be treated with an oral formulation. Accordingly, the patient will not need a first titration with a conventional twice daily formulation such as Prograf® followed by a conversion to a treatment according to the present invention, but can initiate the oral immunosuppressive treatment with tacrolimus with a once daily formulation according to the present invention.

In a further embodiment, treatment of de novo transplant patients are provided as the formulation according to the present invention is capable of securing a sufficient systemic exposure even in the first 24 hours after initiation whereby a method of treatment is provided where the same dosage form may used for the initiation of tacrolimus oral treatment as well as for the continuous treatment including maintenance treatment. It is believed that the number of dose corrections may be reduced, the compliance will be increased due to the once daily treatment of the present invention with a tablet formulation of reduced size compared with other available tacrolimus products.

It is observed that the use of Advagraf® in the first 24 hours provides a systemic exposure which is approximately 30% and 50% lower when compared with administration of the Prograf® formulation administered to de novo kidney and de novo liver transplant patients, respectively. The general explanation for this reduced bioavailability is according to the Scientific Discussion as disclosed in connection with the approval of Advagraf® by the European Agency for the Evaluation of Medicinal Products (EMEA) at 23 Apr. 2007 attributed to an absence of diurnal effect on the absorption of tacrolimus for Prograf® formulation administered in the evening relative to the morning on the first day post-transplant. However, according to the present inventors, the lower exposure of the Advagraf® product may primarily be related to a relative higher impact of the gastrointestinal metabolism possibly in combination with a lower absorption rate which facilitates a higher first passage extraction fraction by the liver. In liver transplant patients the GI metabolism may have even higher impact as the liver metabolism may be reduced early after transplantation. Accordingly, by providing an extended formulation according to the present invention, the impact of the GI metabolism is less as the formulation primarily releases tacrolimus in the lower ileum and colon where metabolism is less and at the same time releases tacrolimus in a way that absorption actually takes place, i.g releasing the tacrolimus in a improved way such as in molecular form or substantially molecular form.

Accordingly, a method for initial treatment of a de novo liver transplant patient with tacrolimus is provided comprising administering a tacrolimus oral dosage form once a day having an extended release profile which when measured in vitro demonstrates a release where less than 50% of the tacrolimus content in the oral dosage form is released after 10 hours measured according to the dissolution method disclosed for Program by the FDA database of Dissolution Methods For Drug Products and the oral dosage form provides a systemic exposure on day 1 which is at least 50% of the exposure obtained at day 1 after administration of the same daily dose however administered as an immediate release oral dosage form administered twice a day.

Similarly, a method for initial treatment of a de novo kidney transplant patient with tacrolimus comprising administering a tacrolimus oral dosage form once a day having an extended release profile which when measured in vitro demonstrates a release where less than 50% of the tacrolimus content in the oral dosage form is released after 10 hours measured according to the FDA method for Prograf® and the oral dosage form provides a systemic exposure on day 1 which is at least 70% of the exposure obtained at day 1 after administration of the same daily dose however administered as an immediate release oral dosage form administered twice a day.

The method also related to initial treatment of a de novo liver transplant patient with tacrolimus comprising administering a tacrolimus oral dosage form once a day having an extended release profile which when measured in vitro demonstrates a release where less than 50% of the tacrolimus content in the oral dosage form is released after 10 hours measured according to the FDA method for Prograf® and the oral dosage form provides a systemic exposure on day 1 which is at least 100% of the exposure obtained at day 1 after administration of the same daily dose however administered as an extended release oral dosage form releasing more than 30% of the tacrolimus within 5 hours.

Similarly a method for initial treatment of a de novo kidney transplant patient with tacrolimus is provided comprising administering a tacrolimus oral dosage form once a day having an extended release profile which when measured in vitro demonstrates a release where less than 50% of the tacrolimus content in the oral dosage form is released after 10 hours measured according to FDA method for Prograf® and the oral dosage form provides a systemic exposure on day 1 which is at least 100% of the exposure obtained at day 1 after administration of the same daily dose however administered as an extended release oral dosage form releasing more than 30% of the tacrolimus within 5 hours.

A solid dosage form according to the invention may also be coated in order to obtain suitable properties e.g. with respect to controlled release of the active substance. The coating may be applied on single unit dosage forms (e.g. tablets, capsules) or it may be applied on a poly-depot dosage form or on its individual units.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, glyceryl monostearate, zein.

Plasticizers and other ingredients may be added in the coating material. The same or different active substance may also be added in the coating material.

In preferred embodiments of the invention, the solid dosage forms are designed to release tacrolimus and/or an analogue thereof in a controlled manner. In the present context, the term "controlled manner" is intended to include all types of release which differ from the release obtained from plain tablets. Thus, the term includes so-called "controlled release", "extended release", "sustained release", "pulsed release", "prolonged release", burst release", "slow release", "extended release", as well as the terms "delayed release" and pH dependant release. However, a specific aspect of the invention relates to a delayed release composition or dosage form, which in this context is intended to denote a composition or dosage form that at the most releases 10% w/w of the active substance within the first 2 hours after administration and/or after start of a dissolution test employing a dissolution medium having a pH of at the most about 3.

Extended Release Systems

A first extended release system includes matrix systems, in which tacrolimus is embedded or dispersed in a matrix of another material that serves to retard the release of tacrolimus into an aqueous environment (i.e., the luminal fluid of the GI tract). When tacrolimus is dispersed in a matrix of this sort, release of the drug takes place principally from the surface of the matrix. Thus the drug is released from the surface of a device, which incorporates the matrix after it diffuses through the matrix or when the surface of the device erodes, exposing the drug. In some embodiments, both mechanisms can operate simultaneously. The matrix systems may be large, i.e., tablet sized (about 1 cm), or small (<0.3 cm). The system may be unitary (e.g., a bolus), may be divided by virtue of being composed of several sub-units (for example, several capsules which constitute a single dose) which are administered substantially simultaneously, or may comprise a plurality of particles, also denoted a multiparticulate. A multiparticulate can have numerous formulation applications. For example, a multiparticulate may be used as a powder for filling a capsule shell, or used per se for mixing with food to ease the intake.

In a specific embodiment, a matrix multiparticulate, comprises a plurality of tacrolimus-containing particles, each particle comprising tacrolimus and/or an analogue thereof e.g. in the form of a solid solution/dispersion with one or more excipients selected to form a matrix capable of controlling the dissolution rate of the tacrolimus into an aqueous medium. The matrix materials useful for this embodiment are generally hydrophobic materials such as waxes, some cellulose derivatives, or other hydrophobic polymers. If needed, the matrix materials may optionally be formulated with hydrophobic materials, which can be used as binders or as enhancers. Matrix materials useful for the manufacture of these dosage forms such as: ethylcellulose, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble or hydrophilic binders or release modifying agents which can optionally be formulated into the matrix include hydrophilic polymers such as hydroxypropyl cellulose (HPC), hydroxypropyl methyl cellulose (HPMC), methyl cellulose, poly (N-vinyl-2-pyrrolidinone) (PVP), poly(ethylene oxide) (PEO), poly(vinyl alcohol) (PVA), xanthan gum, carrageenan, and other such natural and synthetic materials. In addition, materials, which function as release-modifying agents include water-soluble materials such as sugars or salts. Preferred water-soluble materials include lactose, sucrose, glucose, and mannitol, as well as hydrophillic polymers like e.g. HPC, HPMC, and PVP.

In a specific embodiment, a multiparticulate product is defined as being processed by controlled agglomeration. In this case tacrolimus is dissolved or partly dissolved in a suitable meltable carrier and sprayed on carrier particles comprising the matrix substance.

Suitable Meltable Carriers are Mentioned Previously Herein.

Alternatively, tacrolimus is dissolved in an organic solvent together with the matrix substance and spray dried or applied to carrier particles, cf. below. Solvents typically employed for the process include acetone, ethanol, isopropanol, ethyl acetate, and mixtures of two or more.

Once formed, tacrolimus matrix multiparticulates may be blended with compressible excipients such as lactose, microcrystalline cellulose, dicalcium phosphate, and the like and the blend compressed to form a tablet. Disintegrants such as sodium starch glycolate or crosslinked poly(vinyl pyrrolidone) are also usefully employed. Tablets prepared by this method disintegrate when placed in an aqueous medium (such as the GI tract), thereby exposing the multiparticulate matrix, which releases tacrolimus therefrom.

In a further embodiment, the matrix system is in the form of a hydrophilic matrix tablet containing tacrolimus and/or an analogue thereof (e.g. in the form of a solid dispersion) as a multiparticulate product and an amount of hydrophilic polymer sufficient to provide a useful degree of control over the tacrolimus dissolution. Hydrophilic polymers useful for forming the matrix include hydroxypropylmethyl cellulose (HPMC), hydroxypropyl cellulose (HPC), poly (ethylene oxide), poly(vinyl alcohol), xanthan gum, carbomer, carrageenan, and zooglan. A preferred material is HPMC. Other similar hydrophilic polymers may also be employed. In use, the hydrophilic material is swollen by, and eventually dissolves in, water. The tacrolimus is released both by diffusion from the matrix and by erosion of the matrix. The tacrolimus dissolution rate of these hydrophilic matrix tablets may be controlled by the amount, molecular weight and gel strengths of the hydrophilic polymer employed. In general, using a greater amount of the hydrophilic polymer decreases the dissolution rate, as does using a higher molecular weight polymer. Using a lower molecular weight polymer normally increases the dissolution rate. A matrix tablet typically comprises about 20 to 90% by weight of tacrolimus and about 80 to 10% by weight of polymer.

A preferred matrix tablet comprises, by weight, about 30% to about 80% solid dispersion containing tacrolimus and/or an analogue thereof about 15% to about 35% matrix former (such as, e.g., HPMC), 0% to about 35% lactose, 0% to about 20% microcrystalline cellulose, and about 0.25% to about 2% lubricant (such as, e.g., magnesium stearate).

The matrix systems as a class often exhibit non-constant release of the drug from the matrix. This result may be a consequence of the diffusive mechanism of drug release, and modifications to the geometry of the dosage form can be used with advantage to make the release rate of the drug more constant.

A second class of tacrolimus controlled-release dosage forms of this invention includes membrane-moderated or reservoir systems. In this class, a reservoir of tacrolimus e.g. in a solid solution/dispersion as a multiparticulate product is surrounded by a rate-limiting membrane. The tacrolimus traverses the membrane by mass transport mechanisms well known in the art, including but not limited to dissolution in the membrane followed by diffusion across the membrane or diffusion through liquid-filled pores within the membrane. These individual reservoir system dosage forms may be large, as in the case of a tablet containing a single large reservoir, or multiparticulate, as in the case of a capsule or poly-depot tablets containing a plurality of reservoir particles, each individually coated with a membrane. The coating can be non-porous, yet permeable to tacrolimus (for example tacrolimus may diffuse directly through the membrane), or it may be porous. As with other embodiments of this invention, the particular mechanism of transport is not believed to be critical.

Sustained release coatings as known in the art may be employed to fabricate the membrane, especially polymer coatings, such as a cellulose ester or ether, an acrylic polymer, or a mixture of polymers. Preferred materials include ethyl cellulose, cellulose acetate and cellulose acetate butyrate. The polymer may be applied as a solution in an organic solvent or as an aqueous dispersion or latex. The coating operation may be conducted in standard equipment such as a fluid bed coater, a Wurster coater, or a rotary fluid bed coater.

If desired, the permeability of the coating may be adjusted by blending of two or more materials. A particularly useful process for tailoring the porosity of the coating comprises adding a pre-determined amount of a finely-divided water-soluble material, such as sugars or salts or water-soluble polymers to a solution or dispersion (e.g., an aqueous latex) of the membrane-forming polymer to be used. When the dosage form is ingested into the aqueous medium of the GI tract, these water soluble membrane additives are leached out of the membrane, leaving pores which facilitate release of the drug. The membrane coating can also be modified by the addition of plasticizers, as known in the art.

A particularly useful variation of the process for applying a membrane coating comprises dissolving the coating polymer in a mixture of solvents chosen such that as the coating dries, a phase inversion takes place in the applied coating solution, resulting in a membrane with a porous structure.

In general, a support for mechanically strengthening the membrane is not required.

The morphology of the membrane is not of critical importance so long as the permeability characteristics enumerated herein are met. The membrane can be amorphous or crystalline. It can have any category of morphology produced by any particular process and can be, for example, an interfacially-polymerized membrane (which comprises a thin rate-limiting skin on a porous support), a porous hydrophilic membrane, a porous hydrophobic membrane, a hydrogel membrane, an ionic membrane, and other such materials which are characterized by controlled permeability to tacrolimus.

In one embodiment of the invention it is an aim to reduce the exposure of the upper GI tract to high concentrations of tacrolimus. Accordingly, suitable dosage forms include those forms, which incorporate a specific delay before the onset of controlled release of tacrolimus. An exemplary embodiment can be illustrated by a tablet (or a particulate material) comprising a core containing tacrolimus coated with a first coating of a polymeric material of the type useful for sustained release of tacrolimus and a second coating of the type useful for delaying release of drugs when the dosage form is ingested. The first coating is applied over and surrounds the tablet or individual particles. The second coating is applied over and surrounds the first coating.

A tablet can be prepared by techniques well known in the art and contains a therapeutically useful amount of tacrolimus plus such excipients as are necessary to form the tablet by such techniques.

The first coating may be a sustained release coating as known in the art, especially polymer coatings, to fabricate the membrane, as previously discussed for reservoir systems, or it could be a controlled release matrix core, which are coated a second time with a delayed release material.

Materials useful for preparing the second coating on the tablet include polymers known in the art as enteric coatings for delayed-release of pharmaceuticals. These most commonly are pH-sensitive materials such as cellulose acetate phthalate, cellulose acetate trimellitate, hydroxypropyl methyl cellulose phthalate, poly (vinyl acetate phthalate), and acrylic copolymers such as Eudragit L-100 (Röhm Pharma) and related materials, as more fully detailed below under "Delayed Release". The thickness of the delayed-release coating is adjusted to give the desired delay property. In general, thicker coatings are more resistant to erosion and, consequently, yield a longer and more effective delay. Preferred coatings range from about 30 μm in thickness to about 3 mm in thickness.

When using a hydrophobic matrix material like glyceryl monostearate, no delay coating is necessary. The tablet will not release tacrolimus until an area of enzymatic degradation has been reached, more specifically after the duodenum.

When ingested, the twice-coated tablet passes through the stomach, where the second coating prevents release of the tacrolimus under the acidic conditions prevalent there. When the tablet passes out of the stomach and into the small intestine, where the pH is higher, the second coating erodes or dissolves according to the physicochemical properties of the chosen material. Upon erosion or dissolution of the second coating, the first coating prevents immediate or rapid release of the tacrolimus and modulates the release so as to prevent the production of high peak concentrations, thereby minimizing side-effects.

A further preferred embodiment comprises a multiparticulate wherein each particle is dual coated as described above for tablets, first with a polymer designed to yield sustained release of the tacrolimus and then coated with a polymer designed to delay onset of release in the environment of the GI tract when the dosage form is ingested.

The rate of tacrolimus release from the sustained-release-coated multiparticulates (i.e., the multiparticulates before they receive the delayed-release coating) and methods of modifying the coating are also controlled by the factors previously discussed for reservoir system tacrolimus multiparticulates.

The second membrane or coating for dual coated multiparticulates is a delayed-release coating which is applied over the first sustained-release coating, as disclosed above for tablets, and may be formed from the same materials. It should be noted that the use of the so-called "enteric" materials to practice this embodiment differs significantly from their use to produce conventional enteric dosage forms. With conventional enteric forms, the object is to delay release of the drug until the dosage form has passed the stomach and then to deliver the dose in the duodenum. Dosing of tacrolimus directly and completely to the duodenum may be undesirable, however, due to the side effects sought to be minimized or avoided by this invention. Therefore, if conventional enteric polymers are to be used to practice this embodiment, it may be necessary to apply them significantly more thickly than in conventional practice, in order to delay drug release until the dosage form reaches the lower GI tract. However, it is also possible to effect a sustained or controlled delivery of tacrolimus after the delayed-release coating has dissolved or eroded, therefore the benefits of this embodiment may be realized with a proper combination of delayed-release character with sustained-release character, and the delayed-release part alone may or may not necessarily conform to USP enteric criteria. The thickness of the delayed-release coating is adjusted to give the desired delay property. In general, thicker coatings are more resistant to erosion and, consequently, yield a longer delay.

A first delayed release embodiment according to the invention is a "pH-dependent coated dosage form" such as, e.g., a tablet or a capsule. In the case of a tablet it comprises a tablet core comprising tacrolimus e.g. in a solid solution/dispersion as a multiparticulate product, a controlled release matrix of e.g. HPMC, a disintegrant, a lubricant, and one or more pharmaceutical carriers, such core being coated with a material, preferably a polymer, which is substantially insoluble and impermeable at the pH of the stomach, and which is more soluble and permeable at the pH of the small intestine. Preferably, the coating polymer is substantially insoluble and impermeable at pH<5.0, and water-soluble at pH>5.0. The tablet core may be coated with an amount of polymer sufficient to assure that substantially no release of tacrolimus from the dosage form occurs until the dosage form has exited the stomach and has resided in the small intestine for about 15 minutes or greater, preferably about 30 minutes or greater, thus assuring that minimal tacrolimus is released in the duodenum. Mixtures of a pH-sensitive polymer with a water-insoluble polymer may also be employed. Tablets are coated with an amount of polymer comprising from about 10% to about 80% of the weight of the tacrolimus-containing tablet core. Preferred tablets are coated with an amount of polymer comprising about 15% to about 50% of the weight of the tacrolimus tablet core.

pH-sensitive polymers which are very insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

The delay time before release of tacrolimus, after the "pH-dependent coated tablet" dosage form has exited the stomach, may be controlled by choice of the relative amounts of Eudragit-L® and Eudragit-S® in the coating, and by choice of the coating thickness. Eudragit-L® films dissolve above pH 6.0, and Eudragit-S® films dissolve above 7.0, and mixtures dissolve at intermediate pH's. Since the pH of the duodenum is approximately 6.0 and the pH of the colon is approximately 7.0, coatings composed of mixtures of Eudragit-L® and Eudragit-S® provide protection of the duodenum from tacrolimus. If it is desired to delay release of tacrolimus until the tacrolimus-containing "pH-dependent coated tablet" has reached the colon, Eudragit-S® may be used as the coating material, as described by Dew et al. (Br. J. Clin. Pharmac. 14 (1982) 405-408). In order to delay the release of tacrolimus for about 15 minutes or more, preferably 30 minutes or more, after the dosage form has exited the stomach, preferred coatings comprise from about 9:1 to about 1:9 Eudragit-L®/Eudragit-S®, more preferably from about 9:1 to about 1:4 Eudragit-L®/Eudragit-S®. The coating may comprise from about 3% to about 70% of the weight of the uncoated tablet core. Preferably, the coating comprises from about 5% to about 50% of the weight of the tablet core.

Uses

A solid dispersion and/or solution may be used for the preparation of an extended release solid oral dosage form such as tablets, capsules or sachets; or for the preparation of granules, pellets microspheres or nanoparticles.

A further advantage of the extended release dosage form of the present invention is the possibility of obtaining an effective therapeutic response with a decreased dosage compared to traditional oral treatment. Thus it is contemplated that the solid dosage form of the invention, when orally administered to a mammal in need thereof in a dose that is at the most about 85% w/w such as, e.g., at the most about 80% w/w, at the most about 75%, at the most about 70% w/w, at the most about 65% w/w, at the most about 60% w/w, at the most about 55% w/w or at the most about 50% w/w of the dose of tacrolimus administered in the form of Prograf® or a similar commercially available tacrolimus-containing product, is essentially bioequivalent with Prograf® or a similar commercially available tacrolimus-containing product.

Any of the tacrolimus-containing dosage forms, compositions, dispersions or solutions of the invention may improved treatment of conditions that respond to tacrolimus treatment.

Tacrolimus is indicated (or has been suggested) for the treatment of diseases such as, e.g., rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.; graft-versus-host reactions following bone marrow transplantation; autoimmune diseases such as rheumatoid arthritis, systemic lupus erythematosus, Hashimoto's thyroiditis, multiple sclerosis, myasthenia gravis, type I diabetes, etc.; infections caused by pathogenic microorganisms (e.g. *Aspergillus fumigatus, Fusarium oxysporum, Trichophyton* asteroides, etc.); inflammatory or hyperproliferative skin diseases or cutaneous manifestations of immunologically mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata); autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.); reversible obstructive airways diseases (asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.; mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases); intestinal inflammations/allergies (e.g. coeliac diseases, proctitis, eosinophilic gastroenteritis, mastocytosis, Crohn's disease and ulcerative colitis); food-related allergic diseases with symptomatic manifestation remote from the gastrointestinal tract (e.g. migrain, rhinitis and eczema); renal diseases (e.g. intestitial nephritis, Goodpasture's syndrome, hemolytic uremic syndrome, and diabetic nephropathy); nervous diseases (e.g. multiple myositis, Guillain-Barre syndrome, Meniere's disease, multiple neuritis, solitary neuritis, cerebral infarction, Alzheimer's diseases Parkinson's diseases, amyotrophic lateral sclerosis (ALS) and radiculopathy); cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction); endocrine diseases (e.g. hyperthyroidism, and Basedow's disease); hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia); bone diseases (e.g. osteoporosis); respiratory diseases (e.g. sarcoidosis, pulmonary fibrosis, and idiopathic interstitial pneumonia); skin diseases (e.g. dermatomyositis, leukoderma vulgaris, ichthyosis vulgaris, photosensitivity, and cutaneous T-cell lymphoma); circulatory diseases (e.g. arteriosclerosis, atherosclerosis, aortitis syndrome, polyarteritis nodosa, and myocardosis); collagen diseases (e.g. scleroderma, Wegener's granuloma, and Sjogren's syndrome); adiposis; eosinophilic fasciitis; periodontal diseases (e.g. damage to gingiva, periodontium, alveolar bone or substantia ossea dentis); nephrotic syndrome (e.g. glomerulonephritis); male pattern alopecia, alopecia senile; muscular dystrophy; pyoderma and Sezary syndrome; chromosome abnormality-associated diseases (e.g. Down's syndrome); Addison's disease; active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)); intestinal diseases (e.g. endotoxin shock, pseudomembranous colitis, and drug- or radiation-induced colitis); renal diseases (e.g. ischemic acute renal insufficiency, chronic renal failure); pulmonary diseases (e.g. toxicosis caused by pulmonary oxygen or drugs (e.g. paracort, bleomycin, etc.), lung cancer, and pulmonary emphysema); ocular diseases (e.g. cataracta, iron-storage disease (siderosis bulbi), retinitis, pigmentosa, senile plaques, vitreous scarring, corneal alkali burn); dermatitis (e.g. erythema multiforme, linear immunoglobulin A bullous dermatitis, cement dermatitis); and other diseases (e.g. gingivitis, periodontitis, sepsis, pancreatitis, and diseases caused by environmental pollution (e.g. air pollution), aging, carcinogen, metastasis of carcinoma, and hypobaropathy)]; diseases caused by histamine release or leukotriene C4 release; restenosis of coronary artery following angioplasty and prevention of postsurgical adhesions; autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis); Human Immunodeficiency Virus (HIV) infection, AIDS; allergic conjunctivitis; hypertrophic cicatrix and keloid due to trauma, burn, or surgery.

In addition, tricyclic macrolides like e.g. tacrolimus have liver regenerating activity and/or activities of stimulating hypertrophy and hyperplasia of hepatocytes. Therefore, the extended release dosage form of the present invention is useful for increasing the effect of the therapy and/or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

Furthermore, a extended release dosage form according to the present invention is useful for increasing the effect of the prevention and/or treatment of various diseases because of the useful pharmacological activity of the tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity and so on.

The present invention is further illustrated by reference to the Examples below. However, it should be noted that these Examples, like the embodiments described above, are illustrative and are not to be construed as restricting the enabled scope of the invention in any way.

EXAMPLES

Materials and Methods
Materials
Tacrolimus (supplied by Eurotrade); batch no RD 03-111
Lactose monohydrate 200 mesh (from DMV)
Granulated silicium oxide, Aeroperl® 300, (Degussa)
Polyethylene glycol 6000, Pluracol® E6000 (from BASF)
Poloxamer 188, Pluronic® F-68 (from BASF)
Glyceryl monostearate, Rylo® MD50, (from Danisco Cultor), Ph.Eur.; batch no. 4010056276
Avicel PH200 (microcrystalline cellulose) (from FMC)
Lactose DCL 11 (from DMV)
Magnesium stearate
Croscarmellose sodium, Ac-Di-Sol® (from FMC)
Eudragit® L30D.55 (from Degussa)
Triethyl citrate (from Merck)
Anti-foam emulsion (from Unikem)
Micro talc
HPMC refers to Metolose 90SH (type 2910, 2208) or Metolose 60SH (type 2910) from ShinEtsu available in various degrees of polymerization (viscosity 3-100,000 cP).

Tablets, capsules or granules might be enteric coated with different types of polymers such as hydroxypropylmethylcellulose acetate succinate (Aqoat), cellulose acetate phtalate CAP, hydroxypropylmethylcellulose phtalate HPMCP or methacrylic acid copolymers such as Eudragit L30D, Eudragit 100/S, Eudragit 100/L.
Comparison Prior Art Tacrolimus Formulation for In Vivo Studies:
Prograf© Hard Gelatin Capsules, manufactured by Fujisawa Ireland Ltd.

| Ingredients | mg |
| --- | --- |
| Tacrolimus, anhydr. | 1.0 |
| Gelatin | 6.9 |
| Hypromellose | 1.0 |
| Lactose monohydrate | 24.7 |
| Magnesium stearate | 0.3 |
| Shellac | q.s. |
| Soybean lecitine | q.s. |
| Iron oxide red (E172) | q.s. |
| Titanium dioxide (E171) | q.s. |
| Dimeticone (E900) | q.s. |

Methods
Determination of Weight Variation
The tablets prepared in the Examples herein were subjected to a test for weight variation performed in accordance with Ph. Eur.

Determination of Average Tablet Hardness

The tablets prepared in the Examples herein were subjected to at test for tablet hardness employing Schleuniger Model 6D apparatus and performed in accordance with the general instructions for the apparatus.

Determination of Disintegration Time

The time for a tablet to disintegrate, i.e. to decompose into particles or agglomerates, was determined in accordance with Ph. Eur.

Determination of Geometric Weight Mean Diameter $d_{gw}$

The geometric weight mean diameter was determined by employment of a method of laser diffraction dispersing the particulate material obtained (or the starting material) in air. The measurements were performed at 1 bar dispersive pressure in Sympatec Helos equipment, which records the distribution of the equivalent spherical diameter. This distribution is fitted to a log normal volume-size distribution.

When used herein, "geometric weight mean diameter" means the mean diameter of the log normal volume-size distribution.

In Vitro Dissolution Tests

The following test methods were applies to the compositions and dosage forms of the present invention.

Test 1:

In vitro dissolution test according to USP Method A, delayed release articles (USP paddle method; rotation speed: 50 rpm; 37° C.; after 2 hours in acidic medium, the medium is changed to phosphate buffer pH 6.8.).

Test 2:

In vitro dissolution test in aqueous dissolution medium adjusted to pH 4.5 (900 ml water with 0.005% HPC (hydroxypropylcellulose) adjusted to pH4.5; 37° C.; USP Paddle method; rotation speed: 50 rpm).

The following examples serve the purpose of illustration of the invention and are not intended to limiting the scope of the present invention.

Pharmaceutical compositions and dosage forms which can be optimized to provide the desired release profile according to the invention is exemplified in examples 1-16 which formulations are disclosed in the patent application WO 2005/020993 hereby incorporated by reference. The dissolution profiles disclosed therein and in Example 17 of the present application may however be further optimized for providing release profiles fulfilling the extended release parameters according to the present invention. The optimization may include formulation changes including changes in grades of excipients, change in ratios of excipients, manufacturing changes such as change in punch pressure, change in hardness or disintegration time. As a molecular solution is preferred, relevant changes includes use of excipients preventing degradation of the active substance as well as use of specific excipients less prone to interact with the active substance and/or degradation products thereof.

Example 1

Modified Release Poly-Depot Capsule Based on Swelling Hydrocolloid Matrix of Hydroxypropylcellulose

| Substance | % | mg |
|---|---|---|
| Tacrolimus | 0.50 | 1.00 |
| HPMC | 20.00 | 40.00 |
| Lactose 200 mesh | 30.00 | 60.00 |
| PEG 6000 | 34.65 | 69.30 |
| Poloxamer 188 | 14.85 | 29.70 |
| Total | 100.00 | 200.00 |

Tacrolimus was dissolved in polyethylene glycol 6000 and poloxamer 188 (70:30 w/w ratio) at 70° C. The solution was sprayed on a mixture of 150 g lactose and 100 g HPMC in a fluid bed Strea-1. The granular product was sieved through sieve 0.7 mm and filled into hard gelatine capsules (200 mg).

Example 2

Modified Release Poly-Depot Capsule Based on Swelling Hydrocolloid Matrix of Hydroxypropylcellulose

| Substance | % | mg |
|---|---|---|
| Tacrolimus | 0.50 | 1.00 |
| HPMC 2910 3 cp | 20.00 | 40.00 |
| Lactose 200 mesh | 30.00 | 60.00 |
| Glyceryl monostearate | 49.50 | 99.00 |
| Total | 100.00 | 200.00 |

Tacrolimus was dissolved in glyceryl monostearate at 70° C. The solution was sprayed on a mixture of 150 g lactose and 100 g HPMC in a fluid bed Strea-1. The granular product was sieved through sieve 0.7 mm and filled into hard gelatine capsules (200 mg).

Example 3

Extended Release Matrix Tablet Based on Swelling Hydrocolloid Matrix of Hydroxypropylcellulose

| Substance | % | mg |
|---|---|---|
| Tacrolimus | 0.50 | 1.00 |
| HPMC | 19.90 | 40.00 |
| Lactose 200 mesh | 29.85 | 60.00 |
| PEG 6000 | 34.48 | 69.30 |
| Poloxamer 188 | 14.78 | 29.70 |
| Magnesium stearate | 0.50 | 1.01 |
| Total | 100.00 | 201.01 |

Tacrolimus was dissolved in polyethylene glycol 6000 and poloxamer 188 (70:30 w/w ratio) at 70° C. The solution was sprayed onto 250 g lactose in a fluid bed Strea-1. The resulting granular product was sieved through sieve 0.7 mm and blended with HPMC and magnesium stearate for 0.5 min in a Turbula mixer.

The mixture was compressed into 8 mm tablets of 1 mg active ingredient (200 mg tablet) with compound cup shaped.

Mean disintegration time: 20 min. Hardness: 45 N

Example 4

Modified Release Matrix Tablet Based on Lipophilic Matrix of Glyceryl Monostearate

| Substance | % | mg |
|---|---|---|
| Tacrolimus | 0.50 | 1.00 |
| Lactose 200 mesh | 49.75 | 100.00 |
| Glyceryl monostearate | 49.25 | 99.00 |
| Magnesium stearate | 0.50 | 1.01 |
|  | 100.00 | 201.01 |

Tacrolimus was dissolved in glyceryl monostearate at 70° C. The solution was sprayed onto 250 g lactose in a fluid bed Strea-1. The granular product was sieved through sieve 0.7 mm and blended with magnesium stearate for 0.5 minutes in a Turbula mixer.

The resulting mixture was compressed into 8 mm tablets of 1 mg active ingredient (200 mg tablet) with compound cup shape.

Mean disintegration time: 20 min. Hardness: 45 N

Example 5

Modified Release Polydepot Capsule Based on Lipophilic Matrix of Glyceryl Monostearate

| Substance | % | mg |
| --- | --- | --- |
| Tacrolimus | 0.50 | 1.00 |
| Lactose 200 mesh | 49.75 | 100.00 |
| Glyceryl monostearate | 49.25 | 99.00 |
| Magnesium stearate | 0.50 | 1.01 |
| | 100.00 | 201.01 |

Tacrolimus was dissolved in glyceryl monostearate at 70° C. The solution was sprayed onto 250 g lactose in a fluid bed Strea-1. The granular product was sieved through sieve 0.7 mm and filled into hard gelatine capsules (200 mg).

Example 6

Modified Release Poly-Depot Tablet Based on Lipophilic Matrix of Gelucire® 44/14

| Substance | % | mg |
| --- | --- | --- |
| Tacrolimus | 0.50 | 1.00 |
| Aeroperl® 300 | 49.75 | 100.00 |
| Gelucire® 44/14 | 49.25 | 99.00 |
| Magnesium stearate | 0.50 | 1.01 |
| | 100.00 | 201.01 |

Tacrolimus was dissolved in Gelucire® at 70° C. The solution was sprayed onto 250 g Aeroperl® in a fluid bed Strea-1. The granular product was sieved through sieve 0.7 mm and filled into hard gelatine capsules (200 mg).

The resulting granulate was compressed into 8 mm tablets of 1 mg active ingredient (tablet weight 200 mg). Tablets were cup shaped.

Mean disintegration time: 25 minutes. Hardness: 43 N.

Example 7

Enteric Coating

Capsules and tablets of examples 1, 2, 3, 5 and 6 were subsequently coated with the following enteric coating in order to obtain a delayed release of active ingredient after administration.

| Ingredients | % |
| --- | --- |
| Eudragit® L30D | 40 |
| Purified water | 52 |
| Triethyl acetylcitrate | 1.8 |
| Anti-foam emulsion | 0.2 |
| Talc | 6 |
| Total | 100 |

The coating suspension was prepared by mixing triethyl acetylcitrate, antifoam emulsion and purified water in Ultra Turrax apparatus at 9500 rpm for 30 min. After 1 minute talc was added. The mixture was passed through sieve no. 300 and stirred by a magnet stirrer. Eudragit was passed through sieve no. 300 and added the mixture, which was stirred for 5 minutes.

The process conditions of the coating process were the following an inlet temperature of 40° C., an outlet temperature of 31° C., air inlet of 140 cbm per hour and a coating time of approx. 50 minutes (300 g of coating material). Approximately 400 g of tablets, or 200 g of capsules were coated.

The film coated tablets and capsules were cured for 48 hours at 30° C. before dissolution testing.

Example 8

Modified Release Matrix Tablet Based on Lipophilic Matrix of Glycerol Monostearate

| Substance | % | mg |
| --- | --- | --- |
| Tacrolimus | 0.95 | 2.00 |
| HPMC, Pharmacoat 606 | 6.75 | 14.29 |
| Lactose monohydrate, lactose 125 mesh | 6.75 | 14.29 |
| Glycerol monostearate, Rylo® MD50 | 30.56 | 64.67 |
| Magnesium Stearate | 0.5 | 1.06 |
| Talc | 4.5 | 9.52 |
| Lactose monohydrate, Pharmatose DCL 14 | 50.00 | 105.8 |
| | 100.00 | 211.64 |

Tacrolimus was dissolved in glycerol monostearate at a temperature above 80° C. The solution was sprayed by feed unit Phast FS1.7 onto 60 g lactose and 60 g HPMC in a fluid bed Phast FB100. The granular product was hardened in a heating oven for 4 hours at 50° C. The resulting granular product was sifted through sieve 0.71 mm and blended with lactose for 3 minutes in a Turbula mixer.

Magnesium stearate and talc was sifted through sieve no. 300 and mixed in a Turbula mixer for 3 minutes. The granulate was mixed with the mixture of magnesium stearate and talc (1:9) for 0.5 minutes in a Turbula mixer.

The final mixture was compressed into 8 mm tablets of 2 mg active ingredient (210 mg tablet) with compound cup shape.

Mean disintegration time: 2 hours. Hardness: 50 N

Example 9

Enteric Coated Tablet with Core Based on PEG 6000/Poloxamer 188 and Enteric Coating Based on Eudragit L30D 55

Tablet core composition:

| Substance | % | mg |
| --- | --- | --- |
| Tacrolimus | 1.98 | 2.00 |
| Lactose monohydrate, Lactose 200 mesh | 40.50 | 40.91 |
| PEG 6000 | 33.26 | 33.60 |
| Poloxamer 188, Lutrol 68 | 14.40 | 14.40 |
| Magnesium Stearate | 0.50 | 0.51 |
| Talc | 4.50 | 4.55 |
| Croscarmellose sodium, Ac-di-sol | 5.00 | 5.05 |
| | 100.00 | 101.01 |

The tacrolimus tablet core was produced by dissolving in PEG 6000 at a temperature above 80° C. Poloxamer 188 was added, and the solution was heated to a temperature above 80° C. The solution was sprayed by feed unit Phast FS1.7 on 200 g lactose monohydrate in a fluid bed Phast FB100. The resulting granulate was sifted through a Comill sieve 1397, 4500 rpm, and blended with croscarmellose sodium for 3 minutes in a Turbula mixer.

Magnesium stearate and talc was sifted through sieve no. 300 and mixed in a Turbula mixer for 3 minutes. The granulate was mixed with magnesium stearate and talc (1:9) for 0.5 minutes in a Turbula mixer.

The resulting mixture was compressed into 6 mm tablets of 2 mg active ingredient (100 mg tablet) with compound cup shape.

Mean disintegration time: 7 minutes. Hardness: 65 N
Enteric Coating:

The enteric coating is based on an acrylic polymer Eudragit L30D-55. Eudragit L30D is supplied as an aqueous latex suspension creating a water insoluble film when the water is evaporated during coating. The polymer is insoluble at pH-values below 5.0 and readily soluble at pH-values over 6.0. The film coating composition is:

| Substance | w/w % |
|---|---|
| Eudragit L30D-55 | 40 |
| Water | 52 |
| Triethyl citrate | 1.8 |
| Anti-foam emulsion | 0.2 |
| Talc (micro) | 6 |
| Total | 100 |

The amount of applied film polymer (Eudragit) was based on a calculation of mg film polymer per cm² tablet surface. The thickness of the enteric coating was 80 μm. A verification of the film thickness applied was based on measuring the increase in tablet height with a digital micrometer. The film coating process was performed in a Phast FB100 fluid bed equipped with a Wurster like insert. The process conditions were: Inlet air temperature 50° C.; Inlet air flow 100 m³ per hour; Product temperature 38° C.; Feed rate 15 g/min.

After coating, proper film formation requires curing of the coated tablets i.e. at 30° C. for 48 hours in an oven. Alternatively the coated tablets more efficiently could be cured at 40° C. in 24 hours.

Example 10

Controlled Release PEG 6000/Poloxamer 188 Tablet Based on a HPMC Matrix.
Tablet composition:

| Substance | % | mg |
|---|---|---|
| Tacrolimus | 1.21 | 2.00 |
| Lactose monohydrate, Lactose 200 mesh | 24.75 | 40.91 |
| PEG 6000 | 20.33 | 33.60 |
| Poloxamer 188, Lutrol 68 | 8.71 | 14.40 |
| Magnesium Stearate | 0.50 | 0.83 |
| Talc | 4.50 | 7.44 |
| Hydroxypropyl methylcellulose, Metolose 90SH 15000 | 40.00 | 66.12 |
| | 100.00 | 165.29 |

Tacrolimus was dissolved in PEG 6000 at a temperature above 80° C. Poloxamer 188 is added and the solution is heated to a temperature above 80° C. The solution is sprayed by feed unit Phast FS1.7 on 200 g lactose monohydrate in a fluid bed Phast FB100. The granular product is sieved through a Comill, sieve 1397, 4500 rpm, and blended with Hydroxypropyl methylcellulose for 3 min in a Turbula mixer.

Magnesium stearate and talc is sifted through sieve 300 and mixed in a Turbola mixer for 3 min. The granulate is mixed with Magnesium Stearate:Talc (1:9) for 0.5 min in a Turbula mixer. The mixture is compressed into 8 mm tablets with strength of 2 mg (165 mg tablet with compound cup shape). Mean disintegration time: 2 hours 34 minutes, Hardness: 50 N Example 11

Enteric Coated Tablet Formulation. Wet Granulation and Enteric-Coated Tablets
Tablet composition:

| Ingredient | mg |
|---|---|
| Tacrolimus | 2 |
| Lactose | 80 |
| Sodium lauryl sulfate | 10 |
| Kollidon VA64 | 3 |
| Avicel PH200 | 30 |
| Magnesium stearate | 0.5 |
| Total | 125.5 |

The tablet formulation was based on wet granulation in a high shear mixer Pellmix ⅛. 16 g Micronized tacrolimus was mixed with 640 g lactose 125 mesh and 80 g natrium lauryl sulfate in the high shear mixer. A 15% aqueous solution of binder Kollidon VA64 was pumped to the mixture at an impeller speed of 500 rpm at a feed rate of 20 g/min. and subsequently kneaded for 3 minutes at the equal speed. The granulate was dried in a tray dryer and sieved through sieve size 0.7 mm.

The granulate was mixed with 240 g Avicel PH200 for 3 minutes and for and after addition of 4 g magnesium stearate for further 0.5 minute. The mixture was compressed into tablets on a single punch tabletting machine Diaf TM20.

Tablet diameter: 6 mm. Tablet shape: round, compound cup.

The tablets were subsequently coated with an enteric coating of acrylic type as described in example 9.

The amount of applied film polymer (Eudragit) should be based on a calculation of mg film polymer per cm² tablet surface. The thickness of the enteric coating should be 50-80 μm. A verification of the film thickness applied is based on measuring the increase in tablet height with a digital micrometer. The film coating process is performed in a Stre-1 fluid bed equipped with a Wurster insert at the following process conditions:

| Process parameter | Process value |
|---|---|
| Product load, g | 400 |
| Inlet air temperature, ° C. | 40 |
| Inlet air flow, m³ per hour | 140 |
| Outlet air temperature, ° C. | 31 |
| Feed rate g/min | 5 |

After coating, proper film formation requires curing of the coated tablets, i.e. 30° C. in 48 hours in an oven. Alternatively the coated tablets more efficiently could be cured at 40° C. for 24 hours.

Example 12

Controlled Release Tablet Formulation Based on Eroding HPMC Matrix

HPMC added as part of the extragranular phase. Wet granulation.

Tablet composition:

| Ingredients | mg |
| --- | --- |
| Tacrolimus | 2 |
| Lactose | 80 |
| Sodium lauryl sulfate | 10 |
| Kollidon VA64 | 3 |
| Avicel PH200 | 30 |
| Metolose SH 90 | 60 |
| Magnesium stearate | 1 |
| Total | 186 |

The tablet formulation was based on wet granulation in a high shear mixer Pellmix ⅛. 16 g Micronized tacrolimus was mixed with 640 g lactose 125 mesh and 80 g natrium lauryl sulfate in the high shear mixer. A 15% aqueous solution of binder Kollidon VA64 was pumped to the mixture at an impeller speed of 500 rpm at a feed rate of 20 g/min and subsequently kneaded for 3 minutes at equal impeller speed. The granulate was dried in a tray dryer and sieved through sieve size 0.7 mm.

The granulate was mixed with 240 g Avicel PH200 and 480 g hydroxypropylmethylcellulose Metolose SH 90 100 cP for 3 minutes and for and after addition of 8 g magnesium stearate for further 0.5 minute. The mixture was compressed into tablets on a single punch tabletting machine Diaf TM20.

Tablet diameter: 7 mm. Tablet shape: round, compound cup.

Example 13

Controlled Release Tablet Formulation Based on Eroding HPMC Matrix

HPMC added as part of the intragranular phase. Wet granulation.

Tablet composition:

| Ingredient | mg |
| --- | --- |
| Tacrolimus | 2 |
| Lactose | 80 |
| Sodium lauryl sulfate | 10 |
| Metolose SH 90 | 80 |
| Avicel PH200 | 60 |
| Magnesium stearate | 2 |
| Total | 234 |

The tablet formulation was based on wet granulation in a high shear mixer Pellmix ⅛. 16 g Micronized tacrolimus was mixed with 640 g lactose 125 mesh and 80 g natrium lauryl sulfate and 640 g hydroxypropylmethylcellulose Metolose SH 90 15.000 cP in the high shear mixer. Purified water was pumped to the mixture at an impeller speed of 500 rpm at a feed rate of 20 g/min. and subsequently kneaded for 3 minutes. The granulate was dried in a tray dryer and sieved through sieve size 0.7 mm.

The granulate was mixed with 480 g Avicel PH200 for 3 minutes and for and after addition of 16 g magnesium stearate for further 0.5 minute. The mixture was compressed into tablets on a single punch tabletting machine Diaf TM20.

Tablet diameter: 8 mm. Tablet shape: round, compound cup.

Example 14

Controlled Release Tablet Formulation Based on Eroding HPMC Matrix

HPMC added as part of the intragranular phase. Melt granulation

Tablet composition:

| Ingredient | mg |
| --- | --- |
| Tacrolimus | 2 |
| Lactose | 80 |
| PEG 6000 | 15 |
| Poloxamer 188 | 6 |
| Metolose SH 90 | 80 |
| Avicel PH200 | 60 |
| Magnesium stearate | 2 |
| Total | 245 |

The tablet formulation was based on melt granulation in a high shear mixer Pellmix ⅛. 16 g Micronized tacrolimus was mixed with 640 g lactose 125 mesh and 120 g Polyethylene glycol 6000, 48 g Poloxamer 188 and 640 g hydroxypropylmethylcellulose Metolose SH 90 15.000 cP in the high shear mixer. The jacket of the mixer bowl was heated to 80° C. and the blend was heated at an impeller rotation speed of 1000 rpm until melting point of PEG and Poloxamer. After melting the kneading was continued for 4 minutes at 800 rpm. The granulated was sieved through sieve size of 0.7 mm and cooled on a tray. The granulate was mixed with 480 g Avicel PH200 for 3 minutes and for and after addition of 16 g magnesium stearate for further 0.5 minute. The mixture was compressed into tablets on a single punch tabletting machine Diaf TM20. Tablet diameter: 8 mm. Tablet shape: round, compound cup.

Example 15

Controlled Release Tablet Formulation Based on Eroding Kollidon SR Matrix Added as Part of the Extragranular Phase.

Tablet composition:

| Ingredient | mg |
| --- | --- |
| Tacrolimus | 2 |
| Lactose | 80 |
| Sodium lauryl sulfate | 10 |
| Kollidon VA64 | 3 |
| Lactose DC lac14 | 50 |
| Kollidon SR | 60 |
| Magnesium stearate | 1 |
| Total | 206 |

The tablet formulation was based on wet granulation in a high shear mixer Pellmix ⅛. 16 g Micronized tacrolimus was mixed with 640 g lactose 125 mesh and 80 g natrium lauryl sulfate in the high shear mixer. A 15% aqueous solution of binder Kollidon VA64 (Kollidon SR is a mixture of polyvinyl acetate and polyvinylpyrrolidon 80:20) was pumped to the mixture at an impeller speed of 500 rpm at a feed rate of 20 g/min and subsequently kneaded for 3 minutes. The granulate was dried in a tray dryer and sieved through sieve size 0.7 mm. The granulate was mixed with 400 g lactose DC Lac 14 and 480 g Kollidon SR for 3 minutes and for and after addition of 8 g magnesium stearate for further 0.5 minute. The mixture was compressed into tablets on a single punch tabletting machine Diaf TM20.

Tablet diameter: 8 mm. Tablet shape: round, compound cup.

Example 16

Enteric Coated Tablet Formulation (Melt Granulation and Enteric-Coated Tablets)
Tablet composition:

| Ingredient | mg |
| --- | --- |
| Tacrolimus | 2 |
| Lactose | 80 |
| PEG 6000 | 15 |
| Poloxamer 188 | 6 |
| Avicel PH200 | 60 |
| Magnesium stearate | 2 |
| Total | 165 |

The tablet formulation was based on melt granulation in a high shear mixer Pellmix ⅛. 16 g Micronized tacrolimus was mixed with 640 g lactose 125 mesh and 120 g Polyethylene glycol 6000, 48 g Poloxamer 188 in the high shear mixer. The jacket of the mixer bowl was heated to 80° C. and the blend was heated at a impeller rotation speed of 1000 rpm until melting point of PEG and Poloxamer. After melting the kneading was continued for 4 minutes at 800 rpm. The granulated was sieved through sieve size of 0.7 mm and cooled on a tray. The granulate was mixed with 480 g Avicel PH200 for 3 minutes and for and after addition of 16 g magnesium stearate for further 0.5 minute. The mixture was compressed into tablets on a single punch tabletting machine Diaf TM20. Tablet diameter: 7 mm. Tablet shape: round, compound cup. Enteric coating of the tablets is performed in accordance with the procedure described in Example 11.

Example 17

In Vitro Dissolution Data

Compositions and dosage forms according to the previous examples were subjected to in vitro dissolution tests using two different dissolution media/tests.

A. Using the dissolution medium/test: 900 ml aqueous medium with 0.005% HPC (hydroxypropylcellulose) adjusted to pH=4.5 (USP paddle method; rotation speed: 50 rpm), the following dissolution profiles were found:

| Time (hours) | % Release | | | | | |
| --- | --- | --- | --- | --- | --- | --- |
| | Ex. 1 | Ex. 3 | Ex. 4 | Ex. 8 (Rsd %) | Ex. 9 - EC (Rsd %) | Ex. 10 (Rsd %) |
| 0 | 0 | 0 | 0 | 0 (0) | 0 (0) | 0 (0) |
| 0.5 | | | 2 | | | |
| 1 | | | 4 | | | |
| 1.5 | 0 | 0 | | | | |
| 2 | 0 | 0 | | | | |
| 3 | | | 6 | | | |
| 4 | 1 | 3 | | 7.8 (11.1) | 0.8 (32.3) | 7.4 (9.8) |
| 5 | | | | | | |
| 6 | 3 | 4 | | | | |
| 8 | 5 | 7 | 17 | 17.0 (8.3) | 0.4 (61.1) | 13.3 (16.5) |
| 10 | 20 | 14 | | | | |
| 15 | 40 | | | 32.2 (4.8) | 11.0 (17.3) | 36.0 (5.8) |
| 16 | | 38 | | | | |
| 17 | | | | 35.1 (9.6) | 13.2 (12.1) | 44.5 (5.4) |
| 20 | | | | | | |
| 24 | | | 37 | | | |

Dissolution profile for tablet cores of Example 9 in dissolution media: 900 ml, aqueous media with 0.005% HPC (hydroxypropylcellulose) adjusted to pH=4.5. USP paddle method. Rotation speed: 50 rpm:

| Time (minutes) | % release | Rsd % |
| --- | --- | --- |
| 0 | 0 | 0 |
| 5 | 27.2 | 15.1 |
| 10 | 49.1 | 10.9 |
| 20 | 80.7 | 8.0 |
| 35 | 98.9 | 5.4 |
| 42 | 102.7 | 3.6 |
| 52 | 104.9 | 2.0 |

Dissolution profile for enteric coated tablets example 9 in dissolution medium accord. to USP Method A, delayed release articles. USP Paddle method. Rotation speed: 50 rpm:

| Time (minutes) | % release | Rsd % |
| --- | --- | --- |
| 0 | 0 | NA |
| 120 | 0 | NA |
| 155 | 84.8 | 12.8 |
| 165 | 102.9 | NA |
| 175 | 101.0 | 3.5 |

Example 18

List of Stability Improving Measures for Improving and Optimizing an Extended Release Tacrolimus Formulation Comprising Tacrolimus in a Solid Solution.

Tacrolimus in solubilized form is prone to degradation and several degradation products may be produced during storage. Stability improving measurements tested for improving the stability of tacrolimus are disclosed in the following list.
Vehicles, Antioxidant formulations addition of
1000 ppm Propyl gallate
500 ppm α-Tocopherol+500 ppm Lipoid
500 ppm Ascorbyl palmitate
1000 ppm α-Tocopherol
500 ppm α-Tocopherol
50 ppm α-Tocopherol
1000 ppm Ascorbyl palmitate+1000 ppm α-Tocopherol
500 ppm Ascorbyl palmitate+500 ppm α-Tocopherol 250 ppm Ascorbyl palmitate+250 ppm α-Tocopherol
50 ppm Ascorbyl palmitate+50 ppm α-Tocopherol
Removal of impurities in a poloxamer by filtering through Al2O3 (Compalox)
Addition of Dimethicon
Addition of BHT
Addition of organic acids including Tartaric acid
0.01% Tartaric acid, 0.05% Tartaric acid, 0.10% Tartaric acid, 0.20% Tartaric acid,
0.40% Tartaric acid, 0.50% Tartaric acid, 0.60% Tartaric acid, 0.75% Tartaric acid, 1%
Tartaric acid, 5% Tartaric acid
Variation of Tartaric acid around 0.15%, with 200 ppm α-Tocopherol
Tablets, dried with N2 at
25° 4 h dried by N2, low heat 65° C. low heating time,
25° 24 h dried by N2, low heat 65° C. low heating time,
40° 4 h dried by N2, low heat 65° C. low heating time,
40° 24 h dried by N2, low heat 65° C. low heating time
Tablets, open storage in different controlled humidities,
11% humidity by LiCl
32% humidity by MgCl2,
48% humidity by K2CO3, 75% humidity by NaCl
89% humidity by KNO3

Example 19

A Clinical Study Comparing an Extended Release Formulation According to the Present Invention with Prograf® in Stable Kidney and Liver Transplant Patients, Respectively.

Figure 5:
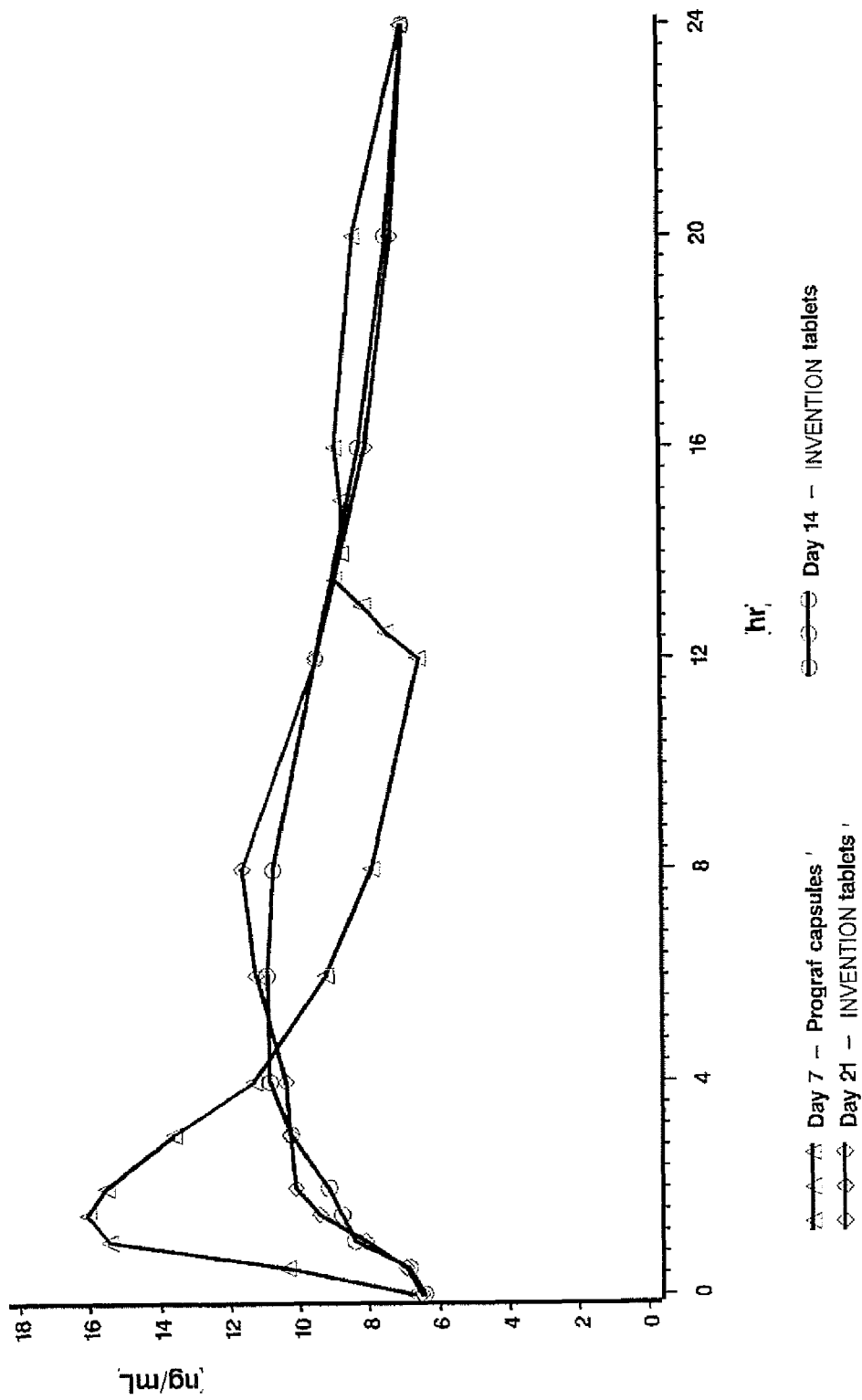
FIG. 5 discloses steady state blood profiles obtained before conversion (Prograf® day 7 steady state) and after conversion on day 14 and day 21 to the extended release formulation according to the present invention in stable liver patients. Squares denote Prograf® bid day 7, circles LCP-Tacro once daily on day 17, and diamonds depict LCP tacro once daily on day 21. The details of the study are disclosed herein in Example 19. The profiles show the actual profiles after conversion to a lower dose with the formulation according to the invention.
Figure 6:
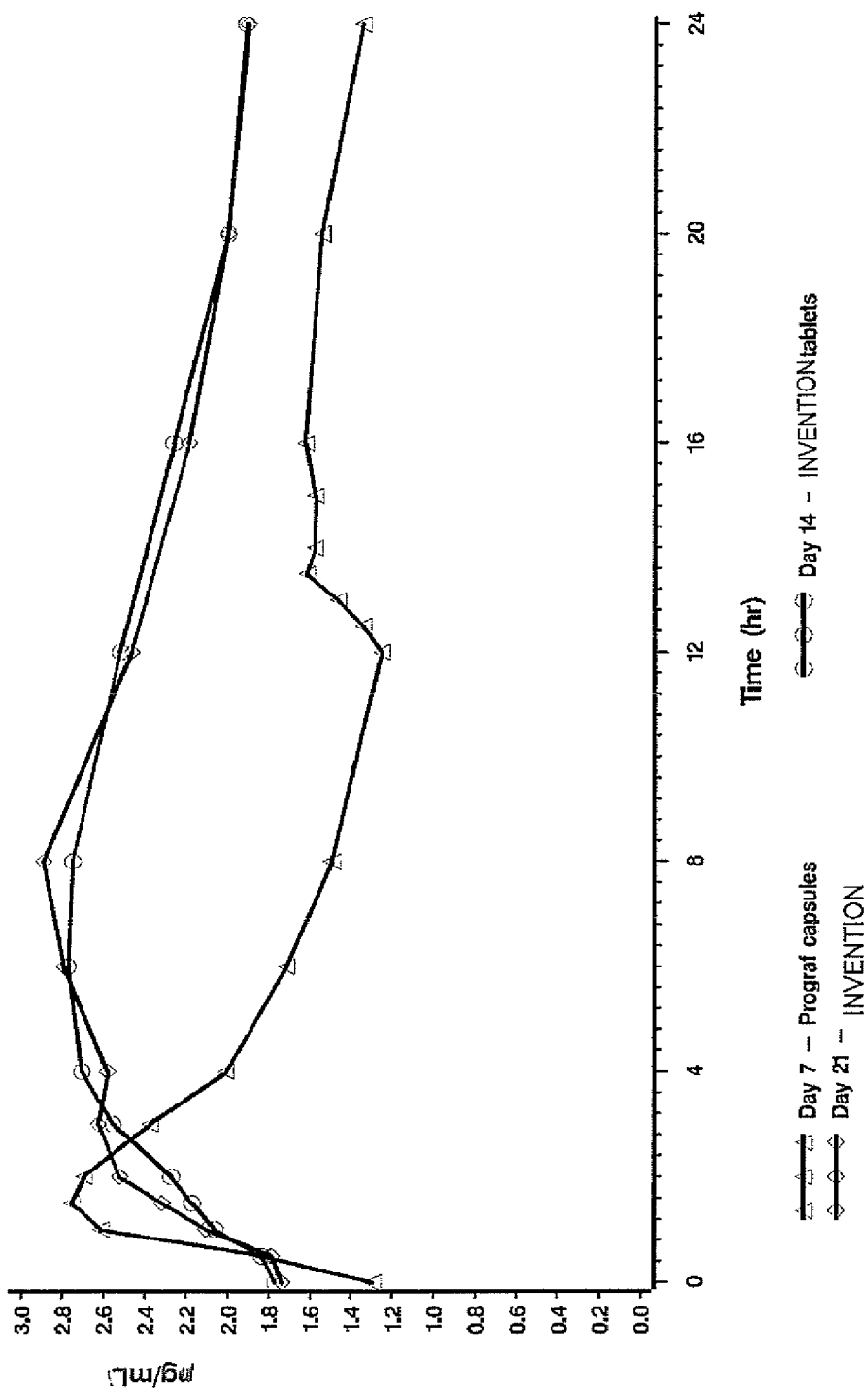
FIG. 6 shows the dose corrected steady state blood profiles of FIG. 5.

Blood concentration profiles are disclosed in FIGS. 5 and 6 for stable kidney patients. Study Title:
A Phase II, Open-Label, Multi-Center Prospective, Conversion Study in Stable Kidney Transplant Patients to Compare the Pharmacokinetics of LCP-Tacro Tablets Once-A-Day to Prograf® Capsules Twice-A-Day. LCP-Tacro 1 mg, 2 mg, 5 mg Tablets Active Ingredient: Tacrolimus.

Indications: Tacrolimus (Prograf®) is used to prevent rejection of liver, kidney and heart transplants.

Study Design and Phase of Development: 3-sequence, open-label, prospective, multicenter, conversion trial (Phase II).

Title of Study: A Phase II, Open-Label, Multi-Center Prospective, Conversion Study in Stable Kidney Transplant Patients to Compare the Pharmacokinetics of LCP-Tacro Tablets Once-A-Day to Prograf® Capsules Twice-A-Day Objectives: To evaluate tacrolimus exposure (AUC0-24) and trough levels (C24) in stable kidney transplant recipients converted from Prograf® Capsules (tacrolimus, Astellas Pharma US, Inc.) to LCP-Tacro tablets in a three sequence study design, and to evaluate the safety of LCP-Tacro compared to Prograf.

Main Criteria for Inclusion: Men and women 18-65 years of age who were recipients of a renal transplant at least 6 months prior to enrollment.

Test Products/Investigational Products and Modes of Administration: LCP-Tacro 1 mg, 2 mg, 5 mg Tablets, administered orally once daily in the morning. Reference Product, Lot Number and Mode of Administration: Prograf® 0.5 mg, 1 mg, 5 mg Capsules, administered b.i.d. in two equally divided doses, once in the morning and once in the evening.

Methodology: A three sequence, open-label, multi-center, prospective, study in stable kidney transplant patients to assess and compare the pharmacokinetics (Cmax, C24, and AUC), and safety of LCP-Tacro (tacrolimus) tablets versus Prograf® (tacrolimus) capsules.

Stable kidney transplant patients who fulfilled all inclusion/exclusion (I/E) criteria were enrolled and kept on Prograf® for 7 days. Following a 24-hour PK study on Day 7 to determine pharmacokinetics for Prograf®, all patients were converted to once daily LCP-Tacro (Ratio 1:0.66-0.80) for 7 days with no dose changes allowed. On Day 14 a 24-hour LCP-Tacro PK study was performed. On Day 15 one predefined dose change was allowed if there was more than 25% change in the mean of 3 trough levels measured on Days 10±1, 12±1 (separated by at least 48 hours from the previous sample) and 14 compared to the mean of 3 trough levels measured on Days 0, 7 and 8 for each individual patient.

Patients remained on the dose determined on Day 14 for another 7 days with no dose changes allowed. Another 24-hour LCP-Tacro PK study was performed on Day 21. On Day 22 patients were converted back to their original twice-daily dose of Prograf® for a safety follow-up period of 30 days ending with a safety assessment at Day 52. An interim PK analysis was preformed after 10 patients complete Day 21, before continuing enrollment.

Blood Draw Timepoints: The following blood samples were drawn during this study:
For LCP-Tacro: Blood sampling points included: 0.00 (pre-dose), 0.50, 1.00, 1.50, 2.00, 3.00, 4.00, 6.00, 8.00, 12.00, 14.00, 16.00, 20.00 and 24.00 hours post dose, on Days 14 and 21.
For Prograf®: Blood sampling points included: 0.00 (pre-dose), 0.50, 1.00, 1.50, 2.00, 3.00, 4.00, 6.00, 8.00, 12.00, 12.50, 13.00, 13.50, 14.00, 15.00, 16.00, 20.00 and 24.00 hours after the morning dose, on Day 7.

Criteria for Evaluation: The pharmacokinetic analysis was performed on 47 patients. The safety assessment was performed on all patients who received at least 1 dose during the course of the study.

Pharmacokinetics (PK): The following pharmacokinetic parameters for tacrolimus were calculated by standard non-compartmental methods: $AUC_\tau$ ($\tau$=24), Cmax, Cmin, Cave, Tmax, % Fluctuation, % Swing and Cmax/Cmin.

Statistical Methods: All demographic data, pharmacokinetic parameters, laboratory data and AEs were summarized using descriptive statistics. For continuous data, the mean, standard deviation, median, minimum and maximum were reported. For categorical data, percent and frequency were reported.

Non-compartmental pharmacokinetic parameters [$AUC_\tau$ ($\tau$=24), Cmax, Cmin, Cave, Tmax] were calculated from blood concentration-time data.

Statistical Methods: Using GLM procedures in SAS, ANOVA was performed on natural logarithmic (ln) transformed parameters $AUC_\tau$, Cmax, Cmin, and Cavg and on untransformed parameters % fluctuation, % swing, and Cmax/Cmin. The model included treatment as a factor. The ratio of geometric LSMs along with the 90% CI was calculated according to the following three comparisons for AUCτ, Cmax, and Cmin:
Day 14 Prograf versus Day 7 LCP-Tacro
Day 21 Prograf versus Day 7 LCP-Tacro
Day 21 LCP-Tacro versus Day 14 LCP-Tacro The parameter Tmax was analyzed using nonparametric methods. The Wilcoxon signed-rank test for pairwise treatments comparisons was used. The mean shift between 2 treatments (as described above) was estimated by the median unbiased Hodges-Lehmann estimate and 90% exact confidence interval.

The degree of correlation between $AUC_\tau$ and Cmin was quantified by calculating a correlation coefficient and presenting graphical displays of the data on Days 7, 14, and 21. Both parameters were ln-transformed prior to correlation analysis. Statistical analysis of subgroup race (Blacks vs. Non-Blacks) was performed as a suitable split was obtained between the two groups.

Summary of Pharmacokinetic Results:
Pharmacokinetic Parameters Of For Tacrolimus In All Patients:

| | Geometric Mean (% CV) Arithmetic Mean ± SD | | | | | |
|---|---|---|---|---|---|---|
| | Dose Uncorrected Data | | | Dose Corrected Data | | |
| | Prograf® Capsules b.i.d. orally | LCP-Tacro Tablets q.d. orally | | Prograf® Capsules b.i.d. orally | LCP-Tacro Tablets q.d. orally | |
| Pharmacokinetic Parameters | Day 7 (n = 47) | Day 14 (n = 47) | Day 21 (n = 46) | Day 7 (n = 47) | Day 14 (n = 47) | Day 21 (n = 46) |
| AUCτ # (ng · hr/mL) | 212.12 (25.59) 218.82 ± 55.99 | 206.79 (29.27) 215.71 ± 63.14 | 209.05 (31.30) 218.03 ± 68.23 | 34.81 (52.08) 39.89 ± 20.78 | 47.73 (57.25) 56.83 ± 32.54 | 48.30 (56.46) 56.90 ± 32.13 |
| Cmax (ng/mL) | 17.66 (42.59) 19.14 ± 8.15 | 12.64 (36.02) 13.45 ± 4.84 | 13.05 (41.91) 13.94 ± 5.84 | 2.90 (41.11) 3.18 ± 1.31 | 2.92 (47.24) 3.29 ± 1.56 | 3.02 (47.92) 3.44 ± 1.65 |
| Cmin (ng/mL) | 6.82 (22.01) 7.00 ± 1.54 | 6.59 (33.41) 6.96 ± 2.32 | 6.64 (31.70) 6.94 ± 2.20 | 1.12 (66.74) 1.35 ± 0.90 | 1.52 (64.87) 1.91 ± 1.24 | 1.53 (70.71) 1.92 ± 1.35 |
| Cavg (ng/mL) | 8.84 (25.59) 9.12 ± 2.33 | 8.62 (29.27) 8.99 ± 2.63 | 8.71 (31.29) 9.08 ± 2.84 | 1.45 (52.08) 1.66 ± 0.87 | 1.99 (57.25) 2.37 ± 1.36 | 2.01 (56.46) 2.37 ± 1.34 |
| Tmax (hr)* | 1.82 (0.50-24.00) | 6.00 (1.00-16.00) | 6.00 (1.50-16.00) | 1.82 (0.50-24.00) | 6.00 (1.00-16.00) | 6.00 (1.50-16.00) |
| Degree of Fluctuation (%) | 127.41 ± 57.28 | 73.24 ± 44.96 | 77.04 ± 50.59 | 127.41 ± 57.28 | 73.24 ± 44.96 | 77.04 ± 50.59 |
| Degree of Swing (%) | 174.55 ± 93.72 | 102.80 ± 75.24 | 110.07 ± 89.23 | 174.55 ± 93.72 | 102.80 ± 75.24 | 110.07 ± 89.23 |
| Cmax/Cmin | 2.75 ± 0.94 | 2.03 ± 0.75 | 2.10 ± 0.89 | 2.75 ± 0.94 | 2.03 ± 0.75 | 2.10 ± 0.89 |

*median (min-max);
τ = 24 hours

Summary of Pharmacokinetic Results (cont'd):
Pharmacokinetic Parameters of for Tacrolimus in Black Patients:

| | Geometric Mean (% CV) Arithmetic Mean ± SD | | | | | |
|---|---|---|---|---|---|---|
| | Dose Uncorrected Data | | | Dose Corrected Data | | |
| | Prograf® Capsules b.i.d. orally | LCP-Tacro Tablets q.d. orally | | Prograf® Capsules b.i.d. orally | LCP-Tacro Tablets q.d. orally | |
| Pharmacokinetic Parameters | Day 7 (n = 20) | Day 14 (n = 20) | Day 21 (n = 19) | Day 7 (n = 20) | Day 14 (n = 20) | Day 21 (n = 19) |
| AUCτ # (ng · hr/mL) | 242.19 (24.78) 250.12 ± 61.98 | 204.13 (32.48) 214.78 ± 69.77 | 216.93 (39.32) 231.41 ± 90.99 | 26.35 (74.70) 31.41 ± 23.47 | 31.57 (84.23) 38.13 ± 32.11 | 32.50 (84.71) 39.17 ± 33.18 |
| Cmax (ng/mL) | 21.72 (41.29) 23.73 ± 9.80 | 13.89 (41.05) 15.20 ± 6.24 | 14.48 (48.92) 15.91 ± 7.78 | 2.36 (46.02) 2.61 ± 1.20 | 2.15 (60.56) 2.46 ± 1.49 | 2.17 (64.07) 2.53 ± 1.62 |
| Cmin (ng/mL) | 7.43 (21.57) 7.62 ± 1.64 | 6.21 (37.53) 6.62 ± 2.49 | 6.68 (38.83) 7.09 ± 2.75 | 0.81 (107.31) 1.07 ± 1.15 | 0.96 (99.20) 1.26 ± 1.25 | 1.00 (120.04) 1.34 ± 1.61 |

-continued

|  | Dose Uncorrected Data | | | Dose Corrected Data | | |
|---|---|---|---|---|---|---|
|  | Prograf® Capsules b.i.d. orally | LCP-Tacro Tablets q.d. orally | | Prograf® Capsules b.i.d. orally | LCP-Tacro Tablets q.d. orally | |
| Pharmacokinetic Parameters | Day 7 (n = 20) | Day 14 (n = 20) | Day 21 (n = 19) | Day 7 (n = 20) | Day 14 (n = 20) | Day 21 (n = 19) |
| Cavg (ng/mL) | 10.09 (24.78) 10.42 ± 2.58 | 8.51 (32.49) 8.95 ± 2.91 | 9.04 (39.32) 9.64 ± 3.79 | 1.10 (74.70) 1.31 ± 0.98 | 1.32 (84.22) 1.59 ± 1.34 | 1.35 (84.70) 1.63 ± 1.38 |
| Tmax (hr)* | 1.91 (0.50-24.00) | 4.00 (1.00-12.00) | 6.00 (1.50-16.00) | 1.91 (0.50-24.00) | 4.00 (1.00-12.00) | 6.00 (1.50-16.00) |
| Degree of Fluctuation (%) | 145.87 ± 60.72 | 94.99 ± 54.11 | 91.42 ± 63.47 | 145.87 ± 60.72 | 94.99 ± 54.11 | 91.42 ± 63.47 |
| Degree of Swing (%) | 212.69 ± 108.38 | 138.16 ± 91.69 | 135.87 ± 114.34 | 212.69 ± 108.38 | 138.16 ± 91.69 | 135.87 ± 114.34 |
| Cmax/Cmin | 3.13 ± 1.08 | 2.38 ± 0.92 | 2.36 ± 1.14 | 3.13 ± 1.08 | 2.38 ± 0.92 | 2.36 ± 1.14 |

*median (min-max);
τ = 24 hours

Pharmacokinetic Parameters of for Tacrolimus in Non-Black Patients:

|  | Dose Uncorrected Data | | | Dose Corrected Data | | |
|---|---|---|---|---|---|---|
|  | Prograf® Capsules b.i.d. orally | LCP-Tacro Tablets q.d. orally | | Prograf® Capsules b.i.d. orally | LCP-Tacro Tablets q.d. orally | |
| Pharmacokinetic Parameters | Day 7 (n = 27) | Day 14 (n = 27) | Day 21 (n = 27) | Day 7 (n = 27) | Day 14 (n = 27) | Day 21 (n = 27) |
| AUCτ # (ng · hr/mL) | 192.28 (19.32) 195.64 ± 37.79 | 208.78 (27.32) 216.40 ± 59.11 | 203.68 (21.98) 208.62 ± 45.86 | 42.79 (35.25) 46.18 ± 16.28 | 64.82 (36.10) 70.69 ± 25.52 | 63.83 (36.26) 69.37 ± 25.15 |
| Cmax (ng/mL) | 15.15 (27.81) 15.74 ± 4.38 | 11.79 (24.56) 12.14 ± 2.98 | 12.14 (27.91) 12.55 ± 3.50 | 3.37 (34.44) 3.60 ± 1.24 | 3.66 (33.56) 3.92 ± 1.31 | 3.80 (33.35) 4.08 ± 1.36 |
| Cmin (ng/mL) | 6.41 (19.98) 6.54 ± 1.31 | 6.88 (30.70) 7.20 ± 2.21 | 6.60 (25.79) 6.84 ± 1.76 | 1.43 (39.02) 1.56 ± 0.61 | 2.14 (41.92) 2.40 ± 1.01 | 2.07 (42.40) 2.32 ± 0.98 |
| Cavg (ng/mL) | 8.01 (19.31) 8.15 ± 1.57 | 8.70 (27.32) 9.02 ± 2.46 | 8.49 (21.98) 8.69 ± 1.91 | 1.78 (35.25) 1.92 ± 0.68 | 2.70 (36.10) 2.95 ± 1.06 | 2.66 (36.26) 2.89 ± 1.05 |
| Tmax (hr)* | 1.52 (0.50-13.48) | 6.00 (2.00-16.00) | 7.87 (1.53-12.05) | 1.52 (0.50-13.48) | 6.00 (2.00-16.00) | 7.87 (1.53-12.05) |
| Degree of Fluctuation (%) | 113.74 ± 51.53 | 57.13 ± 28.34 | 66.92 ± 37.20 | 113.74 ± 51.53 | 57.13 ± 28.34 | 66.92 ± 37.20 |
| Degree of Swing (%) | 146.30 ± 70.76 | 76.61 ± 46.88 | 91.92 ± 62.46 | 146.30 ± 70.76 | 76.61 ± 46.88 | 91.92 ± 62.46 |
| Cmax/Cmin | 2.46 ± 0.71 | 1.77 ± 0.47 | 1.92 ± 0.62 | 2.46 ± 0.71 | 1.77 ± 0.47 | 1.92 ± 0.62 |

*median (min-max);
τ = 24 hours

Summary of Pharmacokinetic Results (Cont'd):

Relative Bioavailability Assessments for Day 14 Versus Day 7 for Tacrolimus in all Patients:

| | Dose Uncorrected Data | | | Dose Corrected Data | | |
|---|---|---|---|---|---|---|
| Parameter | 90% C.I. | Ratio of Means | Infra-Subject CV | 90% C.I. | Ratio of Means | Infra-Subject CV |
| AUCτ* | 88.63% to 107.23% | 97.49% | 28.44% | 111.97% to 167.84% | 137.09% | 64.84% |
| Cmax | 63.09% to 81.23% | 71.59% | 38.29% | 84.52% to 119.91% | 100.67% | 54.74% |
| Cmin | 87.33% to 106.70% | 96.53% | 29.97% | 107.43% to 171.51% | 135.74% | 77.33% |

*τ = 24 hours

Relative Bioavailability Assessments for Day 21 Versus Day 7 for Tacrolimus in all Patients:

| | Dose Uncorrected Data | | | Dose Corrected Data | | |
|---|---|---|---|---|---|---|
| Parameter | 90% C.I. | Ratio of Means | Infra-Subject CV | 90% C.I. | Ratio of Means | Infra-Subject CV |
| AUCτ* | 89.55% to 108.46% | 98.55% | 28.44% | 113.19% to 170.03% | 138.73% | 64.84% |
| Cmax | 65.11% to 83.95% | 73.93% | 38.29% | 87.29% to 124.08% | 104.07% | 54.74% |
| Cmin | 87.91% to 107.53% | 97.23% | 29.97% | 108.17% to 173.12% | 136.84% | 77.33% |

*τ = 24 hours

Relative Bioavailability Assessments For Day 21 versus Day 14 For Tacrolimus In All Patients:

| | Dose Uncorrected Data | | | Dose Corrected Data | | |
|---|---|---|---|---|---|---|
| Parameter | 90% C.I. | Ratio of Means | Infra-Subject CV | 90% C.I. | Ratio of Means | Infra-Subject CV |
| AUCτ* | 91.86% to 111.26% | 101.09% | 28.44% | 82.56% to 124.03% | 101.20% | 64.84% |
| Cmax | 90.96% to 117.27% | 103.28% | 38.29% | 86.71% to 123.25% | 103.38% | 54.74% |
| Cmin | 91.07% to 111.40% | 100.72% | 29.97% | 79.69% to 127.54% | 100.81% | 77.33% |

*τ = 24 hours

Correlation Between AUCτ and Cmin For Tacrolimus:

| | Dose Uncorrected Data | | | | | |
|---|---|---|---|---|---|---|
| | Day 7 | | Day 14 | | Day 21 | |
| Parameter | AUCτ (ng · hr/mL) | Cmin (ng/mL) | AUCτ (ng · hr/mL) | Cmin (ng/mL) | AUCτ (ng · hr/mL) | Cmin (ng/mL) |
| Mean | 5.35716 | 1.92049 | 5.33171 | 1.88517 | 5.34260 | 1.89238 |
| Standard Deviation | 0.25141 | 0.23353 | 0.29591 | 0.33707 | 0.28751 | 0.29989 |
| Correlation | 0.78656 | | 0.91380 | | 0.86471 | |
| p-value | <.0001 | | <.0001 | | <.0001 | |

| | Dose Corrected Data | | | | | |
|---|---|---|---|---|---|---|
| | Day 7 | | Day 14 | | Day 21 | |
| Parameter | AUCτ (ng · hr/mL) | Cmin (ng/mL) | AUCτ (ng · hr/mL) | Cmin (ng/mL) | AUCτ (ng · hr/mL) | Cmin (ng/mL) |
| Mean | 3.55001 | 0.11346 | 3.86547 | 0.41903 | 3.87736 | 0.42713 |
| Standard Deviation | 0.54311 | 0.62557 | 0.62680 | 0.72963 | 0.60442 | 0.69479 |
| Correlation | 0.97266 | | 0.99092 | | 0.98176 | |
| p-value | <.0001 | | <.0001 | | <.0001 | |

CONCLUSION

The primary objective of this study was to evaluate steady state tacrolimus exposure (AUC$_\tau$) and trough levels (Cmin) in stable kidney transplant recipients converted from Prograf® (tacrolimus, Astellas Pharma US, Inc.) to LCP-Tacro in a three sequence study design.

Following dose correction, the systemic exposure of tacrolimus at steady-state (AUC$_\tau$) and the trough tacrolimus levels (Cmin) were significantly higher when LCP-Tacro tablets q.d. were administered compared to therapy with Prograf® Capsules b.i.d. in kidney transplant patients. The systemic exposure (AUC$_\tau$ and Cmin) over the period of 24 hours of LCP-Tacro 2 mg Tablets (q.d.) was ~38% and ~36% higher than that of Prograf® Capsules (b.i.d). The average concentration of the drug over the dosing interval, Cavg, was significantly higher for the LCP-Tacro therapy compared to Prograf.

Also, there were no statistically significant differences in the peak systemic exposure (Cmax) of tacrolimus between Prograf® therapy and when LCP-Tacro was given on Days 14 and 21. In addition, the treatment with Prograf® showed a significantly higher degree of fluctuation and swing compared to LCP-Tacro. There was a greater correlation between AUC$_\tau$ and Cmin on days 14 and 21 (LCP-Tacro therapy) compared to Prograf® (Day 7); however, the magnitude of difference was not high. There were no significant differences in the overall systemic exposure, trough tacrolimus levels or degree of fluctuation and swing when comparing LCP-Tacro given on Day 14 compared to when it was given on Day 21.

A sub-group analysis of blacks versus non-blacks who are either on Prograf® or LCP-Tacro therapy, shows that there were statistical differences in the peak and systemic exposure of tacrolimus as well as the trough tacrolimus levels indicating the necessity for caution when dosing the black population.

The results from this study show that following conversion from Prograf to LCP-Tacro, LCP-Tacro therapy shows a significantly higher systemic exposure and a less degree of fluctuation and swing of tacrolimus at steady state when compared to when Prograf® therapy is given to stable kidney transplant patients. In addition, the peak exposure of tacrolimus is similar upon comparing the different treatments; however the average concentration over the dosing interval was higher for LCP-Tacro.

Discussion and Overall Conclusions: The primary objective of this study was to evaluate steady state tacrolimus exposure ($AUC_\tau$) and trough levels (Cmin) in stable kidney transplant recipients converted from Prograf® (tacrolimus, Astellas Pharma US, Inc.) to LCP-Tacro in a three sequence study design.

Following dose correction, the systemic exposure of tacrolimus at steady-state ($AUC_\tau$) and the trough tacrolimus levels (Cmin) were significantly higher when LCP-Tacro tablets q.d. were administered compared to therapy with Prograf® Capsules b.i.d. in kidney transplant patients. The systemic exposure ($AUC_\tau$ and Cmin) over the period of 24 hours of LCP-Tacro 2 mg Tablets (q.d.) was ~38% and ~36% higher than that of Prograf® Capsules (b.i.d). The average concentration of the drug over the dosing interval, Cavg, was significantly higher for the LCP-Tacro therapy compared to Prograf®. Also, there were no statistically significant differences in the peak systemic exposure (Cmax) of tacrolimus between Prograf® therapy and when LCP-Tacro was given on Days 14 and 21. In addition, the treatment with Prograf® showed a significantly higher degree of fluctuation and swing compared to LCP-Tacro. There was a greater correlation between $AUC_\tau$ and Cmin on days 14 and 21 (LCP-Tacro therapy) compared to Prograf® (Day 7); however, the magnitude of difference was not high. There were no significant differences in the overall systemic exposure, trough tacrolimus levels or degree of fluctuation and swing when comparing LCP-Tacro given on Day 14 compared to when it was given on Day 21.

A sub-group analysis of blacks versus non-blacks who are either on Prograf® or LCP-Tacro therapy, shows that there were statistical differences in the peak and systemic exposure of tacrolimus as well as the trough tacrolimus levels indicating the necessity for caution when dosing the black population.

The results from this study show that following conversion from Prograf to LCP-Tacro, LCP-Tacro therapy shows a significantly higher systemic exposure and a less degree of fluctuation and swing of tacrolimus at steady state when compared to when Prograf® therapy is given to stable kidney transplant patients. In addition, the peak exposure of tacrolimus is similar upon comparing the different treatments; however the average concentration over the dosing interval was higher for LCP-Tacro.

Results from Study in Stable Liver Transplant Patients
Summary statistics of dose uncorrected pharmacokinetic parameters of tacrolimus in male and female stable liver transplant patients on days 7, 14, and 21

| Parameter | Day 7 Mean ± SD | Day 14 Mean ± SD | Day 21 Mean ± SD |
| --- | --- | --- | --- |
| $AUCtau^\wedge$ (ng · hr/mL) | 205.09 ± 61.28 196.35 (29.88)* | 194.93 ± 58.99 185.34 (30.26)* | 215.52 ± 79.43 202.15 (36.85)* |
| Cmax (ng/mL) | 18.46 ± 7.77 16.87 (42.07)* | 12.49 ± 4.08 11.80 (32.66)* | 13.70 ± 5.95 12.62 (43.39)* |
| Cmin (ng/mL) | 6.72 ± 2.07 6.40 (30.76)* | 6.37 ± 2.38 5.91 (37.38)* | 6.85 ± 2.63 6.37 (38.44)* |
| Tmax (hr) | 3.18 ± 4.53 1.82 (142.58)* | 6.31 ± 3.47 5.32 (55.07)* | 5.92 ± 3.31 5.05 (55.84)* |
| Cavg (ng/mL) | 8.55 ± 2.55 8.18 (29.88)* | 8.12 ± 2.46 7.72 (30.26)* | 8.98 ± 3.31 8.42 (36.85)* |
| Degree of Fluctuation (%) | 133.46 ± 56.19 121.09 (42.10)* | 79.21 ± 47.10 67.02 (59.47) | 76.60 ± 40.97 65.34 (53.48)* |
| Degree of Swing (%) | 175.02 ± 80.68 154.73 (46.10)* | 112.44 ± 83.36 87.59 (74.14)* | 107.97 ± 67.32 86.44 (62.35)* |
| Cmax/Cmin | 2.75 ± 0.81 2.63 (29.34)* | 2.12 ± 0.83 2.00 (39.24)* | 2.08 ± 0.67 1.98 (32.37)* |

*Geometric Mean (% CV) N = 56 on day 21, N = 57 on day 7 and day 14
$^\wedge$tau = 24 hrs.
Day 7 - Prograf® capsules b.i.d. orally
Day 14 - LCP-Tacro tablets q.d. orally
Day 21 - LCP-Tacro tablets q.d. orally Comparison of dose uncorrected pharmacokinetic parameters of tacrolimus in male and female patients between day 7 and day 14

| | $AUCtau^\wedge$ | Cmax | Cmin |
| --- | --- | --- | --- |
| 90% Geometric C.I.* | 85.12% to 104.67% | 61.81% to 79.23% | 82.12% to 103.69% |
| Ratio of Means** | 94.39% | 69.98% | 92.28% |
| CV*** | 34.31% | 41.75% | 39.0 |

$^\wedge$tau = 24 hrs.
90% Geometric Confidence Interval using log-transformed data.
**Calculated using geometric means according to the formula: e((test drug)-(reference drug)) × 100%.
***Coefficient of variation for log-transformed pharmacokinetic parameter.
Day 14 - LCP-Tacro tablets q.d. orally
Day 7 - Prograf® capsules b.i.d. orally Comparison of dose uncorrected pharmacokinetic parameters of tacrolimus in male and female patients between day 7 and day 21

| | $AUCtau^\wedge$ | Cmax | Cmin |
| --- | --- | --- | --- |
| 90% Geometric C.I.* | 92.80% to 114.22% | 66.04% to 84.75% | 88.45% to 111.79% |
| Ratio of Means** | 102.95% | 74.81% | 99.44% |
| CV*** | 34.3 | 41.75% | 39.00% |

$^\wedge$tau = 24 hrs.
90% Geometric Confidence Interval using log-transformed data.
**Calculated using geometric means according to the formula: e((test drug)-(reference drug)) × 100%.
***Coefficient of variation for log-transformed pharmacokinetic parameter.
Day 21 - LCP-Tacro tablets q.d. orally
Day 7 - Prograf® capsules b.i.d. orally Comparison of dose uncorrected pharmacokinetic parameters of tacrolimus in male and female patients between day 14 and day 21

| | $AUCtau^\wedge$ | Cmax | Cmin |
| --- | --- | --- | --- |
| 90% Geometric C.I.* | 98.31% to 121.00% | 94.37% to 121.11% | 95.85% to 121.15% |
| Ratio of Means | 109.07% | 106.91% | 107.76% |
| CV*** | 34.31% | 41.75% | 39.00% |

$^\wedge$tau = 24 hrs.
*90% Geometric Confidence Interval using log-transformed data.
**Calculated using geometric means according to the formula: e((test drug)-(reference drug)) × 100%.
***Coefficient of variation for log-transformed pharmacokinetic parameter.
Day 21 - LCP-Tacro tablets q.d. orally
Day 14 - LCP-Tacro tablets q.d. orally Summary statistics of dose corrected pharmacokinetic parameters of tacrolimus in male and female stable liver transplant patients on days 7, 14, and 21

| Parameter | Day 7 Mean ± SD | Day 14 Mean ± SD | Day 21 Mean ± SD |
|---|---|---|---|
| AUCtau^ (ng · hr/mL) | 38.13 ± 16.45 34.99 (43.13)* | 50.85 ± 21.96 45.87 (43.1) | 51.12 ± 22.14 46.85 (43.31)* |
| Cmax (ng/mL) | 3.36 ± 1.65 3.01 (49.16) | 3.19 ± 1.29 2.92 (40.31) | 3.13 ± 1.23 2.92 (39.25)* |
| Cmin (ng/mL) | 1.25 ± 0.54 1.14 (43.57)* | 1.68 ± 0.84 1.46 (50.08)* | 1.68 ± 1.48 (52.17)* |
| Tmax (hr) | 3.18 ± 4.53 1.82 (142.58)* | 6.31 ± 3.47 5.32 (55.07)* | 5.92 ± 3.31 5.05 (55.84)* |
| Cavg (ng/mL) | 1.59 ± 0.69 1.46 (43.13)* | 2.12 ± 0.92 1.91 (43.19)* | 2.13 ± 0.92 1.95 (43.31)* |
| Degree of Fluctuation (%) | 133.46 ± 56.19 121.09 (42.10)* | 79.21 ± 47.10 67.02 (59.47)* | 76.60 ± 40.97 65.34 |
| Degree of Swing (%) | 175.02 ± 80.68 154.73 (46.10) | 112.44 ± 83.36 87.59 (74.14 | 107.97 ± 67.32 86.44 (62.35)* |
| Cmax/Cmin | 2.75 ± 0.81 2.63 (29.34)* | 2.12 ± 0.83 2.00 (39.24)* | 2.08 ± 0.67 1.98 (32.37)* |

*Geometric Mean (% CV)
^tau = 24 hrs.
Day 7 - Prograf® capsules b.i.d. orally
Day 14 - LCP-Tacro tablets q.d. orally
Day 21 - LCP-Tacro tablets q.d. orally Comparison of dose corrected pharmacokinetic parameters of tacrolimus in male and female patients between day 7 and day 14

|  | AUCtau^ | Cmax | Cmin |
|---|---|---|---|
| 90% Geometric C.I.* | 114.35% to 150.28% | 85.04% to 111.06% | 109.63% to 149.81% |
| Ratio of Means** | 131.09% | 97.19% | 128.16 |
| CV*** | 46.33% | 45.15% | 53.77% |

^tau = 24 hrs.
*90% Geometric Confidence Interval using log-transformed data.
**Calculated using geometric means according to the formula: e((test drug)-(reference drug)) × 100%.
***Coefficient of variation for log-transformed pharmacokinetic parameter.
Day 14 - LCP-Tacro tablets q.d. orally
Day 7 - Prograf® capsules b.i.d. orally Comparison of dose corrected pharmacokinetic parameters of tacrolimus in male and female patients between day 7 and day 21

|  | AUCtau^ | Cmax | Cmin |
|---|---|---|---|
| 90% Geometric C.I.* | 116.73% to 153.59% | 85.09% to 111.26% | 110.56% to 151.29% |
| Ratio of Means** | 133.90% | 97.30% | 129.33% |
| CV*** | 46.33% | 45.15% | 53.77% |

^tau = 24 hrs.
*90% Geometric Confidence Interval using log-transformed data.
**Calculated using geometric means according to the formula: e((test drug)-(reference drug)) × 100%.
***Coefficient of variation for log-transformed pharmacokinetic parameter.
Day 21 - LCP-Tacro tablets q.d. orally
Day 7 - Prograf® capsules b.i.d. orally Comparison of dose corrected pharmacokinetic parameters of tacrolimus in male and female patients between day 14 and day 21

|  | AUCtau^ | Cmax | Cmin |
|---|---|---|---|
| 90% Geometric C.I.* | 89.04% to 117.16% | 87.56% to 114.48% | 87.56% to 114.48% |
| Ratio of Means** | 102.14% | 100.12% | 100.92% |
| CV*** | 46.33% | 45.15% | 53.77% |

^tau = 24 hrs.
*90% Geometric Confidence Interval using log-transformed data.
**Calculated using geometric means according to the formula: e((test drug)-(reference drug)) × 100%.
***Coefficient of variation for log-transformed pharmacokinetic parameter.
Day 21 - LCP-Tacro tablets q.d. orally
Day 14 - LCP-Tacro tablets q.d. orally As appears from the results of the stable liver transplant patients the following is obtained: Approximately 31% improvement in bioavailability; approximately 30 reduction in dose achieved bioequivalence for AUC(0-24) and C(min24); reduced Cmax:Cmin ratio and high AUC:Cmin correlation.

Example 20

Comparison of a Formulation According to the Invention (LCP-Tacro) Against a Commercial Available Extended Release Tacrolimus Formulation for Once Daily Dosing, Advagraf®

The primary objective of this study is to determine and compare the rate and extent of absorption of tacrolimus from a test formulation of LCP-Tacro 2 mg Tablets taken once daily (q.d.) versus the reference Advagraf® 2×1 mg Capsules (q.d.) under multiple-dose, fasting conditions.

Advagraf® is manufactured by Astellas Pharma GmbH Munich, Germany Study Synopsis

| | |
|---|---|
| Experimental Design | A randomized, two-way crossover, open-label, multiple-dose, fasting design. |
| Population | Thirty normal, healthy, non-smoking Caucasian male subjects. |
| Study Drugs | LCP-Tacro 2 mg Tablets<br>Advagraf ® 1 mg Capsules |
| Treatments | Subjects will receive 1 of the following treatments on Days 1 to 10 of each study period, according to a randomization scheme:<br>Treatment A: 1 LCP-Tacro 2 mg Tablet (q.d.) (Daily treatment dose = 2 mg)<br>Treatment B: 2 Advagraf® 1 mg Capsules (q.d.) (Daily treatment dose = 2 mg) |
| Duration of Treatment | This study consists of 2 sixteen-day periods (with a follow-up visit 30 to 35 days after the last dose of Period II) separated by at least a two-week washout period from the last dose of Period I to the first dose of Period II. Subjects will be institutionalized from the day before Day 1 dosing until 24 hours after Day 10 dosing for each study period.<br>Subjects are required to return for subsequent blood draws. |

-continued

| Blood Collection | Pharmacokinetics (PK):<br>A total of 50 blood samples (4 mL each) will be drawn in each period according to the following schedule:<br>Day 1: 0.00 (pre-dose), 0.50, 1.00, 1.50, 2.00, 3.00, 4.00, 5.00, 6.00, 7.00, 8.00, 9.00, 10.00, 12.00, 14.00, 16.00, 20.00 and 24.00 (pre-dose for Day 2 dosing) hours post-dose.<br>Days 5, 6, 7, 8, and 9: 0.00 (pre-dose) and 12.00 hours post-dose.<br>Day 10: 0.00 (pre-dose), 0.50, 1.00, 1.50, 2.00, 3.00, 4.00, 5.00, 6.00, 7.00, 8.00, 9.00, 10.00, 12.00, 14.00, 16.00, 20.00, 24.00, 48.00, 72.00, 96.00 and 120.00 hours post-dose.<br>Biochemistry<br>Samples will be drawn during this study as follows:<br>Pre-Study: At the screening visit(s)<br>Days 3 and 8: 0.00 hour (pre-dose)<br>End-of-Study: After the last return blood draw<br>Post-Study Follow-up visit: Between Days 30 to 35 after the last dose of Period II.<br>457.5 mL of blood will be taken from each subject. |
|---|---|

PK: The PK parameters was calculated using non-compartmental analysis for tacrolimus as follows:

Day 1: $AUC_{0-24}$, Cmax, C24, and $T_{max}$.

Day 10: $AUC_\tau$ ($\tau$=24), $C_{max}$, $C_{min}$, $C_{avg}$, $T_{max}$, $t\frac{1}{2}$, KeI, % Fluctuation, % Swing, AUC$\tau$/Cmin, Cmax/Cmin and Accumulation Ratio (R).

Statistics: Descriptive statistics was calculated for blood concentrations and for all PK parameters. The ratio (Test/Reference) of geometric least square means (LSMs) and the 90% confidence interval (CI) was calculated for natural logarithmic (ln) transformed parameters AUC0-24, AUC$\tau$, Cmax, C24, Cmin, Cavg and untransformed parameters % Fluctuation, % Swing, R, Cmax/Cmin, AUC$\tau$/Cmin, KeI and t½. Tmax was analyzed using nonparametric methods.

The following results were obtained demonstrating significant higher bioavailability with a product according to the invention and at the same time having a profile demonstrating a much more extended absorption of the drug of almost 50%, much lower fluctuation in concentrations during the dosing period and high concentration by the end of the dosing interval where by a true once daily effect is obtained and any toxicity or side effect related to periods with high concentrations is eliminated to the extend possible with an oral once daily formulation. The present invention provided a formulation which with an 2 mg oral dosing in the morning provides an average concentration for full 24 hours which is above 4 ng/mL (according to results below a Cmin of 4.66 ng/mL is provided) which is substantially higher than with the marketed once daily product Advagraf® (Cmin 2.80 ng/mL) with the same administered dosage.

Pharmacokinetic parameters of tacrolimus in healthy Caucasian male subjects for treatment A, on day 1

TABLE 20-1

|  | Cmax (ng/mL) | AUC (0-24) (ng · hr/mL) | C24 (ng/mL) | Tmax (hr) |
|---|---|---|---|---|
| Mean | 3.60 | 49.79 | 1.82 | 7.52 |
| SD (±) | 1.04 | 13.26 | 0.56 | 3.08 |
| Median | 3.57 | 46.63 | 1.69 | 7.00 |
| CV (%) | 28.79 | 26.63 | 30.65 | 40.88 |
| Geometric Mean | 3.46 | 48.19 | 1.73 | 6.99 |
| Range (min) | 2.07 | 27.56 | 0.66 | 3.00 |
| (max) | 5.47 | 79.18 | 2.85 | 16.00 |
| n= | 21 | 21 | 21 | 21 |

Treatment A: 1 LCP-Tacro 2 mg Tablet (q.d.)

Pharmacokinetic parameters of tacrolimus in healthy Caucasian male subjects for treatment B, on day 1

TABLE 20-2

|  | Cmax (ng/mL) | AUG (0-24) (ng · hr/mL) | C24 (ng/mL) | Tmax (hr) |
|---|---|---|---|---|
| Mean | 3.44 | 34.00 | 0.97 | 2.19 |
| SD (±) | 0.99 | 9.41 | 0.37 | 0.77 |
| Median | 3.28 | 33.04 | 0.83 | 2.00 |
| CV (%) | 28.78 | 27.67 | 38.37 | 34.97 |
| Geometric Mean | 3.31 | 32.92 | 0.91 | 2.07 |
| Range (min) | 2.19 | 22.07 | 0.58 | 1.00 |
| (max) | 5.48 | 61.56 | 2.00 | 4.00 |
| n= | 21 | 21 | 21 | 21 |

Treatment B: 2 Advagraf® 1 mg Capsules (q.d.)

Pharmacokinetic parameters of tacrolimus in healthy Caucasian male subjects for treatment A, on day 10

TABLE 20-3

|  | $AUC_{tau}$ ng · hr/mL | Cmax ng/mL | Cmin ng/mL | Tmax (hr) | Cavg (ng/mL) | Kel (hr^(-1)) | T½ (hr) | Fluctuation (%) | Swing | R | Cmax/Cmin |
|---|---|---|---|---|---|---|---|---|---|---|---|
| Mean | 142.27 | 8.39 | 4.66 | 7.03 | 5.93 | 1.87E-02 | 37.97 | 64.72 | 85.45 | 2.85 | 1.85 |
| SD (±) | 49.41 | 2.89 | 1.71 | 2.96 | 2.06 | 2.76E-03 | 5.83 | 22.97 | 37.62 | 0.64 | 0.38 |
| CV (%) | 34.73 | 34.51 | 36.60 | 42.11 | 34.73 | 1.84E-02 | 37.62 | 35.48 | 44.03 | 22.42 | 20.29 |
| Median | 136.31 | 7.68 | 4.51 | 8.00 | 5.68 | 1.48E+01 | 15.36 | 64.06 | 87.79 | 2.91 | 1.88 |
| Geometric Mean | 133.99 | 7.93 | 4.35 | 6.03 | 5.58 | 1.85E-02 | 37.56 | 60.92 | 78.16 | 2.77 | 1.82 |
| Range (min) | 69.84 | 4.53 | 1.94 | 1.00 | 2.91 | 1.42E-02 | 29.03 | 31.46 | 36.05 | 1.52 | 1.36 |
| (Max) | 236.75 | 14.30 | 7.61 | 12.00 | 9.86 | 2.39E-02 | 48.94 | 123.52 | 191.31 | 4.29 | 2.91 |
| n = | 20 | 20 | 20 | 20 | 20 | 20 | 20 | 20 | 20 | 20 | 20 |

$Tau$ = m 24 hrs

Treatment A: 1 LCP Tacro 2 mg Tablet (q.d.)

Pharmacokinetic parameters of tacrolimus in healthy Caucasian male subjects for treatment B, on day 10

TABLE 20-4

|  | $AUC_{tau}$ ng·hr/mL | Cmax ng/mL | Cmin ng/mL | Tmax (hr) | Cavg (ng/mL) | Kel (hr^(−1)) | T½ (hr) | Fluctuation (%) | Swing | R | Cmax/Cmin |
|---|---|---|---|---|---|---|---|---|---|---|---|
| Mean | 94.15 | 7.00 | 2.80 | 2.40 | 3.92 | 1.83E-02 | 38.65 | 110.22 | 158.53 | 2.80 | 2.59 |
| SD (±) | 28.24 | 2.04 | 0.98 | 1.21 | 1.18 | 2.85E-03 | 5.69 | 28.20 | 48.20 | 0.86 | 0.48 |
| CV (%) | 29.99 | 29.21 | 34.79 | 50.40 | 29.99 | 1.77E-02 | 39.26 | 25.58 | 30.40 | 30.85 | 18.64 |
| Median | 89.82 | 6.97 | 2.52 | 2.00 | 3.74 | 1.55E+01 | 14.71 | 116.55 | 169.20 | 2.59 | 2.69 |
| Geometric Mean | 89.86 | 6.71 | 2.64 | 2.16 | 3.74 | 1.81E-02 | 38.24 | 106.46 | 150.98 | 2.70 | 2.54 |
| Range (min) | 49.14 | 4.32 | 1.39 | 1.0 | 2.05 | 1.40E-02 | 28.10 | 54.97 | 74.41 | 1.82 | 1.74 |
| (Max) | 138.85 | 10.50 | 4.46 | 6.00 | 5.79 | 2.47E-02 | 49.39 | 161.17 | 238.80 | 5.56 | 3.39 |
| n = | 20 | 20 | 20 | 20 | 20 | 20 | 20 | 20 | 20 | 20 | 20 |

Treatment B: 2 Advagraf® 1 mg Capsules (q.d.)

Comparison of Tmax of tacrolimus in healthy Caucasian male subjects between days 1 and 10, for treatments A and B

TABLE 20-5

| Treatment | Day 1 Median (Range) | Day 10 Median (Range) | Estimate, 90% C.I.* | p-value** |
|---|---|---|---|---|
| A | 7.00 (3.00, 16.00) | 8.00 (1.00, 12.00) | 0.00 (−2.00, 2.00) | 0.901 |
| B | 2.00 (1.00, 4.00) | 2.00 (1.00, 6.00) | 0.00 (−0.50, 0.00) | 0.776 |

*Hodges-Lehmann point estimate and 90% exact CI for the treatment difference
**p-value for treatment comparison based on the Wilcoxon-Mann-Whitney test.
Treatment A: 1 LCP Tacro 2 mg Tablet (q.d.)

TABLE 20-6

Treatment B: 2 Advagraf® 1 mg Capsules (q.d.)
Summary statistics and comparison of pharmacokinetic parameters of tacrolimus in healthy Caucasian male subjects, between treatments A and B, on day 1

|  | Treatment A | | Treatment B | |
|---|---|---|---|---|
| Paramenter | n | Mean ± SD | n | Mean ± SD |
| AUC(0-24) (ng·hr/mL) | 21 | 49.79 ± 13.26 48.19 (26.63)* | 21 | 34.00 ± 9.41 32.92 (27.67)* |
| C24 (ng/mL) | 21 | 1.82 ± 0.56 1.73 (30.65)* | 21 | 0.97 ± 0.37 0.91 (38.37)* |
| Cmax (ng/mL) | 21 | 3.60 ± 1.04 3.46 (28.79)* | 21 | 3.44 ± 0.99 3.31 (28.78)* |
| Tmax (hr) | 21 | 7.00 (3.00, 16.00)** | 21 | 2.00 (1.00, 4.00)** |

*Geometric mean (% CV)
**Median (Range)
Treatment A: 1 LCP Tacro 2 mg Tablet (q.d.)
Treatment B: 2 Advagraf® 1 mg Capsules (q.d.)

Summary statistics and comparison of pharmacokinetic parameters of tacrolimus in healthy Caucasian male subjects, between treatments A and B, on day 1

TABLE 20-7

|  | AUG (0-24) | C24 | Cmax |
|---|---|---|---|
| 90% Geometric C.I.1 | 133.95% to 163.57% | 161.80% to 222.46% | 93.92 to 118.70% |

TABLE 20-7-continued

|  | AUG (0-24) | C24 | Cmax |
|---|---|---|---|
| Ratio of Means2 | 148.02% | 189.72% | 105.59% |
| Intra-Subject CV3 | 18.69% | 30.18% | 21.97% |
| Degree of Freedom | 19 | 19 | 19 |

1. 90% Geometric Confidence Interval using log-transformed data
2. Calculated using geometric means according to the formula: e((test drug)−(reference drug))×100%
3. Intra-subject coefficient of variation for log-transformed pharmacokinetic parameter Test: Treatment A: 1 LCP Tacro 2 mg Tablet (q.d.)
Reference: Treatment B: 2 Advagraf® 1 mg Capsules (q.d.)

Summary statistics and comparison of pharmacokinetic parameters of tacrolimus in healthy Caucasian male subjects, between treatments A and B, on day 10

TABLE 20-8

|  | Treatment A | | Treatment B | |
|---|---|---|---|---|
| Parameter | n | Mean ± SD | n | Mean ± SD |
| AUCTau (ng·hr/mL) | 20 | 142.27 ± 49.41 133.99 (34.73)* | 20 | 94.15 ± 28.24 89.86 (29.99)* |
| Cmax (ng/mL) | 20 | 8.39 ± 2.89 7.93 (34.51)* | 20 | 7.00 ± 2.04 6.71 (29.21)* |
| Cmin (ng/mL) | 20 | 4.66 ± 1.71 4.35 (36.60)* | 20 | 2.80 ± 0.98 2.64 (34.79)* |
| Tmax (hr) | 20 | 7.03 ± 2.96 6.03 (42.11)* | 20 | 2.40 ± 1.21 2.16 (50.40)* |
| Cavg (ng/mL) | 20 | 5.93 ± 2.06 5.58 (34.73)* | 20 | 3.92 ± 1.18 3.74 (29.99)* |
| Degree of Fluctuation (%) | 20 | 64.72 ± 22.97 60.92 (35.48)* | 20 | 110.22 ± 28.20 106.46 (25.58)* |
| Degree of Swing (%) | 20 | 85.45 ± 37.62 78.16 (44.03)* | 20 | 158.53 ± 48.20 150.98 (30.40)* |
| R | 20 | 2.85 ± 0.64 2.77 (22.42)* | 20 | 2.80 ± 0.86 2.70 (30.85)* |
| Cmax/Cmin | 20 | 1.85 ± 0.38 1.82 (20.29)* | 20 | 2.59 ± 0.48 2.54 (18.64)* |
| T½ (hr) | 20 | 37.97 ± 5.83 | 20 | 38.65 ± 5.69 |
| Kel (hr^(−1)) | 20 | 1.87E-02 ± 2.76E-03 | 20 | 1.83E-02 ± 2.85E-03 |

*Geometric mean (% CV)
Treatment A: 1 LCP Tacro 2 mg Tablet (q.d.)
Treatment B: 2 Advagraf® 1 mg Capsules (q.d.)

Summary statistics and comparison of pharmacokinetic parameters of tacrolimus in healthy Caucasian male subjects, between treatments A and B, on day 10

TABLE 20-9

|  | AUCtau^ | Cmax | Cmin |
|---|---|---|---|
| 90% Geometric C.I.* | 137.43% to 161.12% | 105.33% to 127.73% | 152.29% to 180.25% |
| Ratio of Means** | 148.80% | 115.99% | 165.68% |
| Intra-Subject CV*** | 13.98% | 16.99% | 14.83% |
| Degree of Freedom | 17 | 17 | 17 |

^tau = 24 hrs
*90% Geometric Confidence Interval using log-transformed data
**Calculated using geometric means according to the formula: e ((test drug)-(reference drug)) X100%
***Intra-subject coefficient of variation for log-transformed pharmacokinetic parameter.
Treatment A: 1 LCP Tacro 2 mg Tablet (q.d.)

| Treatment B: 2 Advagraf ® 1 mg Capsules (q.d.) | |
|---|---|
| Extended release composition, stabilized | LCP-Tacro 2 mg |
| Tacrolimus monohydrate (2.00 mg calculated on the anhydrous basis) Excipients | 2.0400 mg |
| Butylated hydroxytoluene | 10.200 µg |
| Dimethicone 350 | 0.25500 µg |
| Hypromellose 2208 (15,000 cp) | 62.866 mg |
| Lactose monohydrate | 41.727 mg |
| Magnesium stearate | 1.5716 mg |
| Opadry II white 85G18490 | 4.7232 mg |
| Poloxamer 188 | 14.688 mg |
| Polyethylene glycol 6,000 | 34.272 mg |
| Tartaric acid | 255.00 µg |

Example 21

Table disclosing dissolution of a preferred embodiment of the invention having a composition as demonstrated above in Example 20 and the dissolution of the commercial product Advagraf® used for comparison in Example 20.

Figure 4:
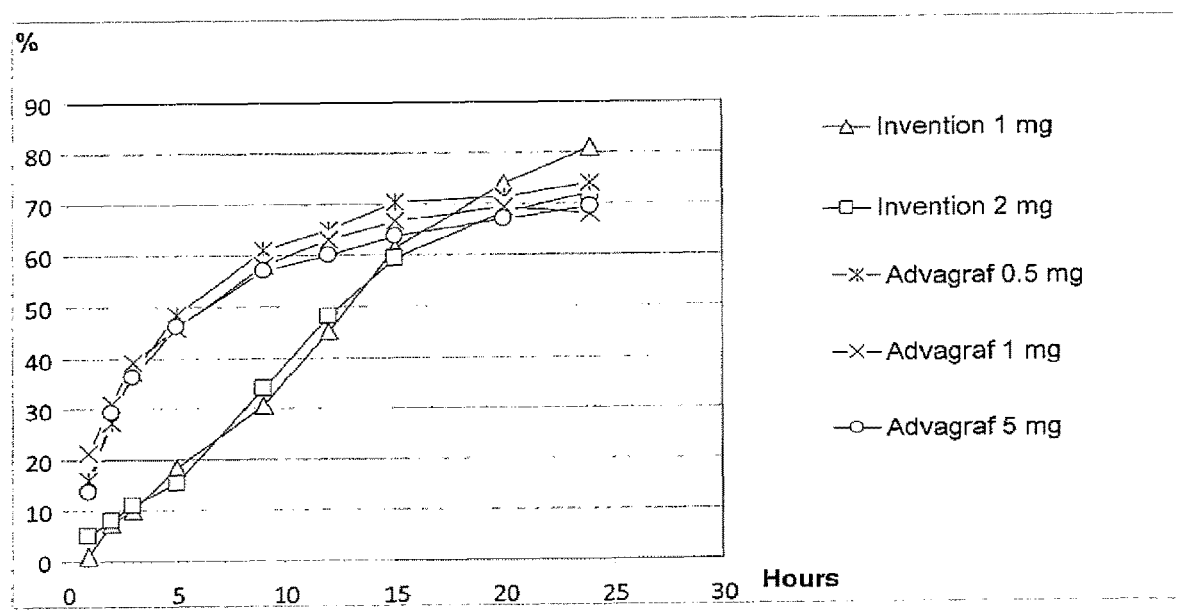
FIG. 4 shows the dissolution of a preferred formulation of the invention having a composition similar to the one described in Example 20. Triangles depicts treatment with a 1 mg formulation, squares with a 2 mg formulation. Further, the dissolution of the commercial product Advagraf® used for comparison in Example 20 are present where stars relates to a 0.5 mg, cross to a 1 mg and circles to a 5 mg Advagraf® product. The release is measured in percentage dissolved over time disclosed in hours. The dissolution method used is USP II dissolution test (paddle) method in a medium adjusted to pH 4.5, comprising 0.005% hydroxypropylcellulose, and a rotation of 50 rpm.

Release measured in percentage, dissolution method USP II dissolution test (paddle) method in a medium adjusted to pH 4.5 and comprising 0.005% hydroxylpropylcellulose, and a rotation of 50 rpm. The dissolution are disclosed in FIG. 4.

| | Dissolution Extended Formulation Batch no. | | | | | |
|---|---|---|---|---|---|---|
| | 0988/2006 | | 0989/2006 | | 0990/2006 | |
| Time, hrs | 1 mg assay | RSD | 2 mg assay | RSD | 5 mg Assay | RSD |
| 1 | 1.1 | 31.5 | 5 | 12.9 | 6.8 | 14.2 |
| 2 | 7.2 | 7.9 | 7.9 | 10.6 | 10.1 | 14.5 |
| 3 | 10.1 | 15.4 | 10.8 | 12.3 | 13.4 | 18.2 |
| 5 | 18.1 | 10.6 | 15.4 | 23.5 | 20.4 | 19.5 |
| 9 | 30.4 | 13.2 | 33.8 | 33.5 | 35.6 | 16.1 |
| 12 | 45.3 | 9.9 | 48 | 18.4 | 43.3 | 13.2 |
| 15 | 61.4 | 9.1 | 59.6 | 10.2 | 45.3 | 10 |
| 20 | 74 | 2.6 | 68.4 | 5.8 | 47 | 9.3 |
| 24 | 80.9 | 3.5 | 72.2 | 3.7 | 47.5 | 7.6 |

| | Formulation Batch no. | | | | | |
|---|---|---|---|---|---|---|
| | Advagraf OM4001A 0.5 mg | | 1M6002A 1 mg | | 5M4002A 5 mg | |
| Time, hrs | assay | RSD | assay | RSD | assay | RSD |
| 1 | 15.9 | 4.6 | 21.2 | 24.5 | 13.6 | 19.1 |
| 2 | 27.2 | 11.3 | 30.9 | 29.4 | 29.2 | 9.6 |
| 3 | 37.3 | 15 | 39.2 | 24.9 | 36.2 | 7 |
| 5 | 48.5 | 13 | 45.8 | 21.5 | 46 | 7.4 |
| 9 | 61.2 | 7.3 | 58 | 16.8 | 57.1 | 7.1 |
| 12 | 65 | 9.3 | 63 | 15.7 | 60.2 | 4.4 |
| 15 | 70.4 | 9.9 | 66.6 | 14.7 | 63.6 | 7.8 |
| 20 | 71.3 | 9.7 | 69.3 | 13.4 | 67 | 6.4 |
| 24 | 74.1 | 7.4 | 68.1 | 15.3 | 69.3 | 6.6 |

As appears from the dissolution, the extended release formulation according to the present invention provides a much longer and more extended profile with considerable lower release initially, for instance demonstrated by lower than 25% release at the 5 hour time point, despite a release at 3 hours which are at least 10%. Additionally, the curve profile according to the present invention has a substantial zero order release and a very extended release. The latter being clearly demonstrated by a less than 50% release at the 12 hour time point, and less than 62% release at the 15 hour time point. As appears from Example 20, the pharmacokinetic parameters are substantially improved with the extended release formulation according to invention in comparison with the commercially available Advagraf® product.

In addition, the extended release formulation according to the present invention may be provided in a much smaller tablet compared with Advagraf® as appears from the table below.

| Dosage from and strengts | Volume of dosage form, mm3 | Ratio Advagraf: LCP-Tacro (same strengts) |
|---|---|---|
| Advagraf ® 0.5 mg | 180 | |
| Advagraf ® 1 mg | 244 | 1.7 |
| Advagraf ® 5 mg | 927 | 2.7 |
| LCP-Tacro ™ 1 mg | 140 | |
| LCP-Tacro ™ 2 mg | 140 | |
| LCP-Tacro ™ 5 mg | 346 | |

Example 22

Extended Release Tacrolimus in De Novo Kidney Transplant Patients

De novo kidney transplant patients were randomized (1:1 ratio) within 12 hours after transplantation (Study Day 0) to receive either: 1) LCP-Tacro tablets (as outlined in Example 20 and the dissolution demonstrated in Example 21) orally once daily in the morning, with an interval of 24±1 hours between doses, starting at 0.14 mg/kg (the starting daily dose for Black patients was 0.17 mg/kg), or 2) Prograf capsules in two equally divided doses, starting at 0.1 mg/kg every 12 hours (0.2 mg/kg total daily dose) as currently recommended in the U.S. Prescribing Information (Astellas Pharma US, April 2006, NDA no. 050708). A 24-hour pharmacokinetic (PK) assessment was performed on Study Days 1, 7 and 14. Study Day 1 was defined as the day on which the first morning (AM) dose of study drug was given, which had to be within 48 hours of transplantation. Results are shown in table 22.

TABLE 22

| Parameter | Day | LCP-Tacro™ | | Prograf® | |
|---|---|---|---|---|---|
| | | n | Mean ± SD | n | Mean ± SD |
| $C_{max}$ (ng/mL) | 1 | 31 | 11.56 ± 6.83 9.52 (59.11) | 30 | 23.41 ± 11.10 20.83 (47.41)* |
| | 7 | 29 | 27.41 ± 17.53 23.11 (63.95)* | 28 | 24.12 ± 12.78 20.97 (52.99)* |
| | 14 | 28 | 28.21 ± 13.68 25.65 (48.51)* | 28 | 20.27 ± 6.49 19.15 (32.04)* |
| Cmin (ng/mL) | 1 | 31 | 5.80 ± 3.73 4.90 (64.20)* | 30 | 9.22 ± 4.35 8.27 (47.18)* |
| | 7 | 29 | 10.58 ± 7.18 8.92 (67.90)* | 28 | 10.35 ± 5.16 9.39 (49.92)* |
| | 14 | 28 | 10.37 ± 4.24 9.51 (40.84)* | 28 | 8.12 ± 3.13 7.45 (38.57)* |
| Tmax (hr) | 1 | 31 | 11.97 (4.02, 24.00)** | 30 | 4.00 (0.98, 24.00)** |
| | 7 | 29 | 6.00 (1.52, 12.10)** | 28 | 1.61 (0.50, 24.00)** |
| | 14 | 28 | 4.00 (1.33, 8.07)** | 28 | 1.88 (0.50, 14.05)** |
| Cavg (ng/mL) | 1 | 30 | 5.47 ± 3.20 | 29 | 10.59 ± 4.43 |
| | 7 | 27 | 13.31 ± 5.16 | 28 | 11.90 ± 4.09 |
| | 14 | 28 | 14.55 ± 4.66 | 28 | 10.61 ± 3.34 |
| Degree of fluctuation (%) | 1 | 30 | 89.90 ± 65.56 | 29 | 137.61 ± 77.01 |
| | 7 | 27 | 135.95 ± 121.44 | 28 | 107.74 ± 76.92 |
| | 14 | 28 | 131.10 ± 98.50 | 28 | 122.60 ± 59.98 |
| Degree of swing (%) | 1 | 31 | 118.07 ± 110.07 | 30 | 181.76 ± 126.72 |
| | 7 | 29 | 215.52 ± 244.56 | 28 | 152.79 ± 135.61 |
| | 14 | 28 | 210.18 ± 182.42 | 28 | 174.49 ± 100.91 |
| AUCR Day 7 to Day 1 | 1-7 | 26 | 4.30 ± 7.03 | 27 | 1.32 ± 0.69 |
| AUCR Day 14 to Day 1 | 1-14 | 28 | 4.37 ± 5.26 | 28 | 1.19 ± 0.59 |
| AUCR Day 14/Day 7 | 7-14 | 27 | 1.21 ± 0.51 | 28 | 1.04 ± 0.56 |

*Geometric mean (% CV)
**Median (Range)
AUCR is the accumulation ratio of AUCτ on the day shown to day 1

The $AUC_{0-\tau}$ for LCP-Tacro is significantly lower than that for Prograf® for the first day after transplantation (The dose uncorrected LCP-Tacro $AUC_{0-\tau}$ on Day 1 in the present was 131.11±76.78 versus 253.45±106.58 (ng·hr/mL)). However, for reduction of initial overimmunesuppression this is considered an advantage especially if the patients receives induction therapy and corticosteroids. According to the present invention, a target through value of 5-10 ng/mL (immunoassay method) is considered an optimal treatment compared with the extended release formulation according to the invention. Preferable in combination with a mycophenolate regimen with 1 gram twice daily administered in the form of mycophenolate mofetil (CellCept®) NDA no. 050722 and 050723 or a dosage form with an equivalent amount of mycophenolic acid such as Myfortic® NDA no 050791 (including generics thereto)

Examples of immunoassays for tacrolimus trough value measurements:

Tacrolimus Trough Method

Microparticle Enzyme Immunoassay (MEI) (Abbott)
Cedia Cloned Enzyme Donor Immunoassay
Siemens Dimension methodology
Enzyme immunoassay
Abbott IMX
Microparticle Enzyme Immunoassay (MEI) (Abbott)
ARCHITEC tacrolimus assay-chemiluminescent immunoassay (CMIA)
Abbott Imx
Cedia Cloned Enzyme Donor Immunoassay From the below Table (Table 23) it appears that a higher proportion of the patients obtain the target trough concentration according to the present invention of 5-10 ng/mL.

The table also shows that approximately two-thirds of the patients treated with LCP-Tacro are within the 5-7 ng/mL range after the first dose of LCP-Tacro and by Day 3 over 80% of the patients treated with LCP-Tacro were above the minimum 5 ng/mL level.

TABLE 23

Proportion of patients within and outside of a target concentration of 5-10 ng/mL (No (%))

| Trough (ng/mL) | Study drug | Day 2 | Day 3 | Day 4 | Day 7 | Day 10 | Day 12 | Day 14 |
|---|---|---|---|---|---|---|---|---|
| <5 | LCP-Tacro | 8 (26.7) | 6 (20.0) | 5 (1.7) | 3 (9.7) | 0 (0.0) | 0 (0.0) | 1 (3.4) |
| | Prograf® | 1 (3.6) | 2 (6.7) | 2 (7.7) | 2 (6.5) | 0 (0.0) | 1 (3.7) | 2 (6.9) |
| 5-10* | LCP-Tacro | 14 (46.7) | 13 (43.3) | 11 (36.7) | 12 (38.7) | 6 (24.0) | 5 (25.0) | 7 (24.1) |
| | Prograf® | 12 (42.9) | 9 (30.0) | 8 (30.8) | 9 (29.0) | 10 (38.5) | 6 (22.2) | 11 (37.9) |
| >10 | LCP-Tacro | 8 (26.7) | 11 (36.7) | 14 (46.7) | 16 (51.6) | 19 (76.0) | 15 (75.0) | 21 (72.4) |
| | Prograf® | 15 (53.6) | 19 (63.3) | 16 (61.5) | 20 (64.5) | 16 (61.5) | 20 (74.1) | 16 (55.2) |

Example 23

Clinical Studies with an Extended Release Formulation According to the Present Invention Table A Table A is a list of initial Clinical studies with an extended release formulation according to the present invention. The list includes the improved pharmacokinetic parameters obtained with an extended release formulation according to the present invention and claimed herein.

TABLE A

| | Cmax | Cmin12 | Cmin24 | Kel | Tmax | T½ |
|---|---|---|---|---|---|---|
| | | | LCP Fasted | | | |
| Study 002 | 10.05 ± 3.99 | 6.92 | 4.32 | 0.0217 | 8.55 ± 2.72 | 31.95 |
| Study 003 | 3.62 | NA | NA | NA | 6.71 (0.5-12) | 39.04 |
| Study 004 | 2.82 ± 0.96 | 2.42 ± 0.87 | 1.83 ± 0.72 | NA | 9.69 ± 4.90 | NA |
| Study 005 | 14.31 ± 4.29 | 6.504 ± 2.58 | 4.09 ± 1.70 | 2.07E-02 | 5.17 ± 1.68 | 35.14 ± 8.37 |
| | | | Prograf® Fasted | | | |
| | Cmax | Cmin12 | Cmin24 | Kel | Tmax | T½ |
| Study 002 | 32.75 ± 9.65 | 3.508 | 2.268 | 0.0208 | 1.63 ± 0.43 | 33.16 |
| Study 003 | NA | NA | NA | NA | NA | NA |
| Study 004 | 5.26 ± 1.28 | 0.63 ± 0.18 | NA | NA | 1.38 ± 0.42 | NA |
| Study 005 | 31.76 ± 8.81 | 4.24 ± 1.73 | 3.13 ± 1.14 | 2.05E-02 | 1.38 ± 0.34 | 34.86 ± 7.04 |

Figure 3:
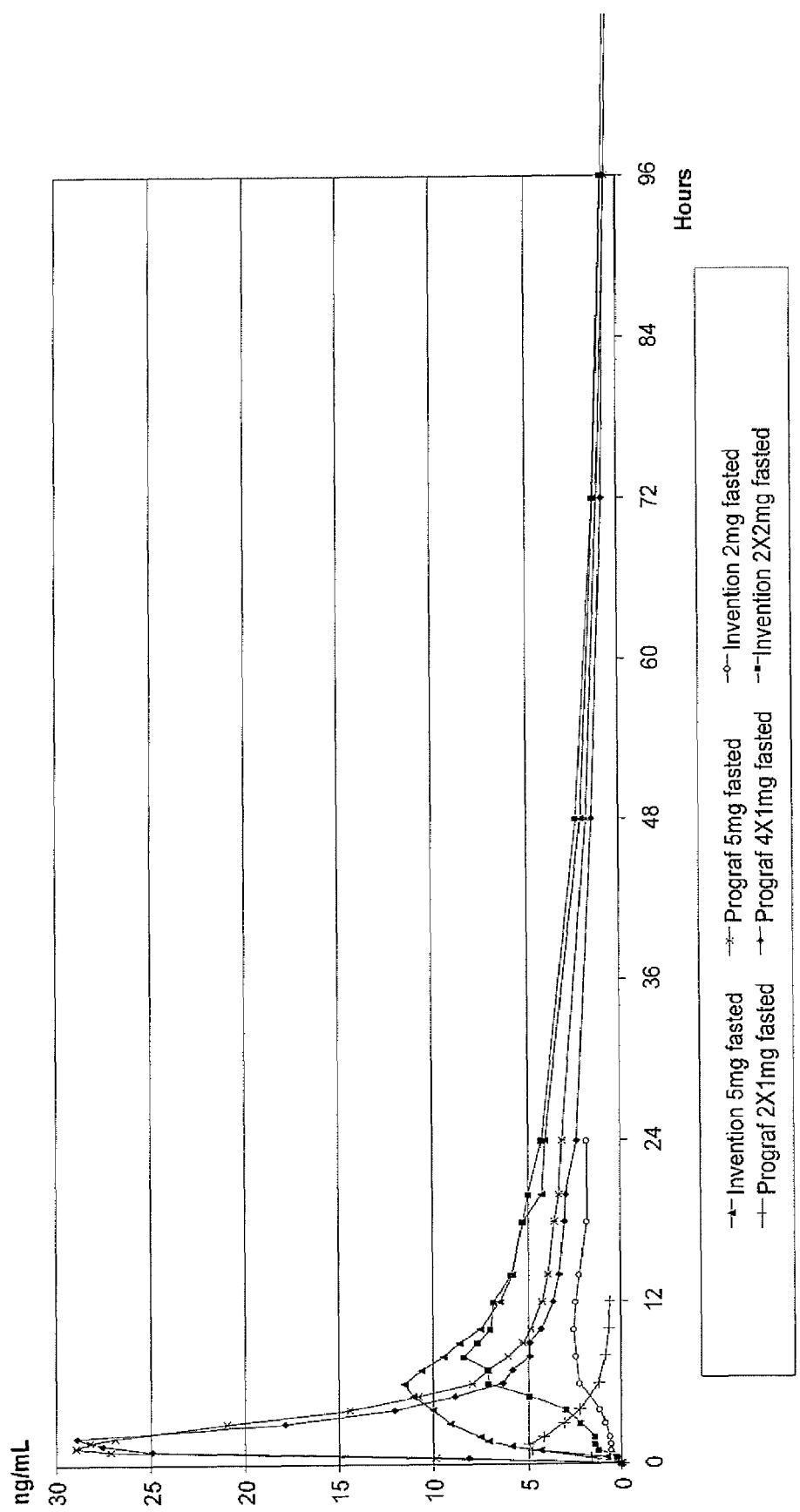
FIG. 3 shows blood concentrations of tacrolimus in a single dose study in fasted state of healthy volunteers. Closed triangles denotes concentration with a 5 mg formulation according to the present invention, stars denotes a Prograf® 5 mg formulation; open circles denotes a 2 mg formulation according to the present invention; closed squares denotes 2×2 mg treatment according to the present invention; closed diamonds denotes a Prograf® 4×1 mg treatment; vertical line denotes Prograf® 2×1 mg treatment. The study is described in Table A herein, as study 002.

Plasma profiles from the studies shown in Tables A and B are shown in FIG. 3.

TABLE B

| | Subjects | Title |
|---|---|---|
| Study 002 | 12 | 2-way cross-over; single-dose, fasting; LCP-Tacro tablets 2 × 2 mg modified release vs. Prograf capsules 4 × 1 mg (tacrolimus) |
| Study 003 | 6 | 2-way replicated design; single-dose, fasting, colon-absorption study on LCP-Tacro 2 mg |
| Study 004 | 13 | 2-way crossover, multi-dose, fasting, relative bioavailability study; LCP-Tacro tablets 2 mg q.d. vs. Prograf capsules 2 × 1 mg b.i.d. |

Single-Dose, Comparative PK Study (Study 002):

Study 002, a single-dose comparative pharmacokinetic study of LCP-Tacro 4 mg (2×2 mg tablets) vs. Prograf® 4 mg (4×1 mg capsules) demonstrated comparable AUC for both products when administered under fasting conditions. However, they differ in their rate of absorption when administered in the fasted condition, being slower and more sustained for the test formulation, LCP-Tacro. The longer $T_{max}$ for LCP-Tacro tablets (test; HPMC) vs. Prograf® capsules (tacrolimus; reference) (8.55 h vs. 1.63 h) combined with the lower $C_{max}$ (10.05 ng/ml vs. 32.75 ng/ml) and lower AUC(0→24) (122.4 ng*h/mL vs. 157.95 ng*h/mL), supports a once-a-day dosing for LCP-Tacro tablets compared to Prograf® capsules (tacrolimus)

Study 003:

Study 003 was designed as a replicate scintigraphic absorption study in 8 healthy volunteers to evaluate the transit time, pharmacokinetic profile and site of release of LCP-Tacro 2 mg tablets, radiolabelled with a maximum of 1 MBq 153Sm. In this study, an extended release profile could be demonstrated with a $T_{max}$ of ~6.7 hours. LCP-Tacro was well tolerated. Overall, this study demonstrated an in vivo extended release profile of LCP-Tacro tablets with release in all parts of the colon, and absorption of tacrolimus from distal parts of the gastrointestinal tract. The scintigraphic pictures are disclosed in FIG. 2 where pictures are taken 0.02, 0.53, 4.32, 4.57, 11.23, and 23.32 hours post-dose respectively.

Multi-Dose, Steady-State, Comparative PK Study (Study 004):

Study 004 is a multi-dose, steady-state comparative pharmacokinetic study of LCP-Tacro 2 mg q.d. vs. Prograf® 2×1 mg b.i.d in 14 healthy volunteers. This study demonstrated clearly a once-a-day profile of LCP-Tacro versus Prograf® b.i.d. In addition, this study demonstrated superior bioavailability of LCP-Tacro tablets given once-a-day compared to Prograf® capsules given twice-a-day. Upon administration of LCP-Tacro 2 mg tablets (q.d.) and Prograf® 1 mg capsules (b.i.d.) for 10 successive days, there were no significant differences observed in the morning pre-dose concentrations between Days 7, 8, 9, and 10, therefore steady state was maintained since Day 7. At steady state, the systemic exposure over the period of 24 hours of LCP-Tacro 2 mg Tablets (q.d.) was about 50% higher than that of Prograf 1 mg capsules (b.i.d.). The time to peak concentration between the single and multiple doses of LCP-Tacro 2 mg q.d. and Prograf® 2×1 mg b.i.d was similar for both treatments. As expected due to the extended release profile according to the invention, the LCP-Tacro 2 mg tablets (q.d.) had higher $C_{min}$ values and lower degree of fluctuation than that of the immediate-release Prograf® 1 mg capsules (b.i.d.). There was no significant difference observed in $C_{max}$ between the 2 treatments, as shown below in table 25.

TABLE 25

Pharmacokinetic Parameter Summary of Study 004

| | Geometric Mean (% CV) Arithmetic Mean ± SD | |
|---|---|---|
| | LCP-Tacro 2 mg Tablets (A; n = 13) | Prograf® 1 mg Capsules (B; n = 13) |
| $AUC_T$ (ng · hr/mL) | (34.98) 115.07 ± 40.25 | (34.26) 43.65 ± 14.95 |
| $AUC_{0-24}$ (ng · hr/mL) | Not applicable | 72.95 (34.40) 76.93 ± 26.46 |
| $C_{max}$ (ng/mL) | 6.42 (36.55) 6.80 ± 2.49 | 6.71 (31.30) 7.02 ± 2.20 |
| $C_{min}$ (ng/mL) | 3.12 (35.20) 3.31 ± 1.17 | 2.00 (40.51) 2.14 ± 0.87 |
| $T_{max}$ (hr)* | 8.00 (6.00-10.02) | 1.50 (1.00-2.00) |
| $t_{1/2}$ (hr) | 32.93 ± 2.66 | 32.59 ± 4.08† |
| $C_{max}/C_{min}$ | 2.12 ± 0.51 | 3.43 ± 0.75 |

*median (min-max);
†n = 12

TABLE C

List of additional Studies

| Study No/Phase | Subjects | Title |
|---|---|---|
| Study 1011 | 30 | A two-way crossover single-dose study of LCP-Tacro 5 mg tablet vs. Prograf 5 mg capsule |
| Study 1012 | 25 | A two-way crossover, open-label, multi-dose, fasting relative bioavailability study of LCP-Tacro 2 mg q.d. vs. Prograf 1mg b.i.d. × 10 days |
| Study 1013 | 25 | A single-dose, dose-linearity study of LCP-Tacro 5 mg vs. 7 mg vs. 10 mg |
| Study 1014 | 26 | A single-dose chrono-pharmaco-kinetic study of LCP-Tacro 2 mg tablets administered morning vs. evening |
| Study 1015 | 17 | A single-dose relative bioavail-ability study of LCP-Tacro 1 mg tablet vs. Prograf 1 mg capsule |

TABLE C-continued

List of additional Studies

| Study No/Phase | Subjects | Title |
|---|---|---|
| Study 1016 | 28 | A two-way crossover, open-label, multi-dose, fasting relative bioavailability study of LCP-Tacro 2 mg q.d. vs. Prograf 1 mg b.i.d. × 10 days |

Multi-Dose, Steady-State, Comparative PK Study (Study 1012):

This study evaluated and compared the bioavailability of tacrolimus from a test formulation of LCP-Tacro 2 mg tablets taken once daily (q.d.) in group A versus the reference Prograf 1 mg capsules taken twice daily (b.i.d.) in group B, under multiple-dose, fasting conditions. The study population consisted of 30 healthy volunteers receiving study treatment for a period of 10 days followed by a two-week wash-out and subsequent crossover between study groups. Twenty five patients were evaluable for this study. The pharmacokinetics of tacrolimus on Day 10 are summarized in Tables 26-27 below.

TABLE 26

Pharmacokinetic parameters for tacrolimus on Day 10 (Study 1012)

| Pharmacokinetic Parameters | Geometric Mean (% CV) Arithmetic Mean ± SD | |
|---|---|---|
| | LCP-Tacro 2 mg Tablets (A; q.d.; n = 25) | Prograf® 1 mg Capsules (B; b.i.d.; n = 25) |
| $AUC_{0-12}$ (ng · hr/mL) | 70.71 (27.94) 73.65 ± 20.58 | 48.98 (44.05) 54.22 ± 23.88 |
| $AUC_{12-24}$ (ng · hr/mL) | 54.81 (31.10) 57.72 ± 17.95 | 36.48 (43.15) 40.28 ± 17.38 |
| Cmax (ng/mL) | 7.49 (31.74) 7.85 ± 2.49 | 8.06 (40.91) 8.72 ± 3.57 |
| C12 (ng/mL) | 5.68 (31.88) 6.00 ± 1.91 | 2.47 (46.73) 2.78 ± 1.30 |
| Cavg (ng/mL) | 5.24 (29.04) 5.47 ± 1.59 | 3.57 (42.80) 3.94 ± 1.68 |
| Tmax (hr)* | 6.00 (1.00-10.00) | 1.50 (1.00-13.00) |
| $AUC_{0-12}/C12$ (hr) | 12.44 (13.44) 12.54 ± 1.68 | 19.82 (11.53) 19.94 ± 2.30 |
| $AUC_T$/Cmin (hr) | 32.00 (6.83) 32.07 ± 2.19 | 32.14 (11.25) 32.34 ± 3.64 |
| $AUC_{12-24}$/Cmin (hr) | 13.96 (5.70) 13.98 ± 0.80 | 13.69 (13.13) 13.80 ± 1.81 |

*median (min-max)

TABLE 27

Relative bioavailability assessments for tacrolimus on Day 10 (Study 1012)

| Parameter | 90% C.I. | Ratio of Means | Intra-Subject CV |
|---|---|---|---|
| $AUC_T$ | 131.49% to 162.84% | 146.33% | 22.31% |
| Cmin | 131.27% to 163.97% | 146.71% | 23.22% |

TABLE 28

Summary of pharmacokinetic parameters for study 1013 (Dose proportionality, NHV, n = 25).

| | Treatment A 1 × 5 mg | Treatment B 1 × 5 mg + 1 × 2 mg | Treatment C 2 × 5 mg |
|---|---|---|---|
| $AUC_{0-12}$ (ng · hr/mL) | 88.23 ± 32.87 | 125.33 ± 44.96 | 186.15 ± 56.81 |
| $AUC_{0-24}$ (ng · hr/mL) | 143.00 ± 54.23 | 212.69 ± 77.30 | 307.05 ± 98.07 |
| $AUC_{0-t}$ (ng · hr/mL) | 303.55 ± 133.60 | 449.63 ± 173.51 | 648.81 ± 224.20 |
| $AUC_{0-inf}$ (ng · hr/mL) | 324.46 ± 143.52 | 473.40 ± 182.86 | 687.68 ± 241.22 |
| Cmax (ng/mL) | 12.21 ± 4.84 | 16.73 ± 5.22 | 24.91 ± 7.15 |
| Tmax (hr) | 5.18 ± 2.36 | 5.63 ± 2.53 | 5.76 ± 1.39 |
| C24 (ng/mL) | 3.91 ± 1.74 | 6.11 ± 2.57 | 8.63 ± 3.43 |

Study 1014 (Diurnal variability, NHV):

This study investigated the pharmacokinetic profile of tacrolimus after administration of LCP-Tacro 2 mg in the morning vs. evening in 26 male and female healthy volunteers under fasting conditions. The study consisted of two eight-day periods separated by at least a two-week washout period between treatments. The mean pharmacokinetic parameters are summarized in Table 29 below.

TABLE 29

Summary of Pharmacokinetic Parameters from study 1014

| | Evening Dose 1 × 2 mg, n = 26 | Morning Dose 1 × 2 mg, n = 25 |
|---|---|---|
| $AUC_{0-t}$ (ng · hr/mL) | 61.65 ± 24.31 | 113.10 ± 41.89 |
| $AUC_{0-12}$ (ng · hr/mL) | 28.18 ± 8.28 | 29.85 ± 9.20 |
| $AUC_{0-24}$ (ng · hr/mL) | 50.51 ± 14.74 | 54.50 ± 16.80 |
| $AUC_{0-inf}$ (ng · hr/mL) | 106.74 ± 35.11 | 124.78 ± 42.82 |
| $C_{max}$ (ng/mL) | 4.39 ± 1.21 | 4.20 ± 1.46 |
| $T_{max}$ (hr) | 6.77 ± 2.69 | 6.66 ± 2.79 |
| C24 (ng/mL) | 1.34 ± 0.52 | 1.69 ± 0.67 |

TABLE 30

Study 1014-Diurnal variability, NHV

| | Ratio of means (%) | Intra-subject CV (%) |
|---|---|---|
| $AUC_{0-t}$ | 86.93 | 39.48 |
| $AUC_{0-12}$ | 97.95 | 26.91 |
| $AUC_{0-24}$ | 95.67 | 26.67 |
| $AUC_{0-inf}$ | 87.64 | 35.56 |
| Cmax | 109.65 | 29.49 |

Study 1015

This study compared the rate and extent of absorption of tacrolimus after LCP-Tacro 1 mg tablet vs. Prograf® (tacrolimus) 1 mg capsule under fasting conditions in 17 normal healthy male or female subjects. The study consisted of two eight-day periods separated by at least a two-week washout period between treatments. Pharmacokinetic results are summarized in Table below. The longer $T_{max}$ for LCP-Tacro tablets (8.78 h vs. 1.39 h) combined with the lower $C_{max}$ (2.54 ng/mL vs. 7.04 ng/mL) and lower AUC(0-inf) (71.82 ng*h/mL vs. 50.18 ng*h/mL), supports a once-a-day dosing for LCP-Tacro tablets compared to Prograf® capsules (tacrolimus).

| LCP-Tacro vs. Prograf, NHV, n = 17 | | |
| --- | --- | --- |
| | LCP-Tacro 1 × 1 mg tablet | Prograf® 1 × 1 mg capsule |
| AUC0-t (ng · hr/mL) | 61.65 ± 24.31 | 36.15 ± 22.71 |
| AUC0-12 (ng · hr/mL) | 16.43 ± 5.98 | 22.93 ± 10.64 |
| AUC0-24 (ng · hr/mL) | 31.21 ± 8.90 | 28.77 ± 13.75 |
| AUC0-inf (ng · hr/mL) | 71.82 ± 26.52 | 50.18 ± 28.38 |
| Cmax (ng/mL) | 2.54 ± 1.03 | 7.04 ± 3.56 |
| Tmax (hr) | 8.78 ± 5.05 | 1.39 ± 0.50 |
| C24 (ng/mL) | 1.04 ± 0.36 | 0.46 ± 0.25 |

| Study 1015-Diurnal variability, NHV, n = 17 | | |
| --- | --- | --- |
| | Ratio of means (%) | Intra-subject CV (%) |
| AUC0-t | 187.29 | 58.06 |
| AUC0-12 | 74.89 | 42.87 |
| AUC0-24 | 116.97 | 40.10 |
| AUC0-inf | 154.08 | 50.73 |
| Cmax | 37.63 | 51.81 |

Exposure to tacrolimus is significantly higher after LCP-Tacro tablets than after Prograf capsules, with reduced peak/trough fluctuation and delayed Tmax in NHV. The results are consistent with other PK data obtained with the extended release formulation according to the present invention.

The release time for the extended release dosage forms according to the invention used in the clinical trials described herein all provides an extended release profile where less than 63.5% is released within 15 hours. A relevant release profile in this respect is demonstrated in FIG. 1 tested according to the USP II dissolution test (paddle) in a medium at pH 4.5 and comprising 0.005% hydroxypropylcellulose, and a rotation of 50 rpm.

Example 24

A phase 1, two-way crossover, open label, multidose, bioequivalence study comparing the pharmacokinetics (Cmax, C24, and AUCtau), and safety of LCP-Tacro Tablets versus Advagraf® Capsules in steady state, fasting conditions was conducted.

Figure 7:
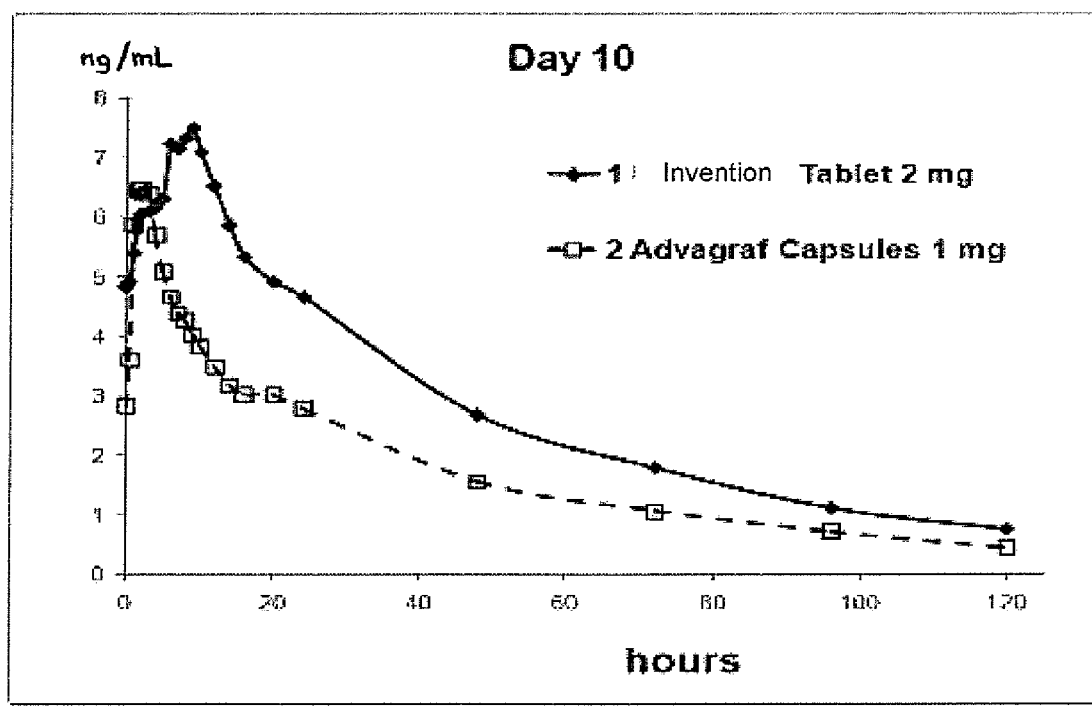
FIG. 7 shows the PK profile of LCP-Tacro Tablets versus Advagraf® Capsules in steady state, fasting conditions.
Figure 8:
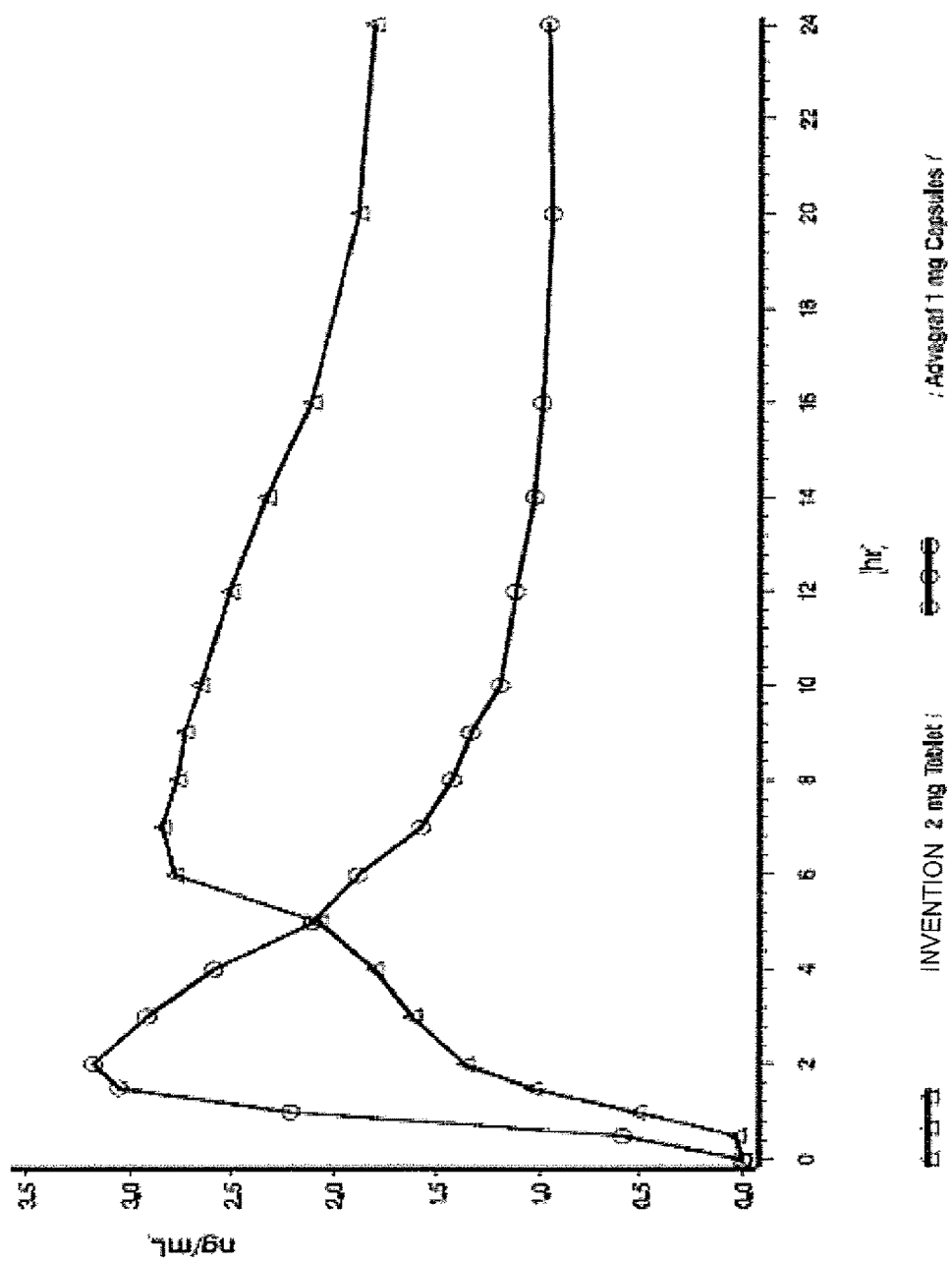
FIG. 8: Discloses the blood plasma concentrations after administration of the same single dosage of tacrolimus as Advagraf® 2×1 mg capsules open circles and as LCT-Tacro 2 mg tablet according to the present invention. The study is outlined in Example 20.
Figure 9:
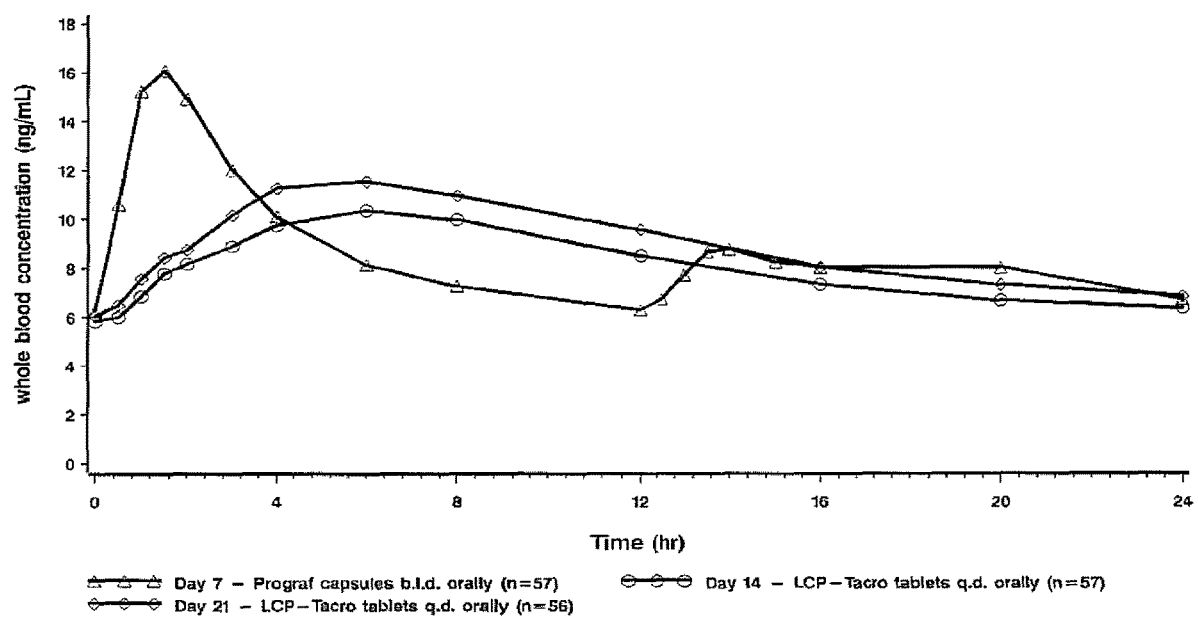
FIG. 9: Discloses steady state blood profiles obtained before conversion (Prograf® day 7 steady state) and after conversion on day 14 and day 21 to the extended release formulation according to the present invention in stable liver patients. Squares denotes Prograf® bid day 7, circles LCP-Tacro once daily on day 17, and diamonds LCP tacro once daily on day 21. The details of the study are disclosed herein in Example 19. The profiles disclose the actual profiles after conversion to a lower dose with the formulation according to the invention.
Figure 10:
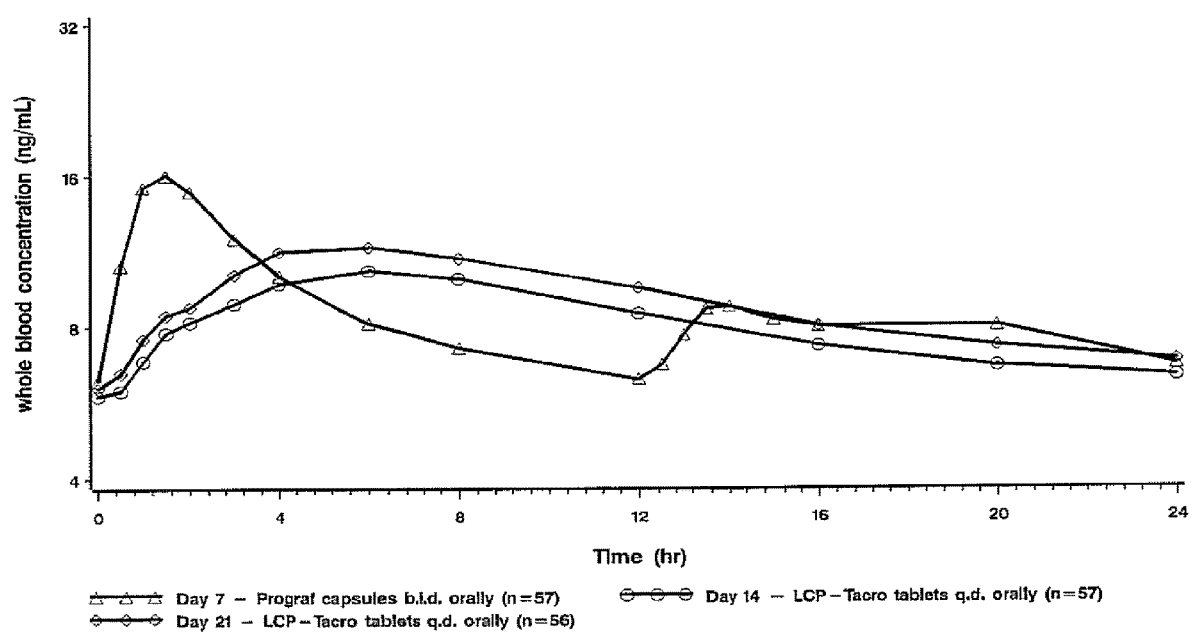
FIG. 10: Discloses the does corrected steady state blood profiles of FIG. 9.

Twenty healthy male volunteers were randomized to receive either one LCP-Tacro 2 mg tablet or two Advagraf® 1 mg Capsules daily for 10 days. After a two week washout period, each subject then received the alternative treatment. The PK profile after 10 days of each treatment is illustrated in the FIG. 7 and demonstrate that LCP-Tacro Tablets provide approximately 50% greater bioavailability of tacrolimus than a comparable dose of Advagraf®. The PK profile of the LCP-Tacro Tablets also supports once-a-day administration.

Patents, patent applications, publications, product descriptions, and protocols which are cited throughout this application are incorporated herein by reference in their entireties.

The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, and (ii) the $T_{max}$ on day 1, when administered under fasting conditions, is between 4 hours and 24 hours.

2. The method of claim 1, wherein $T_{max}$ is 8.55±2.72 hours.

3. The method of claim 1, wherein $T_{max}$ is 6.00 to 10.02 hours.

4. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the $T_{max}$ on day 1, when administered under fasting conditions, is between 4 hours and 24 hours, and (iii) the patient is concomitantly treated with mycophenolate mofetil.

5. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the $T_{max}$ on day 1, when administered under fasting conditions, is between 4 hours and 24 hours, and (iii) the patient is concomitantly treated with a corticosteroid.

6. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the $T_{max}$ on day 1, when administered under fasting conditions, is between 4 hours and 24 hours, and (iii) the patient is African-American.

7. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the $T_{max}$ on day 1, when administered under fasting conditions, is between 4 hours and 24 hours, and (iii) the plasma concentration of tacrolimus in the patient is maintained at a therapeutically effective amount without inducing nephrotoxicity or neurotoxicity.

8. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, (iii) at least 8% of the tacrolimus in each extended release composition is released at the 4 hour time point, (iv) 40% of the tacrolimus is released within 10 to 14 hours, and the $T_{max}$ on day 1, when administered under fasting conditions, is between 4 hours and 24 hours, when tested according to the USP II dissolution test (paddle) or USP I dissolution test (basket) method at a rotation of 50 rpm in a medium at pH 4.5 comprising 0.005% hydroxypropylcellulose.

9. The method of claim 8, wherein $T_{max}$ is 6.00 to 10.02 hours.

10. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, (iii) at least 8% of the tacrolimus in each extended release composition is released at the 4 hour time point, (iv) the $T_{max}$ on day 1, when administered under fasting conditions, is between 4 hours and 24 hours, and (v) the patient is concomitantly treated with mycophenolate mofetil.

11. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, (iii) at least 8% of the tacrolimus in each extended release composition is released at the 4 hour time point, (iv) the $T_{max}$ on day 1, when administered under fasting conditions, is between 4 hours and 24 hours, and (v) the patient is concomitantly treated with a corticosteroid.

12. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, (iii) at least 8% of the tacrolimus in each extended release composition is released at the 4 hour time point, (iv) the $T_{max}$ on day 1, when administered under fasting conditions, is between 4 hours and 24 hours, and (v) the patient is African-American.

13. The method of claim 8, wherein the plasma concentration of tacrolimus in the patient is maintained at a therapeutically effective amount without inducing nephrotoxicity or neurotoxicity.

14. A method of prophylaxis of organ rejection in a de novo kidney transplant patient comprising once daily orally administering to the patient an effective amount of tacrolimus in the form of one or more extended release compositions comprising tacrolimus, wherein the initial dose of tacrolimus is 0.14 mg/kg/day, and the target trough concentration for the tacrolimus is 5-10 ng/mL.

15. The method of claim 14, wherein at least 8% of the tacrolimus in each extended release composition is released at the 4 hour time point.

16. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, and (iii) the in vivo release of each composition after oral administration takes place substantially in the colon.

17. The method of claim 14, wherein the in vivo release of each composition after oral administration takes place substantially in one or more of the colon *ascendens*, colon *transversum* and colon *descendens*.

18. The method of claim 14, wherein (a) at least 8% of the tacrolimus is released at the 4 hour time point after administration of each composition, (b) less than 25% of the tacrolimus is released at the 5 hour time point, (c) 40% of the tacrolimus is released within 10 to 14 hours, (d) 63.5% or less of the tacrolimus is released at the 12 hour time point, and (e) each composition releases the tacrolimus with a substantial zero order release profile over an extended period of time defined by the release from the 8 hours time point to the 15 hours time point, the substantial zero order release being defined as a linear release profile with a deviation of at the most ±15%, when tested according to the USP II dissolution test (paddle) or USP I dissolution test (basket) method at a rotation of 50 rpm in a medium at pH 4.5 comprising 0.005% hydroxypropylcellulose.

19. The method of claim 14, which when administered once daily in steady state to a healthy subject or a patient, the swing of the blood concentrations of tacrolimus measured as $(C_{max}-C_{min})/C_{min}$ is less than the swing observed when administering either the tacrolimus dosage form approved by the European Agency for the Evaluation of Medicinal Products (EMEA) on Apr. 23, 2007 or tacrolimus dosage form approved under U.S. New Drug Application No. 050708 in a once daily regimen and being determined under similar conditions and administered in similar molecular daily dosages of the tacrolimus.

20. The method of claim 14, wherein $T_{max}$ on day 1, when administered under fasting conditions, is between 4 hours and 24 hours.

21. The method of claim 14, wherein 40% of the tacrolimus in each extended release composition is released within 11 to 13 hours, when tested according to the USP II dissolution test (paddle) or USP I dissolution test (basket) method at a rotation of 50 rpm in a medium at pH 4.5 comprising 0.005% hydroxypropylcellulose.

22. The method of claim 14, wherein 50% of the tacrolimus in each extended release composition is released within 13 to 17 hours, when tested according to the USP II dissolution test (paddle) or USP I dissolution test (basket) method at a rotation of 50 rpm in a medium at pH 4.5 comprising 0.005% hydroxypropylcellulose.

23. The method of claim 14, wherein (a) at least 8% of the tacrolimus is released at the 4 hour time point after administration of each composition, (b) less than 25% of the tacrolimus is released at the 5 hour time point, (c) 50% of the tacrolimus is released within 13 to 17 hours, (d) 63.5% or less of the tacrolimus is released at the 12 hour time point, and (e) each composition releases the tacrolimus with a substantial zero order release profile over an extended period of time defined by the release from the 8 hours time point to the 15 hours time point, the substantial zero order release being defined as a linear release profile with a deviation of at the most ±15%, when tested according to the USP II dissolution test (paddle) or USP I dissolution test (basket) method at a rotation of 50 rpm in a medium at pH 4.5 comprising 0.005% hydroxypropylcellulose.

24. The method of claim 23, wherein 50% of the tacrolimus in each extended release composition is released within 14 to 16 hours, when tested according to the USP II dissolution test (paddle) or USP I dissolution test (basket) method at a rotation of 50 rpm in a medium at pH 4.5 comprising 0.005% hydroxypropylcellulose.

25. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, and (iii) the patient is concomitantly treated with mycophenolate mofetil.

26. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, and (iii) the patient is concomitantly treated with a corticosteroid.

27. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, and (iii) the patient is African-American.

28. A method of prophylaxis of organ rejection in a de novo kidney transplant patient comprising once daily orally administering to the patient an effective amount of tacrolimus in the form of one or more extended release compositions comprising tacrolimus, wherein (i) the initial dose of tacrolimus is 0.14 mg/kg/day, (ii) the target trough concentration for the tacrolimus is 5-10 ng/mL, and (iii) the plasma concentration of tacrolimus in the patient is maintained at a therapeutically effective amount without inducing nephrotoxicity or neurotoxicity.

* * * * *